(12) United States Patent
Jansen et al.

(10) Patent No.: US 10,799,546 B1
(45) Date of Patent: Oct. 13, 2020

(54) MODULAR, INTEGRATED PROCESS AND APPARATUS FOR EXTRACTING, REFINING AND REMEDIATING ACTIVE SUBSTANCES FROM PLANT MATERIAL

(71) Applicant: Biomass Oil Separation Solutions, LLC, Roscoe, IL (US)

(72) Inventors: Robert Patrick Jansen, Collinsville, IL (US); Neta Matis, Hod Hasharon (IL); Adam F. Tracy, Roscoe, IL (US); Lucas A. Burke, South Beloit, IL (US); Brendon C. Stout, Burlington, NC (US)

(73) Assignee: BIOMASS OIL SEPARATION SOLUTIONS, LLC, Roscoe, IL (US)

( * ) Notice: Subject to any disclaimer, the term of this patent is extended or adjusted under 35 U.S.C. 154(b) by 0 days.

(21) Appl. No.: 16/782,931

(22) Filed: Feb. 5, 2020

Related U.S. Application Data

(60) Provisional application No. 62/879,363, filed on Jul. 26, 2019, provisional application No. 62/943,133, filed on Dec. 3, 2019.

(51) Int. Cl.
*B01D 3/36* (2006.01)
*A61K 36/185* (2006.01)
*B01D 15/18* (2006.01)

(52) U.S. Cl.
CPC .............. *A61K 36/185* (2013.01); *B01D 3/36* (2013.01); *B01D 15/185* (2013.01)

(58) Field of Classification Search
CPC ....... B01D 3/36; B01D 15/185; A61K 36/185
See application file for complete search history.

(56) References Cited

U.S. PATENT DOCUMENTS

| | | | |
|---|---|---|---|
| 2,769,787 A | 11/1956 | Diamond | |
| 2,985,589 A | 5/1961 | Broughton et al. | |
| 4,048,205 A | 9/1977 | Neuzil et al. | |
| 4,049,688 A | 9/1977 | Neuzil et al. | |
| 4,066,677 A | 1/1978 | De Rosset et al. | |
| 4,305,882 A | 12/1981 | Emken et al. | |
| 4,332,623 A | 6/1982 | Ando et al. | |
| 4,379,751 A | 4/1983 | Yoritomi et al. | |
| 4,379,784 A | 4/1983 | Maier et al. | |
| 4,529,551 A | 7/1985 | Cleary et al. | |

(Continued)

FOREIGN PATENT DOCUMENTS

| | | |
|---|---|---|
| CN | 104194920 A | 12/2014 |
| CN | 106860492 A | 6/2017 |

(Continued)

OTHER PUBLICATIONS

710Spirits. 710 Spirits Solubility Parameter. Northwest Scientific, Inc. (Dec. 20, 2018). Retrieved Jan. 23, 2020 from URL: <https://www.nwsci.com/customer/docs/SKUDocs/RMR/710%20Solubility%20Parameter.pdf>.3 Pages.

(Continued)

*Primary Examiner* — Jonathan Miller
(74) *Attorney, Agent, or Firm* — Wilson Sonsini Goodrich & Rosati

(57) ABSTRACT

The present disclosure relates to scalable processes for extracting, refining and remediating extracts of natural products, such as plant material and for providing well controlled refined extracts.

19 Claims, 35 Drawing Sheets

(56) References Cited

U.S. PATENT DOCUMENTS

| | | | |
|---|---|---|---|
| 4,617,177 A | 10/1986 | Schumacher | |
| 4,721,584 A | 1/1988 | Arai et al. | |
| 4,961,881 A | 10/1990 | Ou | |
| 4,970,002 A | 11/1990 | Ando et al. | |
| 5,064,539 A | 11/1991 | Tanimura et al. | |
| 5,102,553 A | 4/1992 | Kearney et al. | |
| 5,556,546 A | 9/1996 | Tanimura et al. | |
| 6,033,706 A | 3/2000 | Silkeberg et al. | |
| 6,093,326 A | 7/2000 | Heikkila et al. | |
| 6,187,204 B1 | 2/2001 | Heikkild et al. | |
| 6,254,734 B1 | 7/2001 | Sephton | |
| 6,365,416 B1* | 4/2002 | Elsohly | G01N 30/12 436/161 |
| 6,379,554 B1 | 4/2002 | Kearney et al. | |
| 6,403,126 B1 | 6/2002 | Webster et al. | |
| 6,482,268 B2 | 11/2002 | Hyoky et al. | |
| 6,482,323 B2 | 11/2002 | Tanimura et al. | |
| 6,685,781 B2 | 2/2004 | Hyoky et al. | |
| 7,595,070 B2 | 9/2009 | Olansky et al. | |
| 7,667,061 B2 | 2/2010 | Binder et al. | |
| 7,700,368 B2 | 4/2010 | Flockhart et al. | |
| 8,088,710 B2 | 1/2012 | Binder et al. | |
| 8,415,285 B2 | 4/2013 | Develter et al. | |
| 8,846,409 B2 | 9/2014 | Flockhart et al. | |
| 8,937,191 B2 | 1/2015 | Oroskar et al. | |
| 9,034,395 B2 | 5/2015 | Whittle et al. | |
| 9,199,960 B2 | 12/2015 | Ferri | |
| 9,295,810 B2 | 3/2016 | Hicks et al. | |
| 9,340,475 B2 | 5/2016 | Mona et al. | |
| 9,937,218 B2* | 4/2018 | Towle | A61K 36/185 |
| 9,950,976 B1 | 4/2018 | Keller | |
| 9,956,498 B1 | 5/2018 | Tucker | |
| 9,987,567 B1 | 6/2018 | Ko | |
| 1,014,370 A1 | 12/2018 | Kotra et al. | |
| 1,015,517 A1 | 12/2018 | Feuer et al. | |
| 1,018,976 A1 | 1/2019 | Oroskar et al. | |
| 1,019,515 A1 | 2/2019 | Whittle et al. | |
| 1,020,719 A1 | 2/2019 | Nadal Roura | |
| 10,239,808 B1* | 3/2019 | Black | C07B 63/00 |
| 1,024,643 A1 | 4/2019 | Changoer et al. | |
| 1,030,124 A1 | 5/2019 | Zhang et al. | |
| 1,040,645 A1 | 9/2019 | Ko et al. | |
| 1,041,384 A1 | 9/2019 | Tegen et al. | |
| 1,041,470 A1 | 9/2019 | Tegen et al. | |
| 1,050,740 A1 | 12/2019 | Galyuk | |
| 1,058,316 A1 | 3/2020 | Raderman | |
| 1,060,446 A1 | 3/2020 | Oroskar et al. | |
| 1,061,080 A1 | 4/2020 | Metcalf | |
| 1,061,171 A1 | 4/2020 | Chen et al. | |
| 10,624,872 B1 | 4/2020 | McCorkle et al. | |
| 1,064,769 A1 | 5/2020 | Erfurt et al. | |
| 1,066,213 A1 | 5/2020 | Qu et al. | |
| 1,066,924 A1 | 6/2020 | Thomas et al. | |
| 2004/0143126 A1 | 7/2004 | Webster et al. | |
| 2005/0266108 A1 | 12/2005 | Flockhart et al. | |
| 2006/0167283 A1 | 7/2006 | Flockhart et al. | |
| 2007/0093665 A1 | 4/2007 | Burdick et al. | |
| 2007/0128236 A1* | 6/2007 | Erskine | A01N 65/00 424/405 |
| 2008/0103193 A1 | 5/2008 | Castor et al. | |
| 2010/0298579 A1 | 11/2010 | Steup et al. | |
| 2013/0146542 A1 | 6/2013 | Huang et al. | |
| 2015/0126754 A1 | 5/2015 | Fernandez et al. | |
| 2015/0203434 A1 | 7/2015 | Flockhart et al. | |
| 2016/0002133 A1 | 1/2016 | Mona, III et al. | |
| 2016/0228787 A1 | 8/2016 | Payack | |
| 2017/0020944 A1* | 1/2017 | Towle | B01D 3/143 |
| 2017/0022132 A1 | 1/2017 | Mona, III et al. | |
| 2017/0051231 A1 | 2/2017 | Mancosky | |
| 2017/0071992 A1 | 3/2017 | Tomaso | |
| 2017/0240840 A1* | 8/2017 | Privitera | C11B 9/02 |
| 2017/0266153 A1 | 9/2017 | Levy et al. | |
| 2017/0312651 A1 | 11/2017 | Galyuk | |
| 2018/0010066 A1 | 1/2018 | Stantchev | |
| 2018/0147247 A1 | 5/2018 | Ivanov | |
| 2018/0162828 A1* | 6/2018 | Nadal Roura | B01D 11/0203 |
| 2018/0282250 A1* | 10/2018 | Rutz | B01D 1/00 |
| 2018/0296617 A1* | 10/2018 | Rivas | B01J 19/126 |
| 2018/0355278 A1* | 12/2018 | Baumhardt | B01D 11/0284 |
| 2018/0361271 A1 | 12/2018 | Galyuk | |
| 2019/0010106 A1 | 1/2019 | Oroskar et al. | |
| 2019/0010107 A1 | 1/2019 | Oroskar et al. | |
| 2019/0010110 A1 | 1/2019 | Oroskar et al. | |
| 2019/0099697 A1 | 4/2019 | Sibal | |
| 2019/0276420 A1 | 9/2019 | Tegen et al. | |
| 2020/0038777 A1 | 2/2020 | Galyuk | |
| 2020/0048215 A1 | 2/2020 | Thomas et al. | |
| 2020/0071285 A1 | 3/2020 | Tegen et al. | |
| 2020/0080021 A1* | 3/2020 | Thomas | C11B 3/005 |
| 2020/0108044 A1 | 4/2020 | Hur | |
| 2020/0164012 A1 | 5/2020 | Raderman | |
| 2020/0165219 A1 | 5/2020 | Changoer et al. | |
| 2020/0172503 A1 | 6/2020 | Oroskar et al. | |
| 2020/0181050 A1 | 6/2020 | Cipolletti et al. | |
| 2020/0188812 A1 | 6/2020 | Galyuk | |
| 2020/0190002 A1 | 6/2020 | Tegen et al. | |

FOREIGN PATENT DOCUMENTS

| | | |
|---|---|---|
| CN | 107365622 A | 11/2017 |
| GB | 2240053 A | 7/1991 |
| GB | 2400320 A | 10/2004 |
| GB | 2408978 B | 4/2006 |
| WO | WO-9636684 A1 | 11/1996 |
| WO | WO-2004026857 A2 | 4/2004 |
| WO | WO-2006053766 A1 | 5/2006 |
| WO | WO-2007075499 A3 | 9/2007 |
| WO | WO-2014072862 A1 | 5/2014 |
| WO | WO-2015032519 A1 | 3/2015 |
| WO | WO-2016004410 A1 | 1/2016 |
| WO | WO-2017040938 A1 | 3/2017 |
| WO | WO-2017194173 A1 | 11/2017 |
| WO | WO-2018187500 A1 | 10/2018 |
| WO | WO-2018190935 A1 | 10/2018 |
| WO | WO-2019010419 A1 | 1/2019 |
| WO | WO-2019087074 A2 | 5/2019 |
| WO | WO-2019100172 A1 | 5/2019 |
| WO | WO-2019113187 A1 | 6/2019 |
| WO | WO-2019119153 A1 | 6/2019 |
| WO | WO-2019130201 A1 | 7/2019 |
| WO | WO-2019156931 A1 | 8/2019 |
| WO | WO-2019173582 A1 | 9/2019 |
| WO | WO-2020018453 A1 | 1/2020 |
| WO | WO-2020028198 A1 | 2/2020 |
| WO | WO-2019207319 A9 | 3/2020 |
| WO | WO-2020046822 A1 | 3/2020 |
| WO | WO-2020084412 A1 | 4/2020 |
| WO | WO-2020084427 A1 | 4/2020 |
| WO | WO-2020117688 A2 | 6/2020 |
| WO | WO-2020124014 A1 | 6/2020 |

OTHER PUBLICATIONS

Amirav, et al. Approaching a Step Forward Towards the CSI Vision—Cannabis Seeds Identification with the 5975-SMB GC-MS and Cold El. Webpage. blog.avivanalytical.com/2012/12/approaching-step-forward-towards-csi.html. 2012. Accessed on Nov. 22, 2018. 6 Pages.

Angelova et al. Bio-accumulation and distribution of heavy metals in fibre crops (flax, cotton and hemp). Industrial Crops and Products 19(3):197-205 (2004).

Atkins, et al. Analysis of Cannabis and Hemp Products for Heavy Metals. Poster. SPEX CertiPrep (2017). 1 Page.

Atkins, P. Analysis of Heavy Metal Concentrations and Human Exposure from Hemp Oils and Hemp Products. Poster. SPEX CertiPrep (2017). 1 Page.

Baram et al.: The Heterogeneity and Complexity of Cannabis Extracts as Antitumor Agents. Oncotarget 10(41): 4091-4106 (2019).

Berman et al. A new ESI-LC/MS approach for comprehensive metabolic profiling of phytocannabinoids in Cannabis. Scientific Reports 8:14280 (2018). Published online Sep. 24, 2018. 15 pages.

(56) References Cited

OTHER PUBLICATIONS

Brooks, et al. Optimization of The Bleaching Process. AOCS Lipid Library. (2013). 13 Pages.

Burke, J. Solubility parameters: theory and application. (Aug. 1984).The Oakland Museum of California. Part 2—The Hildebrand Solubility Parameter. 5 Pages.

Cochran, J.: Medical Marijuana Solvent Extraction Efficiency—Potency Determinations with GC-FID.https://blog.restek.com/?p=3018. 19 pages (2011).

Co-pending U.S. Appl. No. 16/742,722, filed Jan. 14, 2020.

Cruz-Forero et al.: Calculation of Thermophysical Properties of Oils and Triacylglycerols Using an Extended Constituent Fragments Approach. CT&F—Ciencia, Tecnología y Futuro 5 (1): 67-82 (2012).

Curran, et al. Argentation resin chromatography of diterpene resin acids. Journal of the American Oil Chemists Society 58.11 (1981): 980-982.

Davis et al.: The Preparation and Analysis of Enriched and Pure Cannabinoids from Marihuana and Hashish. Chemistry and Life Sciences Laboratory, Research Triangle Institute. 33(4): 453-460 (1970).

Eboh, et al. Analysis of heavy metal content in *Canabis* leaf and seed cultivated in southern part of Nigeria. Pakistan J Nutr 4 (2005): 349-351.

Food Fats and Oils. Institute of Shortening and Edible Oils. (2016). 30 pages.

Gauvin, et al. Marijuana Toxicity: Heavy Metal Exposure Through State-Sponsored Access to "la Fee Verte". Pharmaceut Reg Affairs. 2018. 7:1. 10 Pages.

Glod, B. Principles and applications of ion-exclusion chromatography. Acta Chromatographica, No. 7, 1997. pp. 72-88.

Hamm, et al. Edible oil processing. John Wiley & Sons, 2013. 340 Pages.

Hong, et al. A review size-exclusion chromatography for the analysis of protein biotherapeutics and their aggregates. Journal of liquid chromatography & related technologies 35.20 (2012): 2923-2950.

Iffland et al.: Decarboxylation of Tetrahydrocannabinolic acid (THCA) to active THC. European Industrial Hemp Association (EIHA). 3 pages (2016).

Jukes et al. The Combination of Certain Fatty Acids with Lysine, Arginine and Salamine. J Biol Chem 110:9-16 (1935).

Juza et al.: Simulated moving-bed chromatography and its application to chirotechnology. Trends in Biotechnology. 18(3): 108-118 (2000).

Lewis et al.: Chemical Profiling of Medical Cannabis Extracts. ACS Omega 2: 6091-6103 (2017).

Marican, et al .A review on pesticide removal through different processes. Environmental Science and Pollution Research 25.3 (Nov. 28, 2017): 2051-2064.

Munch, E. Degumming of Plants Oils for different applications. Society of Chemical Industry, Cairo (Mar. 20, 2007). 30 Pages.

Nevada State Division of Public and Behavioral Health Policy #MME005 titled "Medical Marijuana Establishment Heavy Metals Testing Standards" effective as of Feb. 18, 2015.

Pavlovic et al.: Quality Traits of "Cannabidiol Oils": Cannabinoids Content, Terpene Fingerprint and Oxidation Stability of European Commercially Available Preparations. Molecules 23: 1230. 22 pages (2018).

PCT/US2019/043795 International Search Report and Written Opinion dated Oct. 29, 2019.

Perrotin-Brunel. Sustainable Production of Cannabinoids with Supercritical CO2 Technologies. PhD Thesis. Technische Universiteit Delft (Apr. 2011). 216 pages.

Powers, D.: Remediation of Pesticides from First Pass Distillate via Liquid/Liquid Ex-traction and Chromatographic Adsorption. ARCON Journal. Received Feb. 13, 2018. 3 pages.

Prado et al. Scale-up study of supercritical fluid extraction process for clove and sugarcane residue. The Journal of Supercritical Fluids 56(3):231-237 (2011).

Purolite. Purolite Product Information. Chromalite Resins for Reverse-Phase Chromatography, Adsorption and SPE. 24 pages (2014).

Rajendran et al.: Simulated Moving Bed Chromatography for the Separation of Enantiomers. Journal of Chromatography A. 1216: 709-738 (2009).

Romano et al.: Cannabis Oil: Chemical Evaluation of an Upcoming Cannabis-Based Medicine. Cannabinoids 1(1): 1-11 (2013).

Rovetto et al. Supercritical carbon dioxide extraction of cannabinoids from *Cannabis sativa* L.The Journal of Supercritical Fluids 129:16-27 (2017). Available online Mar. 19, 2017.

Solvent Polarity Table. Miller's Home. https://sites.google.com/site/miller00828/in/solvent-polarity-table 6 pages (2019).

Triolein. Product Specification. Parchem—Fine & Specialty Chemicals. Form#: 2345. Date: Jan. 1, 2009. Revision: 7. Revision Date: Oct. 6, 2016. 1 page (2016).

U.S. Department of Health and Human Services Food and Drug Administration, Center for Drug Evaluation and Research (CDER), Center for Biologics Evaluation and Research (CBER). Q3C—Tables and List Guidance for Industry. [Jun. 2017] ICH. Revision 3. 10 pages.

Valeri et al.: Viscosities of Fatty Acids, Triglycerides ,and Their Binary Mixtures. JAOCS 74(10): 1221-1226 (1997).

Brian Windsor, Purolite International Ltd. Resin Types and Production (presentation). Society of Chemical Industry (SCI) (2012). 35 pages.

CBD Purification with Chromalite Chromatographic Resins (poster). Purolite Life Sciences (Apr. 25, 2020).

Chloride in Drinking-water. Background document for development WHO Guidelines for Drinking-water Quality. WHO/SDE/WSH/03.04/03. World Health Organization (2003). 9 pages. Originally published in Guidelines for drinking-water quality, 2nd ed. vol. 2. Health criteria and other supporting information, World Health Organization, Geneva, 1996.

Chojnacka et al. Bio-based Fertilizers: A Practical Approach Towards Circular Economy. Bioresour Technol Jan. 2020;295:122223.doi: 10.1016/j.biortech.2019.122223. Epub Oct. 3, 2019. 11 pages.

Derler. Master Thesis: Screening of organic acids suitable for stimulation treatments. OMV, Leoben, Austria (2018). 85 pages.

Engelhardt. Lead in Water—Significance, Sources, and Test Methods. Application Note: Lead Sources, Effects, and Test Methods. HACH (2015). 2 pages.

Engineering Bulletin: C104Plus and C104EPlus Hydrogen Cycle Operation Hydrochloric or Sulfuric Acid Regeneration. Purolite (2014). 16 pages.

Greenwald. The Dissociation of Some Calcium Salts. J Biol Chem 124:437-452 (1938).

Karlsson et al. Optimizing the Operation of a Sequential-Simulated Moving-Bed Separation Process Using MINLP. European Symposium on Computer Aided Process Engineering—10, pp. 463-468, Elsevier Science B.V. (2000).

Lead DOC316.53.01054. LeadTrak Fast Column Extraction Method (Method 8317). Hach Company (2007). Edition 7. 8 pages.

Mark Slagt, Dow Company. Ion Exchange Resin Selection (presentation). Society of Chemical Industry (SCI) (2012). 38 pages.

Purolite C104Plus (Product Data Sheet). Purolite (2020). Retrieved May 21, 2020 from URL: https://www.purolite.com/product-pdf/C104PLUS.pdf.2 pages.

Technical Data: C104Plus Weak Acid Cation Resin. Purolite Ion Exchange Resins. May 3, 2012. 6 pages.

Toth et al. Comprehensive evaluation and comparison of advanced separation methods on the separation of ethyl acetate-ethanol-water highly non-ideal mixture. Separation and Purification Technology 224 (2019) 490-508. Available online May 14, 2019.

U.S. Appl. No. 16/742,722 Office Action dated May 14, 2020.

Yang et al. Simulation of Pressure-swing Distillation for Separation of Ethyl Acetate-Ethanol-Water. IOP Conf. Series: Materials Science and Engineering 274 (2017) 012026 doi:10.1088/1757-899X/274/1/012026. 8 pages.

* cited by examiner

MODULAR, INTEGRATED PROCESS AND APPARATUS FOR EXTRACTING, REFINING AND REMEDIATING ACTIVE SUBSTANCES FROM PLANT MATERIAL

CROSS REFERENCE

This application claims the benefit of U.S. Provisional Patent Application No. 62/879,363, filed on Jul. 26, 2019, and U.S. Provisional Patent Application No. 62/943,133, filed on Dec. 3, 2019, each of which is entirely incorporated herein by reference.

BACKGROUND

The therapeutic activity of plant medicines can be attributed to the active constituents that they contain. In some cases, the intrinsic activity of natural products has been linked to specific chemical species, but in other cases the activity of the plant medicine may be considered to be due to a combination of constituents acting in concert. The active constituents may be present at varying concentrations in different plant strains and may depend on growing conditions. Furthermore, active constituents may be present at varying amounts in different parts of the plant.

*Cannabis* is a genus of plants that include three species: *Cannabis sativa*, *Cannabis indica*, and *Cannabis ruderalis*. This genus has long been in use for its hemp fiber material, and the active constituents have been used as milk, seeds and oils, for medicinal purposes and for recreational use. There has been a surge in research and development directed to utilization of the constituents of this genus for therapeutic purposes.

There is a need for generating a large variety of cannabis compositions to help find the most desired effect for every indication and every patient. The industry typically addresses this need by genetically developing more and more strains in order to increase the selection. Such development of strains can be expensive, complicated and takes time to form the required product.

SUMMARY

Many of the cannabis-derived products may utilize the primary psychoactive component of the Cannabis plant, tetrahydrocannabinol (THC). Cannabis plants initially contain tetrahydrocannabinolic acid (THCA) and cannabidiolic acid (CBDA); these compounds may break down to THC and cannabindiol (CBD) when exposed to UV light and/or heat. THC belongs to the larger family of cannabinoids. CBD is a non-psychoactive cannabinoid that can be used in medicinal preparations. According to *Handbook of Cannabis* (R. G. Partwee (Ed.), Oxford Univ. Press 2014, Ch. 1), by 2012, a total of 545 chemical compounds have been identified as constituents of *Cannabis sativa* L, out of which 104 were classified as cannabinoids and 441 classified as non-cannabinoids. With much research in this area in recent years, the number of identified compounds continues to grow. The identified cannabinoids may be classified into 11 types: (−)-Δ-9-trans-tetrahydrocannabinol (Δ9-THC), (−)-delta-8-trans-tetrahydrocannabinol (Δ8-THC), cannabigerol (CBG), cannabichromene (CBC), cannabidiol (CBD), cannabinodiol (CBND), cannabielsoin (CBE), cannabicyclol (CBL), cannabinol (CBN), cannabitriol (CBT), and miscellaneous-type cannabinoids. Some of the identified cannabinoids may undergo chemical transformation under certain conditions. Currently, the cannabinoids of greatest commercial interest comprise Δ9-tetrahydrocannabinol carboxylic acid A (Δ9-THC acid A), Δ9-tetrahydrocannabinol carboxylic acid B (Δ9-THC acid B) and the decarboxylated form Δ9-THC, as well as cannabidiolic acid (CBDA) and the decarboxylated form cannabidiol (CBD).

Compounds with biological interest derived from Cannabis have been discovered, resulting from the advent of sophisticated analysis methods (e.g., LC-MS/MS) and the growing interest in the pharmaceutical potential of cannabinoids and other bioactive constituents that are found in various varieties of the cannabis genre (A new ESI-LC/MS approach for comprehensive metabolic profiling of phytocannabinoids in cannabis P. Berman et. al., Scientific Reports, 2018, 8, 14280). Many of these compounds are yet to be further characterized for the absolute chemical structure, and, therefore, have only been identified by, for example, relative elution time and mass. They are currently referred to by peak numbers; for example, 329-11a and 329-11c, 327-13a to 327-13c, 313-16b and 331-18a were identified in decarboxylated, CBD-rich extracts, whereas 329-11b, 329-11d, 331-18b and 331-18d were identified in Δ9-THC-rich extracts. Studies into the potential activity of these constituents are ongoing, but many compounds are expected to have beneficial pharmaceutical activity (see, for example, The heterogeneity and complexity of Cannabis extracts as antitumor agents, L. Baram et. al., Oncotarget, 2019, 10 (41), 4091).

In addition, it is suggested that terpenes extracted from *Cannabis sativa* L may have some effects, including therapeutic effects, and may alter the effects of cannabinoids in certain indications. The most common terpenes that have been identified include α-pinene, myrcene, limonene, β-caryophyllene, linalool, humulene, ocimene, and terpinolene, each of which can be isolated from other herbal plants or industrially produced by fermentation.

The present disclosure relates to refining processes for extracts of naturally-occurring compounds, which may be extracted from biomass. In particular, systems and processes for providing highly refined cannabinoids and terpenes are described.

Simulated moving bed (SMB) chromatography is a large-scale separation process that may make liquid chromatography more economically feasible than large-scale batch (single-column) chromatography methods. SMB chromatography is generally operated in an isocratic mode that utilizes countercurrent separation by continuous flow of a single solvent between separation zones (e.g., feed and desorbent inlets and extract and raffinate outlets). SMB chromatography differs from batch methods in that SMB methods use multiple columns containing the solid adsorbent (beds). Additionally, instead of flowing the desorbent (e.g., a fluid) through one static bed, the desorbent may be moved in the opposite direction of the beds to achieve a countercurrent flow (e.g., a simulated movement). Valves dispersed between the columns may allow for the input and output of fluid streams that can be switched from column to column in the direction of fluid flow. The output of these streams provides a way to remove the raffinate at appropriate points between the columns.

The higher economic feasibility results from, for example, an enhanced productivity, resulting from, for example, a more efficient utilization of the solid and liquid phases of the chromatography process. However, while SMB chromatography can be effective at separating mixtures of a few (e.g., two or three) components, SMB chromatography is not effective for the separation of complex mixtures (e.g., cannabinoid extracts).

Sequential simulated moving bed (SSMB) chromatography is a more advanced multi-column chromatography method, which generally requires a sequential batch operation, and this method is more feasible for higher separation factor applications than SMB chromatography. SSMB chromatography takes advantage of multiple (e.g., at least 2, 3, 4, 5, 6, 7, 8, 9, 10, or more) distinct zones each having different solvent conditions (e.g., in a "bind-wash-elute-clean-equilibrate" or step gradient sequence). While SSMB chromatography may require more pumps, inlets, outlets, and system control than SMB modes, it can enable straightforward control over the flow rates in each zone, allowing for better separation of complex mixtures. The advantages of SSMB compared to SMB include, for example, fewer columns (e.g., less resin), better control of parameters, such as, the pressure profile (e.g., can use more sensitive resins), better remediation of complex mixtures (e.g., mixtures of cannabinoids, terpenes, etc.), and better recovery (e.g., yield) and purity of the constituents of the mixture (e.g., the raffinate). SSMB chromatography processes may be better equipped for remediating complex mixtures (e.g., mixtures of cannabinoids, terpenes, or a combination thereof) than SMB chromatography processes.

Distillation of naturally-derived extracts, especially at temperatures exceeding the boiling point of constituents of an extract, can result in coke formation. Coking can result from, for example, the decomposition of constituents within a mixture being distilled. Coke can develop at any point during a distillation process, and the build-up of coke can adversely affect the efficiency of the distillation process (e.g., yield and purity of the distillate). Coke formation can be prevented using high-boiling additives, such as, for example, wash oils (e.g., high-boiling fatty acids). These high-boiling additives can help maintain a certain level of "wetness" in the distillation unit, preventing the formation of coking products.

In certain aspects, the present disclose provides method of preparing at least one plant-extracted constituent, the method comprising: (i) extracting a constituent from the plant material with a first solvent to obtain a loaded extractant; (ii) contacting the loaded extractant with an adsorbent, a desorbent, or a combination thereof to obtain a first refined extractant; (iii) concentrating the first refined extractant to obtain a first refined oil; (iv) contacting the first refined oil with at least one substance selected from the group consisting of a basic amino acid, a protamine, clay, water, activated carbon, filter aid, and ion exchange resin, or a combination thereof to obtain a second refined extractant; (v) concentrating the second refined extractant to obtain a second refined oil; and (vi) fractionating the second refined oil into at least one constituent with a supercritical or a sub-supercritical liquid to obtain at least one fractionated plant-extracted constituent. In some embodiments, prior to (iv), the first refined oil is contacted with a second solvent to obtain a second loaded extractant, wherein the second loaded extractant is subsequently contacted with at least one substance selected from the group consisting of a basic amino acid, a protamine, clay, water, activated carbon, filter aid, and ion exchange resin, or a combination thereof to obtain a second refined extractant. In some embodiments, prior to (vi), distilling the second refined oil to obtain a purified oil. In some embodiments, the purified oil is fractionated into at least one constituent with a supercritical or a sub-supercritical liquid to obtain at least one fractionated plant-extracted constituent.

In some aspects, the present disclosure provides a method, wherein fractionating further comprises: (a) contacting the second refined oil or the purified oil with supercritical $CO_2$ in a counter current extraction column, wherein the counter current extraction column comprises at least one contacting stage; (b) transferring an upper effluent of the column to an expansion tank, releasing $CO_2$ gas, thereby providing a constituent enriched in THC; and (c) transferring a bottom effluent of the column to an expansion tank, releasing $CO_2$ gas, thereby providing a constituent depleted of THC. In some embodiments, the extraction column comprises at least a first counter current column and a second counter current column, wherein each column is independently held at a pressure and temperature. In some embodiments, the first column is held at a pressure from 15 MPa to 25 MPa, and temperature from 35° C. to 65° C. In some embodiments, the second column is held at a pressure from 6 MPa to 15 MPa, and temperature from 35° C. to 65° C. In some embodiments, the first column is held at a pressure from 15 MPa to 25 MPa, and temperature from 35° C. to 65° C. and the second column is held at a pressure from 6 MPa to 15 MPa, and temperature from 35° C. to 65° C. In some embodiments, fractionating further comprises, prior to (b), feeding the supercritical mixture into a high-pressure decanting tank, wherein the supercritical mixture separates into the upper phase and the lower phase. In some embodiments, the supercritical $CO_2$ is fed at temperature from 310 K to 335 K and a pressure from 10 MPa to 25 MPa, wherein from 2000 to 8000 mass units of $CO_2$ are provided per unit mass of THC present in the feed stream.

In certain aspects, the method comprises treating the second refined oil with heat, thereby de-carboxylating at least one carboxylic acid containing constituent of the second refined oil. In some embodiments, treating the second refined oil with a catalyst, thereby de-carboxylating at least one carboxylic acid containing constituent of the second refined oil. In some embodiments, subsequent to step (v), treating the second refined oil with (a) heat and (b) a catalyst, thereby de-carboxylating at least one carboxylic acid containing constituent of the second refined oil. In some embodiments, treating the second refined oil with heat is under vacuum. In some embodiments, the second refined oil is heated at a temperature ranging from 105° C. to 170° C. In some embodiments, the second refined oil is heated at a temperature ranging from 135° C. to 160° C. In some embodiments, the second refined oil is heated for 0.5 hours to 4 hours. In some embodiments, the catalyst is a dicarboxylic acid, a tricarboxylic acid, an ion exchange resin, or any combination thereof. In some embodiments, the catalyst is selected from the group consisting of citric acid, oxalic acid, malic acid, ascorbic acid, tartaric acid, Amberlite, Amberlyst, Smopex, or Dowex. In some embodiments, (a) the second refined oil is heated at a temperature ranging from 105° C. to 170° C., and (b) the catalyst is a dicarboxylic acid, tricarboxylic acid, an ion exchange resin, or any combination thereof. In some embodiments, (a) the second refined oil is heated at a temperature ranging from 135° C. to 160° C., and (b) the catalyst is selected from the group consisting of citric acid, oxalic acid, malic acid, ascorbic acid, tartaric acid, Amberlite, Amberlyst, Smopex, or Dowex.

In certain aspects, at least 85% (% mol) of the cannabinoid constituents of the plant material are de-carboxylated in the purified oil.

In certain aspects, the distillation comprises a short path distillation. In some embodiments, the short path distillation comprises a wiped film evaporator.

In certain aspects, the supercritical or sub-supercritical liquid comprises $CO_2$.

In certain aspects, the method further comprises, prior to (i), feeding a plant material into a biomass feeding unit. In some embodiments, the biomass feeding unit further comprises a biomass grinding or sizing unit. In some embodiments, the biomass feeding unit processes the plant material, thereby producing a homogenized plant material. In some embodiments, the plant material is fed into at least one solvent extraction unit. In some embodiments, extracting a constituent from the plant material with a first solvent is performed by the at least one solvent extraction unit, thereby obtaining the loaded extractant. In some embodiments, the loaded extractant is transferred to a first refining unit. In some embodiments, in the first refining unit, the loaded extractant is contacted with an adsorbent, a desorbent, or a combination thereof to obtain a first refined extractant. In some embodiments, the first refined extractant is transferred to at least one evaporating system. In some embodiments, the first refined oil is produced by concentrating the first refined extractant in the at least one evaporating system. In some embodiments, the first refined oil is transferred to a second refining unit. In some embodiments, the first refined oil is contacted with the second solvent after concentration in the at least one evaporating system, thereby obtaining a second loaded extractant. In some embodiments, the second loaded extractant is transferred to a second refining unit. In some embodiments, the second refined extractant is produced by contacting the first refined oil with a substance of (iv) in the second refining unit. In some embodiments, the second refined extractant is produced by contacting the second loaded extractant with a substance of in the second refining unit. In some embodiments, the second refined extractant is transferred to at least one evaporating system. In some embodiments, the second refined oil is produced by concentrating the second refined extractant in the at least one evaporating system. In some embodiments, the second refined oil is transferred to at least one extracting unit. In some embodiments, the second refined oil is fractionated to at least one fractionated plant-extracted constituent using the at least one extracting unit. In some embodiments, the second refined extractant is transferred to at least one chemical conversion unit. In some embodiments, carboxylic acid-containing constituents within the second refined extractant are de-carboxylated using the at least one chemical conversion unit. In some embodiments, the second refined extractant comprising at least one de-carboxylated constituent is transferred to at least one extracting unit. In some embodiments, the second refined extractant comprising at least one de-carboxylated constituent is fractionated to at least one fractionated plant-extracted constituent using the at least one extracting unit. In some embodiments, the second refined extractant comprising at least one de-carboxylated constituent is transferred to a third refining unit. In some embodiments, a purified oil is obtained upon distilling the second refined extractant comprising at least one de-carboxylated constituent using the third refining unit. In some embodiments, the purified oil is transferred to at least one extracting unit. In some embodiments, the purified oil is fractionated to at least one fractionated plant-extracted constituent using the at least one extracting unit.

In some embodiments, the loaded extractant comprises at least one extracted constituent and water.

In some embodiments, the adsorbent is selected from the group consisting of silica gel, alumina, zeolites, polymers, resins, clay, clay minerals, ores, charcoal, activated carbon, or metals, such as Ni, Cu, Ag, Pt and colloids. In some embodiments, the adsorbent is selected from the group consisting of polymers, resins, clays, charcoal, activated carbon, or metals, such as Ni, Cu, Ag, Pt and colloids. In some embodiments, the adsorbent is selected from the group consisting of activated carbon. In some embodiments, the activated carbon is granulated activated carbon (GAC). In some embodiments, contacting with the GAC column occurs at temperature of 40° C. to 55° C. In some embodiments, contacting with GAC removes at least 10% of the tetrahydrocannabinoids present in the loaded extractant. In some embodiments, contacting with GAC removes at least 40% of the tetrahydrocannabinoids present in the loaded extractant. In some embodiments, the tetrahydrocannabinoids are selected from the group consisting of THC, (−)-Δ-9-trans-tetrahydrocannabinol (Δ9-THC), (−)-delta-8-trans-tetrahydrocannabinol (Δ8-THC), or THCA.

In certain aspects, the desorbent is selected from the group consisting of 1-butanol, ethyl acetate, ethyl formate, 2-methyl-1-butanol, ethanol, heptane, cyclohexane, 2-butanone, 2-propanol, or propylene glycol.

In certain aspects, the first refined oil of (iii) is obtained by evaporating at least one solvent from the first refined extractant. In some embodiments, the first refined oil of (iii) is obtained by evaporating at least one solvent and water from the first refined extractant.

In certain aspects, the first refined oil comprises extracted oil, solvent, and water, having a ratio of about 6 to 12 parts (solvent+water) to about 1 part extracted oil wt/wt.

In certain aspects, the second loaded extractant is contacted with activated carbon.

In certain aspects, the method further comprises: (a) contacting the first refined oil or the second loaded extractant with a solution of the basic amino acid, the protamine, or a combination thereof; (b) further contacting the first refined oil or the second loaded extractant with the clay, thereby obtaining a first slurry; (c) filtering at least one solid from the first slurry, thereby obtaining a first mother liquor comprising an aqueous phase and an organic phase; (d) separating the aqueous phase and the organic phase; (e) contacting the organic phase with an ion exchange resin, thereby obtaining a deionized organic phase; (0 contacting the deionized organic phase with activated carbon, thereby obtaining a second slurry; (g) filtering at least one solid from the second slurry, thereby obtaining a second mother liquor comprising an aqueous phase and an organic phase; (h) adding brine, deionized water or reverse osmosis water, or mixture thereof to the second mother liquor; (i) concentrating the second mother liquor, thereby obtaining an aqueous phase and a concentrated organic phase; and (j) separating the aqueous phase and the concentrated organic phase, thereby obtaining the second refined extractant. In some embodiments, further comprising, adding water to the first slurry. In some embodiments, the basic amino acid is selected from the group consisting of arginine, lysine, and histidine. In some embodiments, the protamine is an arginine rich, nuclear protein. In some embodiments, (a) and (b) are conducted (A) in one mixing tank, and (B) the temperature is from 55° C. to 65° C. In some embodiments, the method further comprises contacting the loaded extractant with water.

In some embodiments, the clay is selected from the group consisting of Fuller's Earth, Kaolin clay, bentonite, diatomaceous earth, magnesium silicate (such as Florisil® or Magnesol® Polysorb), or a mixture thereof.

In some embodiments, the ion exchange resin is a strong acid ion exchange resin (SAC) or a weak acid ion exchange resin (WAC), and the temperature is from 45° C. to 60° C. In certain embodiments, the ion exchange resin is a WAC resin. In some embodiments, the WAC resin is in a Na+ form, H+ form, or a mixture thereof.

In some embodiments, the deionized organic phase is contacted with powdered activated carbon (PAC) at a temperature from 35° C. to 65° C. In some embodiments, the deionized organic phase is contacted with powdered activated carbon (PAC) at a temperature from 40° C. to 50° C.

In some embodiments, at least a portion of the separated aqueous phase is further combined with the second refined extractant prior to evaporating.

In some embodiments, the brine is a solution of a salt that is selected from the group consisting of sodium chloride, sodium acetate, sodium formate, or any mixture thereof. In certain embodiments, the brine is a solution of salt that comprises sodium acetate at a concentration from 0.5% to 4% wt/wt.

In some embodiments, solvent and water are evaporated in (v) to obtain the second refined oil.

In some embodiments, the purified oil is fractionated with supercritical $CO_2$ at temperature from 310 K to 335 K and a pressure from 10 MPa to 25 MPa. In some embodiments, from 0.150 g to 0.500 g of THC of the purified oil is extracted per 1 Kg of $CO_2$, providing a fractionated plant-extracted constituent rich in tetrahydrocannabinol (THC) and a fractionated plant-extracted constituent depleted from THC.

In some embodiments, separating the aqueous phase and the organic phase is accomplished by decantation.

In some embodiments, the plant material comprises cannabis. In some embodiments, the extracted constituents comprise cannabinoids and terpenes. In some embodiments, the plant material comprises green, dried, or pelletized material.

In some embodiments, the solvent: (a) is categorized as class 3 according to Q3C—Table and Lists Guidance for Industry (US Department of Health and Human Services, FDA, CDER, CBER), June 2017 ICH rev. 3; and (b) forms a heterogeneous azeotrope with water, wherein the solvent and the azeotrope have a boiling point lower than the boiling point of water.

In some embodiments, the first solvent comprises a mixture of solvents. In some embodiments, the second solvent comprises a mixture of solvents. In some embodiments, the first solvent is the same as the second solvent. In some embodiments, the solvent forms a heterogeneous azeotrope with water, wherein the heterogeneous azeotrope has a boiling point lower than the boiling point of the solvent. In some embodiments, the solvent has a ratio of water to solvent, Rw/Rs, that is greater in the vapor phase of the azeotrope than in the solvent liquid phase. In some embodiments, the solvent comprises a Hildebrand solubility parameter ranging from 10 MPa to 40.0 MPa½. In some embodiments, the solvent comprises a Hildebrand solubility parameter ranging from 18 MPa to 20.0 MPa½. In some embodiments, the solvent is selected from the group consisting of 1-butanol, ethyl acetate, ethyl formate, 2-methyl-1-butanol, ethanol, heptane, cyclohexane, 2-butanone, 2-propanol, or propylene glycol. In some embodiments, the solvent is ethyl acetate or ethyl formate.

In some embodiments, the solvent comprises a carboxylic acid. In some embodiments, the carboxylic acid is a dicarboxylic acid or a tricarboxylic acid. In some embodiments, the dicarboxylic acid or tricaboxylic acid is selected from the group consisting of citric acid, oxalic acid, malic acid, ascorbic acid, or tartaric acid.

In some embodiments, the method is a continuous process at industrial or semi-industrial scale.

In some embodiments, the method is an integrated process for preparing at least one plant-extracted constituent.

In some embodiments, extracting the constituent from the plant material of (i) is conducted from 10° C. to 45° C. In some embodiments, an evaporation device selected from the group consisting of an evaporator, a stripper, or a dryer is used for concentrating, wherein the evaporation device further comprises a barometric condenser.

In some embodiments, concentrating occurs at temperature from 40° C. to 85° C. at a pressure from 100 mmHg to 760 mmHg. In some embodiments, concentrating occurs at a temperature from 40° C. to 60° C. at a pressure of 200 mmHg to 400 mmHg. In some embodiments, concentrating occurs at a temperature from 60° C. to 85° C. at a pressure of 150 mmHg to 300 mmHg.

In some embodiments, the constituents of the purified oil comprises one, two, three, four, five, six, seven, eight, or any combination thereof, characteristics selected from (i) at least 85% wt cannabinoids; (ii) at most 1% wt/wt fatty acids (iii) at most 30 ppm heavy metals; (iv) at most 5000 µg/g ethanol; (v) at most 3000 µg/g methanol; (vi) at most 5000 µg/g ethyl acetate; (vii) at most 5000 µg/g butane; and (viii) at most 290 µg/g hexane. In some embodiments, the heavy metals are selected from the group consisting of mercury, arsenic, cadmium, lead, or any combination thereof.

In some embodiments, the concentration of THC in the purified oil can be controlled to (i) at most 0.001% wt/wt. In some embodiments, the concentration of THC in the purified oil can be controlled to 0.001% to 0.3% wt/wt. In some embodiments, the concentration of THC in the purified oil can be controlled to at least 0.3% wt/wt. In some embodiments, the concentration of THC in the purified oil can be controlled to at least 30% wt/wt. In some embodiments, the concentration of THC in the purified oil can be controlled to at least 50% wt/wt. In some embodiments, the concentration of THC in the purified oil can be controlled to at least 60% wt/wt. In some embodiments, at least one fractionated plant-extracted constituent comprises at least 95% of the THC present in the purified oil, thereby forming a THC-enriched fraction. In some embodiments, the THC-enriched fraction comprises 99% of the THC present in the purified oil. In some embodiments, the THC-enriched fraction comprises at most 25% of the CBD present in the purified oil. In some embodiments, the THC-enriched fraction comprises at most 15% of the CBD present in the purified oil. In some embodiments, the THC-enriched fraction comprises at most 5% of the CBD present in the purified oil. In some embodiments, the at least one fractionated plant-extracted constituent comprises at most 0.300% THC in the purified oil, thereby forming a THC-depleted fraction. In some embodiments, the THC-depleted fraction comprises at most 0.001% THC in the purified oil. In some embodiments, the concentration of CBN in the purified oil can be controlled to at most 2% wt/wt. In some embodiments, the concentration of CBN in the purified oil can be controlled to at least 2% wt/wt. In some embodiments, the concentration of CBN in the purified oil can be controlled to at least 20% wt/wt. In some embodiments, the concentration of CBN in the purified oil can be controlled to at least 30% wt/wt.

In some embodiments, the purified oil further comprises any of the characteristics, comprises one, two, three, four, five, or any combination thereof, characteristics selected from: (i) less than 0.14 µg/kg Arsenic; (ii) less than 0.09 µg/kg Cadmium; (iii) less than 0.15 µg/kg Lead; (iv) less than 0.29 µg/kg Mercury; and (v) less than 0.05% wt/wt phosphorous.

In some embodiments, the purified oil further comprises less than 0.05 mg/kg pesticides as analyzed by Official Methods of Analysis, AOAC Official Method 2007.01, Pesticide Residues in Foods by Acetonitrile Extraction and Partitioning with Magnesium Sulfate, AOAC INTERNATIONAL (modified) or CEN Standard Method EN 15662: Food of plant origin —Determination of pesticide residues using GC-MS and/or LC-MS/MS following acetonitrile extraction/partitioning and clean-up by dispersive SPE—QuEChERS method.

In some embodiments, the present disclosure provides an integrated modular system for extracting, refining, and fractionating plant constituents, comprising: (a) a biomass feeding unit; (b) at least one solvent extraction unit; (c) a first refining unit; (d) a second refining unit; (e) at least one chemical conversion unit; (f) a third refining unit; and (g) at least one extracting unit. In some embodiments, the biomass feeding unit further comprises a biomass grinding unit, sizing unit, or any combination thereof. In some embodiments, the sizing unit comprises a system for separation of particles based on density or with a system comprising a screen that the plant material passes through. In some embodiments, the screen comprises a plurality of openings that are at least ⅛ inches wide. In some embodiments, the plurality of openings are ¼ inches wide. In some embodiments, the system further comprises at least one solvent recycling unit. In some embodiments, the system further comprises pumps, pipes, and conveyors for transferring the biomass.

In some embodiments, the system is designed and constructed for continuous extracting, refining and fractionating high purity constituents from plant material.

In some embodiments, the system further comprises: (h) a central computer control; (i) control valves; (j) monitors and sensors for continuously monitoring temperature, pressure, or flow. In some embodiments, the monitors continuously monitor mass balance of incoming material and outflowing products.

In some embodiments, the at least one solvent recycling unit comprises: (i) at least one decanting tank; (ii) at least one evaporating system equipped with barometric condensers, wherein solvent and, optionally, water vapors are collected and transferred to the decanting tank; (iii) at least one stripper distillation system, wherein a distillate is collected and transferred to the decanting tank; (iv) at least one decanting system, wherein an aqueous phase is transferred to the at least one stripper distillation system to recover a solvent; (v) at least one press, wherein a pressed depleted biomass is transferred to a dryer, wherein subsequent liquids are transferred for further refining; (vi) at least one dryer, wherein solvent and, optionally, water vapors are collected and transferred to the decanting tank, wherein the solids comprise (a) depleted plant material after extraction and (b) loaded solid adsorbents; (vii) at least one chiller, wherein a solvent is chilled to a temperature; and (viii) at least one pump and piping system.

In some embodiments, the at least one decanting tank separates an aqueous phase and an organic phase. In some embodiments, the at least one evaporating system equipped with barometric condensers removes solvent and water from a process stream(s).

In some embodiments, the at least one stripper distillation system removes solvent residues from a waste water stream(s).

In some embodiments, the at least one decanting system separates a process stream(s) into an aqueous phase and an organic phase.

In some embodiments, the at least one press separates depleted biomass from a liquid(s).

In some embodiments, the at least one pump or piping system is operated under a controller to continuously collect a stream(s) from operation units and transfers a recycled stream(s) of chilled solvent to the extraction unit and the barometric evaporator(s).

In some embodiments, the plant biomass comprises cannabis. In some embodiments, the cannabis comprises cannabinoids and terpenes.

In some embodiments, the first refining unit comprises: (i) at least one column of granulated activated carbon (GAC); and (ii) at least one evaporator coupled to a barometric condenser. In some embodiments, the first refining unit comprises: (i) a cascade of one to five stirred reactors, at least one filter; and (ii) at least one evaporator coupled to a barometric condenser.

In some embodiments, the second refining unit comprises: (i) at least one temperature-controlled stirring tank; (ii) at least one filter; (iii) at least one decanting tank; (iv) at least one buffering tank; (v) at least one ion exchange column; (vi) at least one evaporator coupled to a barometric condenser; (vii) at least one decanter tank; and (viii) at least one settler.

In some embodiments, the system further comprises a second temperature-controlled stirring tank, a second filter, or any combination thereof. In some embodiments, the system further comprises a third temperature-controlled stirring tank.

In some embodiments, the filter separates solid adsorbents from a liquid. In some embodiments, at least one decanting tank separates an aqueous phase from an organic phase. In some embodiments, the second filter separates solid adsorbents from a liquid. In some embodiments, the at least one settler separates an aqueous phase from a refined oil phase. In some embodiments, the at least one chemical conversion unit comprises a stirred heating tank.

In some embodiments, the third refining unit comprises distillation unit. In some embodiments, the distillation unit comprises a short path distillation unit. In some embodiments, the short path distillation unit comprises a wiped film evaporator.

In some embodiments, the at least one extracting unit comprises: (i) a supply of pressurized $CO_2$; (ii) at least one feed pump; (iii) at least one counter current extraction column comprising at least one extraction stage; (iv) a heating system, wherein the temperature at each extraction stage is independent controlled; (v) an expansion tank with a release valve to release $CO_2$ as gas and collect at least one constituent of a top effluent; and (vi) an expansion tank with a release valve to release $CO_2$ as gas and collect at least one constituent of a bottom effluent.

In some embodiments, the at least one feed pump feeds a stream of a purified oil. In some embodiments, the counter current extraction column contacts the pressurized $CO_2$. In some embodiments, the counter current extraction column comprises at least two extraction stages. In some embodiments, the counter current extraction column comprises at least three extraction stages.

In some embodiments, the extracting unit comprises: (i) a supply of pressurized $CO_2$; (ii) at least one heat exchanger; (iii) at least one feed pump for purified oil; (iv) at least one mixing system for purified oil; (v) at least one decanting pressure tank; (vi) a first control valve to allow transfer of an upper phase to an expansion tank; (vii) a first expansion tank with a release valve to release $CO_2$ as gas and collect at least one constituent from the upper phase; (viii) a second control valve, to allow transfer of a bottom phase to an expansion tank; and (ix) a second expansion tank with a release valve to release $CO_2$ as gas and collect at least one constituent from the bottom phase.

In some embodiments, the at least one heat exchanger heats the pressurized $CO_2$. In some embodiments, the at least one feed pump feeds a stream of a purified oil. In some embodiments, the at least one mixing system mixes the pressurized and heated $CO_2$ and the purified oil into a pressure tank.

In some embodiments, the disclosure provides an extracted cannabis plant wherein the extracted plant comprises not more than 1% wt/wt dry base cannabinoids compared to the pre-extracted plant. In some embodiments, the extracted cannabis plant further comprises not more than 0.01, 0.1, or 1% wt/wt solvent.

In some embodiments, the present disclosure provides a method of preparing a wide spectrum plant extract, which is highly refined from non-active or toxic constituents and is remediated to remove intoxicating constituents to provide a pure broad-spectrum extract oil.

In certain aspects, the disclosure provides a method of producing at least one plant-extracted constituent, the method comprising (i) extracting a constituent from the plant material with a first solvent to obtain a loaded extractant; (ii) contacting the loaded extractant with an adsorbent, a desorbent, or a combination thereof to obtain a first refined extractant; (iii) concentrating the first refined extractant to obtain a first refined oil; (iv) contacting the first refined oil with at least one substance selected from the group consisting of a basic amino acid, a protamine, clay, water, brine, activated carbon, filter aid, and ion exchange resin, or a combination thereof to obtain a second refined extractant; (v) concentrating the second refined extractant to obtain a second refined oil; (vi) optionally distilling the second refined oil to obtain a purified oil; and (vii) remediating the second refined oil or the purified oil into at least one constituent to obtain at least one plant-extracted constituent.

In certain aspects, the disclosure provides a system for producing at least one plant-extracted constituent, the method comprising (i) extracting a constituent from the plant material with a first solvent to obtain a loaded extractant; (ii) contacting the loaded extractant with an adsorbent, a desorbent, or a combination thereof to obtain a first refined extractant; (iii) concentrating the first refined extractant to obtain a first refined oil; (iv) contacting the first refined oil with at least one substance selected from the group consisting of a basic amino acid, a protamine, clay, water, brine, activated carbon, filter aid, and ion exchange resin, or a combination thereof to obtain a second refined extractant; (v) concentrating the second refined extractant to obtain a second refined oil; (vi) distilling the second refined oil with a high boiling compound to obtain a purified oil; and (vii) remediating the second refined oil or the purified oil to obtain the at least one plant-extracted constituent.

In some embodiments, the remediating is by sequential simulated moving bed chromatography. In some embodiments, the sequential simulated moving bed chromatography is operated in a dual desorbent mode. In some embodiments, the sequential simulated moving bed chromatography sequence comprises (a) passing a feed stream comprising the second refined oil or the purified oil and a first desorbent (D1) into an adsorbent, and, with a second desorbent (D2), flushing an extract stream comprising the D1 and at least one plant-extracted constituent to be removed from the second refined oil or the purified oil, thereby washing the extract stream with the D2 and D1; (b) flushing a raffinate stream comprising the at least one plant-extracted constituent with the D1; (c) flushing the extract stream with the D1; and (d) advancing at least one oil wave front in the presence of the D1 by recycling the whole system from a last column to a first column of the sequence, wherein the at least one oil wave front comprises the at least one plant-extracted constituent. In some embodiments, the sequential simulated moving bed chromatography sequence comprises (a) (I) passing a feed stream comprising the second refined oil or the purified oil and a first desorbent (D1) into an adsorbent, (II) passing an extract stream with the D1, and (III) passing the extract stream with a second desorbent (D2), thereby washing the extract stream with the D2 and D1; (b) flushing, with the D1, the extract stream comprising the D2 and the at least one plant-extracted constituent to be removed from the second refined oil or the purified oil; (c) flushing a raffinate stream comprising the at least one plant-extracted constituent with the D1; and (d) advancing at least one oil wave front in the presence of the D1 by recycling the whole system from a last column to a first column of the sequence, wherein the at least one oil wave front comprises the at least one plant-extracted constituent.

In some embodiments, the system or method further comprise (1) stripping the D1 from the raffinate stream, thereby producing a purified raffinate oil, and (2) removing water, solvent, or a combination thereof from the purified raffinate oil to obtain the at least one plant-extracted constituent. In some embodiments, the system or method further comprise (1) stripping the D1 and D2 from the extract stream, thereby producing a residual oil, and, optionally, removing water from the residual oil to obtain a purified residual oil enriched with the at least one plant-extracted constituent to be removed from the second refined oil or the purified oil.

In some embodiments, the D1 and D2 each form an azeotrope with different physical properties, and wherein the stripping of the D1 and D2 is conducted under a different temperature and pressure. In some embodiments, the stripping of D2 is conducted at a temperature from about 25° C. to about 35° C. and a pressure from about 580 Torr to about 620 Torr, and the stripping of D1 is conducted at a temperature from about 45° C. to about 55° C. and a pressure from about 150 Torr to about 250 Torr.

In some embodiments, the at least one plant-extracted constituent is a rare cannabinoid or a bioactive constituent that is naturally present in cannabis, wherein the rare cannabinoid or the bioactive constituent comprises at most 10% of the second refined oil or the purified oil. Rare cannabinoid comprises at most 10% of the second refined oil or the purified oil.

In some embodiments, the rare cannabinoid or the bioactive constituent is further purified by another chromatography process, crystallization, a liquid/liquid extraction, a membrane filtration or any combination thereof. In some embodiments, the rare cannabinoid is selected from the group consisting of CBN, CBL, CBC, □9-THC, CBGA, CBG, CBGA-C4, CBG-C4, CBGVA, CBGV, CBGOA, CBGO, CBGMA, CBGM, Sesqui-CBGA, Sesqui-CBG, THCA, THC, THCA-C4, THC-C4, THCVA, THCV, THCOA, THCO, THCMA, THCM, CBDA, CBD, CBDA-C4, CBD-C4, CBDVA, CBDV, CBDOA (CBDA-C1), CBDO (CBD-C1), CBDMA, CBDM, CBCA, CBC, CBCA-C4, CBC-C4, CBCVA, CBCV, CBCOA, CBCO, CBNA, CBN, CBNA-C4, CBN-C4, CBNVA, CBNV, CBNOA, CBNO, CBNA-8-OH, CBN-8-OH, CBNM, CBEA-B, CBEA-A, CBE, CBEVA, CBEV, CBNDA, CBND, CBNDVA, CBNDV, d8-THC, CBLA, CBL, CBLV, CBLVA, CBTA-1, CBT-1, CBTV-1, CBTA-3, CBT-3, CBTV-3, CBT-2, CBT, CBV, OTHC, CBCF, CBF, CBR, DCBF, cis-THC and triOH-THC.

In some embodiments, the adsorbent is a reverse phase adsorbent. In some embodiments, the reverse phase adsorbent is selected from the group consisting of Chromalite® PCG600M, PCG900M, PCG1200M, PCG600C, PCG900C, PCG1200C, or any combination thereof. In some embodiments, the sequential simulated moving bed chromatography is performed at a temperature from about 15° C. to about 25° C. In some embodiments, the passing and flushing of (a) are performed simultaneously.

In some embodiments, the removing in (2) is performed with a stripping column optionally followed by degassing the purified raffinate stream using a degasifier. In some embodiments, the degassing is conducted at about 120° C. and at pressure from about 10 Torr to about 30 Torr. In some embodiments, the second refined oil and the raffinate stream, the purified oil and the raffinate stream, or a combination thereof are of substantially the same purity. In some embodiments, the at least one plant-extracted constituent comprises at least one intoxicating or non-active constituent, at least one constituent that fouls the reverse phase adsorbent, or a combination thereof. In some embodiments, the at least one intoxicating or non-active constituent and the at least one constituent that fouls the reverse phase adsorbent are the same constituent.

In some embodiments, at least about 90% of the constituents in the second refined oil, the purified oil, the raffinate stream, the extract stream, or any combination thereof have a molecular weight from about 250 g/mol to about 400 g/mol. In some embodiments, the molecular weight is from about 268 g/mol to about 332 g/mol. In some embodiments, at least about 85% of the constituents in the second refined oil, the purified oil, the raffinate stream, the extract stream, or any combination thereof have a molecular weight of 313 g/mol.

In some embodiments, the method further comprises condensing and mixing the D1 and D2 in a liquid/liquid separation unit to provide a phase of recycled D1 and a phase of recycled D2. In some embodiments, the D1 and D2 comprise one or more solvents that form an azeotrope with the at least one plant-extracted constituent in a binary or ternary mixture. In some embodiments, the binary mixture is ethanol-water or propanol-water. In some embodiments, the ternary mixture is selected from the group consisting of pentane-ethanol-water, hexane-ethanol-water, acetone-propanol-water, ethyl acetate-ethanol-water, heptane-ethanol-water, and cyclohexane-ethanol-water.

In some embodiments, the azeotrope has a boiling point (i) of at most about 90° C. and (ii) that is lower than the boiling point of each of the one or more solvents of the mixture. In some embodiments, the one ore more solvents and water are removed from the product by stripping, and remaining water is separated from the binary or ternary azeotrope by distillation. In some embodiments, the D1 and D2 separate into a first liquid phase and a second liquid phase from the ternary mixture at temperature from about 10° C. to about 50° C., wherein the first liquid phase comprises the D1 and the second liquid phase comprises the D2. In some embodiments, the D1 comprises a relative polarity from about 0.60 to about 0.75, and wherein the D2 comprises a relative polarity from about 0.65 to 0.001.

In some embodiments, a run time for the sequential simulated moving bed chromatography is from about 1 day to about 10 years. In some embodiments, the run time for the sequential simulated moving bed chromatography is at least about 6 days. In some embodiments, the method further comprises regenerating the reverse phase absorbent in the absence of stopping the process.

In some embodiments, the at least one plant-extracted constituent is selected from the group consisting of a cannabinoid, a fatty acid, a sterol, a flavonoid, and a terpene. In some embodiments, the distillation comprises a short path distillation. In some embodiments, the short path distillation comprises a wiped film evaporator. In some embodiments, the distilling is performed at a temperature from about 130° C. to about 200° C. and at a pressure of at most about 250 Torr. In some embodiments, the distilling is performed at a temperature from about 150° C. to about 200° C. and at a pressure of at most about 5 Torr.

In some embodiments, the method further comprises, prior to (iv), contacting the first refined oil with a second solvent to obtain a second loaded extractant, wherein the second loaded extractant is subsequently contacted with the at least one substance to obtain the second refined extractant.

In some embodiments, (vii) further comprises providing a refined extract of cannabis plant, which the refined extract of cannabis plant has a percentage of active constituents of at least 82%, and wherein the refined extract is fed to the remediation step of (vii). In some embodiments, the contacting in (ii) is in a cascade of 1-5 continuous stirred tanks. In some embodiments, the adsorbent of (ii) comprises activated carbon. In some embodiments, the method further comprises filtering the adsorbent from the first refined extractant.

In some embodiments, the second refined oil or the purified oil is substantially pure and comprises a percentage of cannabinoids at least about 82 wt %. In some embodiments, the percentage of cannabinoids is at least about 99 wt %. In some embodiments, the second refined oil or the purified oil is substantially pure and comprises CBD at a percentage of at least about 85 wt %.

In some embodiments, the first or second refined oil is mixed with at least one high-boiling compound. In some embodiments, the at least one high-boiling compound has a density of about 0.95 g/cm3; a boiling point greater than 250° C. at 5 torr; and/or a viscosity of at most about 30 centi-Stokes at 90° C. In some embodiments, the at least one high-boiling compound is miscible with the first or second refined oil. In some embodiments, the boiling point is greater than 250° C. at 10 Torr. In some embodiments, the at least one high-boiling compound is a fatty acid. In some embodiments, the fatty acid is a triglyceride or a fatty acid methyl ester. In some embodiments, the triglyceride is a homogeneous or heterogeneous triglycerides comprising at least 8 carbon atoms. In some embodiments, the fatty acid is selected from the group consisting of oleic acid, palmitic acid, linoleic acid, and linolenic acid.

In some embodiments, the clay is selected from the group consisting of Fuller's Earth, Kaolin clay, bentonite, diatomaceous earth, magnesium silicate (e.g., Florisil® and Magnesol® Polysorb), or a mixture thereof. In some embodiments, the ion exchange resin is a strong acid ion exchange resin (SAC), a weak acid ion exchange resin (WAC), a powdered activated carbon (PAC) resin, or any combination thereof, and the temperature is from 45° C. to 60° C. In some embodiments, the extracted constituents comprise cannabinoids and terpenes. In some embodiments, the plant material comprises green, dried, or pelletized plant material. In some embodiments, the green plant material comprises at most about 62% water.

In certain aspects, the disclosure provides a modular system, wherein the system extracts at least 100 kg/h of dry biomass, thereby producing an extracted plant material. In some embodiments, a residual solvent of the extracted plant material is removed to produce a solvent-removed extracted plant material. In some embodiments, the solvent removed extracted plant material is repurposed as an animal feed, a landfill material, a fuel, or any combination thereof.

In certain aspects, the disclosure provides a solvent-removed extracted plant material, comprising extractable constituents, wherein, subsequent to extraction with a desorbent or solvent, the solvent-removed extracted plant material comprises (i) less than about 5 wt % of the extractable constituents and (ii) less than 0.001 wt % of the solvent or desorbent.

In certain aspects, the disclosure provides a solvent-removed solid composition comprising: (i) activated carbon; (ii) amino acid or a protamine; (iii) clay; (iv) less than about 0.1 wt % volatile solvent; and (v) a high boiling compound, wherein the high boiling compound is selected from a homogeneous or a heterogeneous triglyceride or methyl ester fatty acid comprising at least 8 carbon atoms. In some embodiments, the homogeneous or the heterogeneous triglyceride or methyl ester fatty acid is selected from the group consisting of oleic acid, palmitic acid, linoleic acid, linolenic acid, or any combination thereof.

In certain aspects, the disclosure provides a method for purifying an oil comprising at least one cannabinoid constituent, the method comprising (a) combining said oil with a high-boiling compound, wherein at least 40% by weight (wt %) of said oil comprises one or more cannabinoids, and wherein said oil comprises at least one non-cannabinoid constituent; and (b) directing said oil into a distillation unit to separate said at least one cannabinoid constituent from said at least one non-cannabinoid constituent, thereby purifying said oil comprising at least one cannabinoid constituent.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE FIGURES

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "Fig." herein), of which:

DETAILED DESCRIPTION

Figure 1:
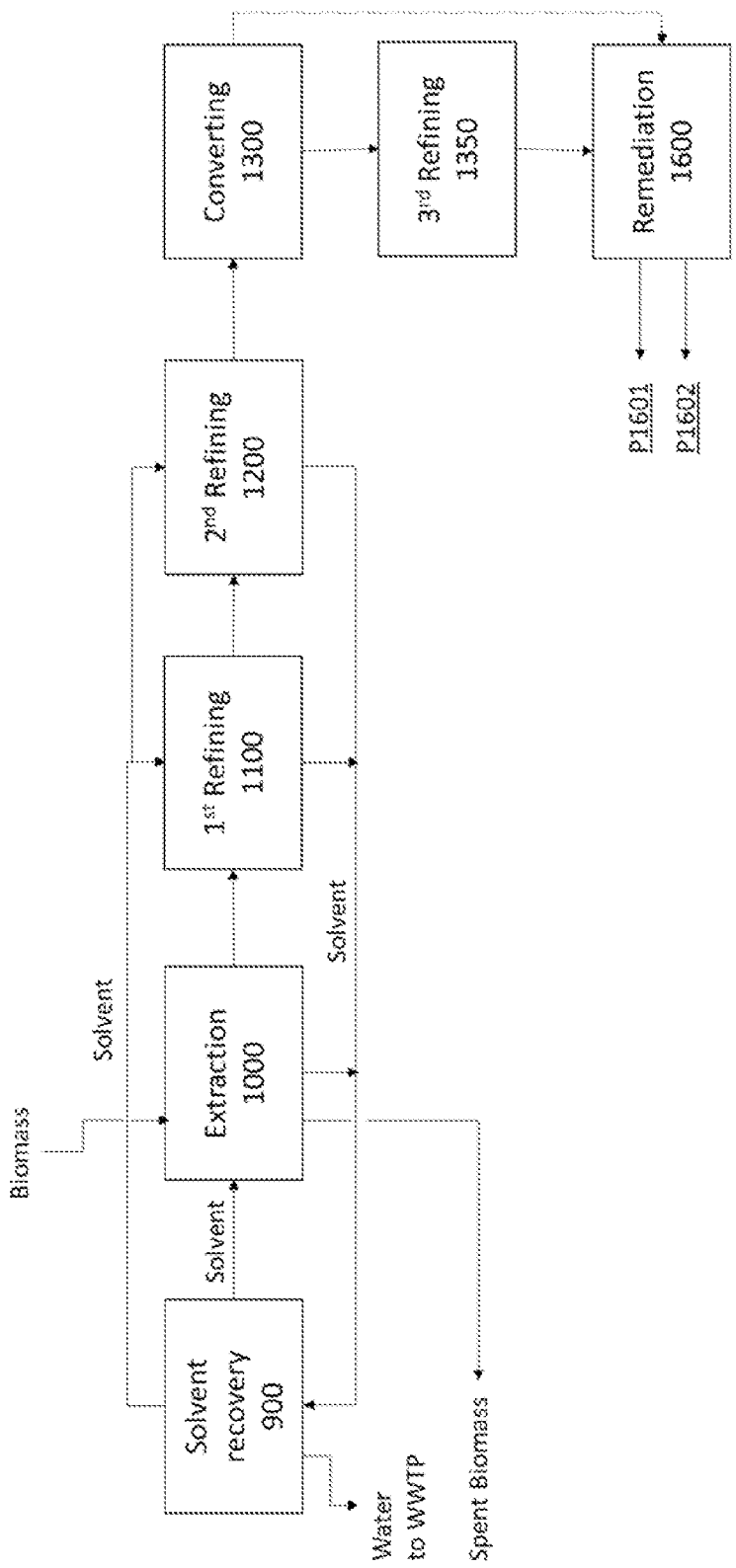
FIG. 1 illustrates a schematic diagram of a modular process to extract, refine and remediate constituents from plant material, to provide products enriched with a certain constituent or group of constituents, and to convert carboxylic acid constituents to their respective de-carboxylated constituents.

While various embodiments of the invention have been shown and described herein, it will be obvious to those skilled in the art that such embodiments are provided by way of example. Numerous variations, changes, and substitutions may occur to those skilled in the art without departing from the invention. It should be understood that various alternatives to the embodiments of the invention described herein may be employed.

As used herein, the singular forms "a," "an," and "the" include plural references unless the context clearly dictates otherwise. Any reference to "or" herein is intended to encompass "and/or" unless otherwise stated.

As used herein, the term "about" or "approximately" means within 10%, preferably within 10%, and more preferably within 5% of a given value or range.

As used herein, the term "fractionate", "fractionation", "fractionating", "remediate", "remediation", and "remediating" refer to the separation of at least one constituent from a plurality of constituents. The plurality of constituents may be derived from a plant material (e.g., cannabis). The plurality of constituents may comprise about 2, 3, 4, 5, 6, 7, 8, 9, 10, 20, 30, 40, 50, or more constituents. At least about 2, 3, 4, 5, 6, 7, 8, 9, 10, 20, 30, 40, 50, or more constituents may be separated from the plurality of constituents. For example, the plurality of constituents may be separated into multiple batches (e.g., 2, 3, 4, 5, or more batches), comprising at least about 1, 2, 3, 4, 5, 6, 7, 8, 9, 10, 20, or more constituents of the plurality of constituents.

The term "substantially" or "substantial" as used herein generally refers to at least about 60% or 60%, about 70% or 70%, or about or at 75%, 80%, 85%, 90%, 95%, 96%, 97%, 98%, 99%, or higher relative to a reference such as, for example, the original composition or state of an entity. Thus, a composition that is "substantially pure" indicates that at least about 60% or 60%, about 70% or 70%, or about or at 75%, 80%, 85%, 90%, 95%, 96%, 97%, 98%, 99%, or higher amounts of undesired compounds been removed from a composition.

The term "pure", as used herein, generally refers to a composition that is not mixed or adulterated with any other substance or material. For example, a "pure composition" may be a composition where at least about 75%, 80%, 85%, 90%, 95%, 96%, 97%, 98%, 99%, 99.99%, or higher amounts of undesired compounds are removed. Conversely, an "impure composition" can comprise undesired compounds. For example, a "loaded extractant" may comprise an "impure composition" (e.g., comprising chlorophylls, proteins, waxes, gums, etc.), but a refined oil, a "purified oil", an "extract stream", a "raffinate stream", or any combination thereof may not comprise an impure composition. On the other hand, a refined oil, a "purified oil", an "extract stream", a "raffinate stream", or any combination thereof may comprise an impure composition, and the impurity of the impure composition can be removed using the chromatography techniques described herein (e.g., SSMB). THC, or derivatives thereof, may not be an impurity.

The term "plant material", as used herein, refers to materials derived from plants. At least a portion of the plant material may be in the form of grass, rush, bark, wood, gourds, stems, roots, seeds, leaves, or flowers. In some embodiments, the plant material may be in the form of cannabis.

The terms "*cannabis*", "*cannabis* plant material", or "*cannabis* biomass", as used herein, may refer to whole cannabis plants and also parts thereof. In some embodiments, at least a portion of the *cannabis* (e.g., the aerials, stems, leaves, flowering heads, or any combination thereof) may contain bioactive constituent(s). The terms "*cannabis*", "*cannabis* plant material", and "*cannabis* biomass" may encompass freshly harvested plant material, and also plant material which has been subjected to a pre-treatment step (e.g., dried material). The terms "*cannabis*", "*cannabis* plant material", or "*cannabis* biomass" can refer to any strain or combination of strains (i.e., *Cannabis sativa, Cannabis indica,* or *Cannibis ruderalis*).

The term "cannabinoid" generally refers to both its carboxylic acid form and its decarboxylated form. For example, THC refers to tetrahydrocannabinol, while THCA refers to the carboxylated form of THC (tetrahydrocannabinolic acid). CBD refers to cannabidiol, while CBDA (cannabidiolic acid) refers to the carboxylated form of CBD. Other cannabinoid constituents may be: (−)-Δ-9-trans-tetrahydrocannabinol (Δ9-THC), (−)-delta-8-trans-tetrahydrocannabinol (Δ8-THC), cannabigerol (CBG), cannabichromene (CBC), cannabinodiol (CBND), cannabielsoin (CBE), cannabicyclol (CBL), cannabinol (CBN), cannabitriol (CBT).

The term "rare cannabinoid," as used herein, generally refers to a cannabinoid. The term "minor cannabinoid," as used herein, generally may be used interchangeably with "rare cannabinoid." A rare cannabinoid may comprise THC. A rare cannabinoid may not comprise THC. A rare cannabinoid may be present in a biomass (e.g., cannabis). A plurality of rare cannabinoids may be present in a biomass (e.g., cannabis). The amount of the rare cannabinoid present in the biomass (e.g., cannabis) may be at most about 20 wt %, 15 wt %, 10 wt %, 5 wt %, 1 wt %, 0.1 wt %, 0.01 wt %, 0.001 wt %, 0.0001 wt %, or less. The amount of the rare cannabinoid present in the biomass (e.g., cannabis) may be at least about 0.0001 wt %, 0.001 wt %, 0.01 wt %, 0.1 wt %, 1 wt %, 5 wt %, 10 wt %, 15 wt %, 20 wt %, or more. The amount of the rare cannabinoid present in the biomass (e.g., cannabis) may be from about 0.0001% to about 20%, about 0.01% to about 10%, or about 0.1% to about 5%. The rare cannabinoid may be selected from the group consisting of cannabinol (CBN), cannabicyclol (CBL), cannabichromene (CBC), Δ9-tetrahydrocannbinol (THC), cannabigerolic acid (CBGA), cannabigerol (CBG), CBGA-C4, CBG-C4, cannabigerovarin acid (CBGVA), cannabigerivarin (CBGV), cannabigerorcinic acid (CBGOA), cannabigerorcinol (CBGO), cannabigerolic acid monomethyl ether (CBGMA), cannabigerol monomethyl ether (CBGM), Sesqui-CBGA, Sesqui-CBG, tetrahydrocannabinolic acid (THCA), THC, THCA-C4, THC-C4, tetrahydrocannabivarin acid (THCVA), tetrahydrocannabivarin (THCV), tetrahydrocannabiorcolic acid (THCOA), tetrahydrocannabiorcol (THCO), tetrahydrocannabinolic acid methyl ester (THCMA), tetrahydrocannabinol methyl ester (THCM), cannabidiolic acid (CBDA), cannabidiol (CBD), CBDA-C4, CBD-C4, cannabidivarinic acid (CBDVA), cannabidivarinol (CBDV), cannabidiorcolic acid (CBDOA) (CBDA-C1), cannabiorcol (CBDO) (CBD-C1), cannabidiolic acid monomethyl ester (CBDMA), cannabinol monomethyl ester (CBDM), cannabichromenic acid (CBCA), cannabichrome carboxylic acid (CBCA)-C4, CBC-C4, cannabichromevarinic acid (CBCVA), cannabichromevarin (CBCV), cannabichromeorcinic acid (CBCOA), cannabichromeorcin (CBCO), cannabinolic acid (CBNA), CBNA-C4, CBN-C4, cannabivarinic acid (CBNVA), cannabivarin (CBNV), cannabiorcolic acid (CBNOA), cannabiorcol (CBNO), CBNA-8-OH, CBN-8-OH, cannabinol methyl ether (CBNM), cannabielsoic acid (CBEA)-B, CBEA-A, cannabielsoin (CBE), cannabivarinselsoinic acid (CBEVA), cannabivarinselsoinol (CBEV), cannabinodiolic acid (CBNDA), cannabinodiol (CBND), cannabivarinodiolic acid (CBNDVA), cannabivarinodiol (CBNDV), d8-THC, cannabicyclolic acid (CBLA), cannabicyclol (CBL), cannabicyclovarin (CBLV), cannabicyclovarinic acid (CBLVA), cannabitriolic acid (CBTA)-1, cannabitriol (CBT)-1, cannabitriolvarin (CBTV)-1, cannabitriolvarinic acid (CBTA)-3, CBT-3, CBTV-3, CBT-2, CBT, cannabivarin (CBV), tetrahydrocannabinol (OTHC), cannabichromanon (CBCF), cannabifuran (CBF), cannabiripsol (CBR), dehydrocannabifuran (DCBF), cis-THC, and triOH-THC.

Any strain of cannabis plant is suitable to be extracted by the processes disclosed herein. The term "strain" refers to different varieties of a particular plant genus. For example, the term strain can refer to different varieties of cannabis plants. Different cannabis strains often exhibit distinct chemical compositions with characteristic levels of cannabinoids and terpenes, as well as other components. Differing cannabinoid and terpene profiles associated with different cannabis strains can be useful for the treatment of different diseases, or for treating different subjects with the same disease. In some embodiments, the cannabis plant is a hemp plant. In some embodiments, the cannabis plant is a hybrid cannabis plant, or an asexual clone of said hybrid cannabis plant. In some embodiments, the cannabis plant is naturally bred or genetically engineered to express specifically high or specifically low concentration of at least one cannabinoid and/or at least one terpene. Any organ of a cannabis plant may be utilized in the subject methods, including but not limited to flowers, buds, kernel, leaves, stem, stalk, and roots.

The term "constituent" or "plant extracted constituent", as used herein, may refer to a(n) unaltered or altered component present within the plant material. In some embodiments, at least one constituent may be isolated from the plant material. The "constituents" may refer to pharmaceutically active ingredients, pharmaceutically inactive ingredients, flavor and aroma compounds, and any other chemical species that may be extracted from plant material. A constituent may be, for example, a cannabinoid, a fatty acid, a sterol, a flavonoid, or a terpene.

The term "loaded extractant", as used herein, may refer to a solution comprising at least one solute dissolved in a substance. In some embodiments, a loaded extractant may comprise at least one impurity. The term "loaded solvent" and "loaded extractant" are used interchangeably and refer to solvent comprising constituents extracted from a plant material.

The term "refined extractant", as used herein, may refer to a solution comprising at least one solute dissolved in a substance, wherein the solution has at least one less impurity present. In some embodiments, a refined extractant may comprise at least one impurity.

The term "refined oil", as described herein, may refer to an oil comprising at least one constituent extracted from a plant material, wherein the oil has at least one less impurity present. In some embodiments, a refined oil may comprise at least one impurity.

The term "feed stream" or "feed", as described herein, may generally refer to a liquid that is introduced to a chromatography sequence (e.g., sequential simulated moving bed chromatography (SSMB)). For example, a "feed stream" may comprise a "refined oil" or a "purified oil". More generally, the term "feed stream" or "feed", as described herein, may refer to a liquid that is introduced to any process unit operation described herein (e.g., an extraction unit, a refining unit, etc.).

The term "extract stream", as described herein, may generally refer to a liquid that has at least one constituent removed. The constituents removed from the extract stream may not be impurities per se. Additionally, the extract stream may not be an "impure composition" per se.

The term "raffinate stream" or "raffinate", as described herein, may generally refer to as a product of a liquid that has at least one constituent removed (e.g., an "extract stream"). For example, the "raffinate stream" or "raffinate" can be a fraction isolated from a chromatography sequence (e.g., sequential simulated moving bed chromatography (SSMB)). The raffinate stream, that liquid that has at least one constituent removed (e.g., the "extract stream"), or a combination thereof may not comprise an "impure composition". For example, each component of the "extract stream" may be isolated as a "raffinate stream" or "raffinate" as a desired product. A raffinate stream can be isolated as a mixture of any component of the extract stream at any given ratio (e.g., 90% CBD and 10% THC) or as an individual component (e.g., 100% CBD).

The term "deionize," "deionized," or "deionizing," as described herein may refer to removing at least a portion of ions from a liquid described herein. For example, at least a portion of ions can be removed from the liquid using an ion-exchange resin. The ion-exchange resin may, for example, exchange pre-loaded monovalent ions (e.g., $Na^+$, $H^+$, or a combination thereof) with divalent ions, trivalent ions, or a combination thereof, with the liquid, removing the divalent ions, trivalent ions, or a combination thereof, from the liquid and replacing the divalent ions, trivalent ions, or a combination thereof, with monovalent ions. Monovalent ions of an ion-exchange resin may be released to an organic phase, and divalent ions, trivalent ions, or a combination thereof may be sequestered to the ion-exchange resin. In some embodiments, divalent ions of a liquid are replaced with monovalent ions. In some embodiments, trivalent ions of a liquid are replaced with monovalent ions. The valency of the ion (e.g., monovalent, divalent, trivalent, etc.) may be determined by the charge of the ion. For example, $Na^+$ and $K^+$ may be monovalent cations, $Ca^{2+}$ and $Mg^{2+}$ may be divalent cations, $Al^{3+}$ and $Fe^{3+}$ may be trivalent cations, $Cl^-$ and $Br^-$ may be monovalent anions, $CO_3^{2-}$ $SO_4^{2-}$ may be divalent anions, $AsO_4^{3-}$ and $PO_4^{3-}$ may be trivalent anions.

The term "basic amino acid", as described herein, may refer to as any amino acid containing a side chain that has a pKa in water of greater than about 6 (e.g., arginine, lysine, or histidine).

The term "protamine", as used herein, may refer to an arginine rich, nuclear protein.

The term "filter aid", as used herein, may refer to a group of inert materials that can be used in filtration pretreatment. In certain embodiments, filter aids may be used to aid filtration.

The term "supercritical fluid", as described herein, may refer to any substance at a temperature and pressure above the substance's critical point (i.e., where distinct liquid and gas phase do not exist). In some embodiments, the supercritical fluid is $CO_2$.

The term "sub-critical fluid", as described herein, may refer to any substance compressed below the substance's critical temperature, wherein the substance is kept in the liquid state. In some embodiments, the sub-critical fluid is $CO_2$.

The term "stream", as described herein, may refer to a flow of solid, liquid, gas, or any combination thereof.

The term "effluent", as described herein, may refer to a solid, liquid, gas, or any combination thereof that may exit or enter a system.

The term "feeding unit" or "biomass feeding unit", as described herein, may refer to a receptacle that holds particulate matter. In some embodiments, the feeding unit can transfer the particulate matter to an extracting unit. In some embodiments, the feeding unit is equipped with a grinding unit. In some embodiments, the feeding unit is equipped with a sizing unit. In some embodiments, the feeding unit is equipped with a grinding and sizing unit. In some embodiments, the grinding unit produces biomass particulate less than about 12 mm. In some embodiments, the grinding unit produces biomass particulate less than about 6 mm.

The term "degasifier", as used herein, may refer to a unit that allows removal of, for example, gasses, water, solvent vapors, or any combination thereof that are dissolved in a liquid (e.g., an oil). For example, a degasifier can be a conical tank which is held under vacuum of about, for example, about 20 Torr, at about 120° C. The term "degas-sing", "degasify", or "degasification", as used herein, refers to the removal of dissolved gasses from liquids. For example, a degasifier can degasify a liquid.

The term "brine", as used herein, may refer to a solution of salt dissolved in water. In some embodiments, the salt may comprise Na+, K+, Li+, Cs+, or Ca2+. In some embodiments, the salt may comprise, for example, sodium chloride, sodium acetate, potassium chloride, potassium acetate, lithium chloride, lithium acetate, cesium chloride, cesium acetate, calcium chloride, calcium acetate, sodium sulfate, potassium sulfate, lithium sulfate, calcium sulfate, or any combination thereof.

When referring to the composition of a complex extract, it is useful to refer to the concentration of a specific component with reference to "Solvent Removed Base", SRB, i.e. the concentration of the specific component with respect to the total mass that is left once all solvents have been evaporated from the mass.

The term "industrial scale" or "commercial scale," as used herein, generally refers to processing biomass, or extracts thereof, at a scale that is practical for commercial use. For example, the systems and methods described herein may be capable of producing and supplying constituents derived from biomass at a scale that can provide, for example, a local supply, a national supply, or a global supply of the constituents derived from the biomass. The systems and methods described herein may process, for example, at least about 50 kilograms/day (kg/day), 100 kg/day, 250 kg/day, 500 kg/day, 1,000 kg/day, 5,000 kg/day, 10,000 kg/day, or more of biomass. The systems and methods described herein may produce, for example, 0.5 kg/day, 1 kg/day, 5 kg/day, 10 kg/day, 50 kg/day, 100 kg/day, 250 kg/day, 500 kg/day, 1,000 kg/day, or more of the constituents derived from the biomass. The term "semi-industrial scale," as described herein, generally refers to processing biomass, or extracts thereof, at a scale of less than or equal to about 1,000 kg/day, such as, for example, 1,000 kg/day, 900 kg/day, 800 kg/day, 700 kg/day, 600 kg/day, 500 kg/day, 400 kg/day, 300 kg/day, 200 kg/day, 100 kg/day, 50 kg/day, 10 kg/day, or less.

The present disclosure provides processes, methods and systems for extracting plant material. Further, the disclosure provides processes for refining crude oil to provide a least one constituent with a purity that may be sufficient for human consumption. Further, the disclosure provides processes, methods, and systems for the remediation of the purified oil to remove intoxicating compounds (e.g. THC) while minimizing loss of full spectrum of the desired constituents. Remediation is achieved by fractionating extractants from plant material into product streams enriched with at least one constituent. In some embodiments, the process comprises units that may be integrated to provide an efficient, high yielding, and well-controlled continuous process. In some embodiments, process units may be applied separately, or in combination, with different extraction or refining processes.

In some embodiments, various processes for extracting cannabinoids and terpenes may be applied, including, for example, extracting with supercritical $CO_2$ or extracting by solvent (e.g., extraction by ethanol or butane). Active substances may be extracted from plant material by a solvent, wherein the solvent may comprise a solvent or a mixture of solvents, wherein the solvent or mixture of solvents: (i) may be categorized as class 3 according to Q3C—Table and Lists Guidance for Industry (US Department of Health and Human Services, FDA, CDER, CBER), June 2017 ICH rev. 3; (ii) may form a heterogeneous azeotrope with water, wherein the solvent and the azeotrope may have a boiling point lower than the boiling point of water; and/or (iii) may form a heterogeneous azeotrope with water, wherein the solvent and the azeotrope may have a boiling point lower than the boiling point of water. In some embodiments, the ratio of water to solvent, $R_w/R_s$, may be greater in the vapor phase of the azeotrope than in the solvent liquid phase. In some embodiments, the solvent may be selected from, for example, 1-butanol, ethyl acetate, ethyl format, 2-methyl-1-butanol, ethanol, heptane, cyclohexane, 2-butanone, 2-propanol, propylene glycol, and mixtures thereof (e.g., ethyl acetate and ethyl formate).

In some embodiments, the clay may be Fuller's Earth, Kaolin clay, bentonite, diatomaceous earth, magnesium silicate (such as Florisil® or Magnesol® Polysorb) and mixtures thereof.

In some embodiments, the ion exchange resin may be, for example, a strong acid cation (SAC) resin, a weak acid cation (WAC) resin, a chelating resin, a strong base anion (SBA) resin, or a weak base anion (WBA) resin. In some embodiments, the ion exchange resin may have functional groups, for example, comprising sulfonic acid, carboxylic acid, aminophosphonic acid, Type I quaternary ammonium, quaternary ammonium, or any combination thereof. In some embodiments, the ion exchange resin may be in the form of, for example, H+, Na+, Cl−, or SO42−. In some embodiments, the ion exchange resin may comprise a resin that is, for example, agarose, cellulose, dextran, or polystyrene. In some embodiments, the ion exchange resin may be, for example, Amberjet 1600 H, PPC100H, Purolite 5950, Puromet MTS9500, Purolite 5940, Puromet MTA5012, MTA8000PPSO4, or Purolite A500.

The product obtained after extraction and after the removal of the extractant is a refined oil, comprising the target constituents, as well as many other compounds or families of compounds that are co-extracted with the target constituents. Extraction of cannabis or hemp plants can provide a refined oil comprising about 60 to 85% cannabinoids, about 2-5% terpenes and a mixture of triglycerides, free fatty acids, phospholipids, waxes and gums, and many other compounds. In some embodiments, it is important to further purify the refine oil by applying process steps for the removal of at least some waxes and gums, since they increase viscosity and adherence properties of the mixture such that it is very difficult to filter or flow. In some embodiments, it is important to remove any substances that may have adverse impact on the use of the product, such as pesticides and herbicides, aflatoxins and mycotoxins, volatile organic solvents and heavy metals. In some embodiments, the purified oil can be fractionated to enhance the concentration of a certain constituent of a group of constituents.

Furthermore, the present disclosure provides a system and process that facilitates meeting various anti-static electricity measures and other requirements of local Fire Marshal; VOC (volatile organic carbon) emissions and other EPA requirements; controls applied by BATF (Bureau of Alcohol, Tobacco and Firearms) in the case of non-denatured ethanol as a component in the solvent; the system design can meet Good Manufacturing Practice requirement as required for the production of food or drugs ingredients. In some embodiments, the system is designed with integrated process control logic to manage critical process parameters which are typically not used in batch processes; controls are monitored by a computer for process history and interlocks that minimize unsafe conditions; the system is capable of product accounting from beginning to end so is suitable for handling of restricted materials.

In some embodiments, the system is equipped with an inert gas purge, for example nitrogen, to fill the headspace of the vessels and/or equipment. In some embodiments, the purged gas from the system of integrated vessels and equipment are vented through a scrubber with a high boiling point solvent, for example cold mineral oil, that is capable of adsorbing the volatile organic compounds travelling with the gas stream. In some embodiments, the solvent is stripped of these volatiles and recycled to the scrubber. In some embodiments, the purged gas from the system of integrated vessels and equipment is incinerated in a Regenerative Thermal Oxidizer (RTO)

In certain aspects, the plant material is ground, chopped, milled, or sheared such that the average size of the resulting particles is at least about 0.01 mm, 0.1 mm, 1 mm, 10 mm, 100 mm, or 1,000 mm, or more. In some embodiments, the average size of the resulting particles is at most about 1,000 mm, 100 mm, 10 mm, 1 mm, 0.1 mm, 0.01 mm, or less. In some embodiments, the average size of the resulting particles is about 0.01 mm to about 1,000 mm, such as about 0.01 to about 100 mm, about 0.01 to about 10 mm, about 0.05 to about 8 mm, about 0.1 to about 5 mm, or about 0.5 to about 3 mm.

In some aspects, the harvested plant material is chilled prior to extraction to prevent degradation of the plant material. In some aspect, the harvested plant material is kept at a temperature above freezing to prevent cell rupture by forming water crystallites. In some embodiments, the temperature of the harvested plant material prior to extraction is controlled to be higher than about 0° C., such as higher than about 10, 20, 30, 40, or 50° C., or more. In some embodiments, the temperature of the harvested plant material is controlled to be at most about 50° C., such about 40, 35, 30, 25, 20, 15, 12, 10, 9, 8, 7, or 6° C., or less.

In some embodiments, extraction is conducted at temperature of at most about 0° C., −5° C., −10° C., −15° C., −20° C., −25° C., −35° C., −45° C., or less. In some embodiments, extraction is conducted at a temperature of at least about −45° C., −35° C., −25° C., −20° C., −15° C., −10° C., −5° C., 0° C., 10° C., 20° C., or more. In some embodiments, the extraction is conducted at about −25° C. In some embodiments, the solvent is chilled to about −25° C. prior to contacting with the plant material to provide rapid chilling of the plant material by mixing with the cold solvent. In some embodiments, the ratio of solvent to plant material is about 10:1, 15:1, 20:1, 25:1, 30:1, 35:1, 40:1 wt/wt, or more, with respect to the plant materials feed. In some embodiments, the solvent is degassed and/or purged with an inert gas.

This disclosure may be for an integrated system for extracting, refining, and remediating herbal oil (e.g., cannabis-derived oil), wherein the oil is suitable for human or animal consumption (e.g., the oil is free of toxic or intoxicating substances; it preserves the desired constituents while removing undesired ones). The integrated system can be suitable for operation under relevant industrial standards and can be economically favorable. The integrated system can comprise linked operation units for conducting different processing steps (e.g., such that the processing steps work in an orchestrated manner). The integrated system can also allow for flexibility for specific requirements (e.g., the system can: replace existing extraction operations that use a different technology, allow for further separation of specific components, or allow for tuning or control of the constituents present in the remediation product(s). PCT/US2019/043795, incorporated herein by reference, discloses processes and apparatus for extraction of substances and enriched extracts from plant material. Further improvements to processes, apparatus and system are disclosed herein.

In certain aspects, the disclosure provides a method of producing at least one plant-extracted constituent, the method comprising: (i) extracting a constituent from the plant material with a first solvent to obtain a loaded extractant; (ii) contacting the loaded extractant with an adsorbent, a desorbent, or a combination thereof to obtain a first refined extractant; (iii) concentrating the first refined extractant to obtain a first refined oil; (iv); contacting the first refined oil with at least one substance selected from the group consisting of a basic amino acid, a protamine, clay, water, brine, activated carbon, filter aid, and ion exchange resin, or a combination thereof to obtain a second refined extractant; (v) concentrating the second refined extractant to obtain a second refined oil; (vi) optionally distilling the second refined oil to obtain a purified oil; and (vii) remediating the second refined oil or the purified oil into at least one constituent to obtain at least one plant-extracted constituent. In some embodiments, the second refined oil obtained in (v) is pure enough to feed into (vii).

In certain aspects, the disclosure provides a system for producing at least one plant-extracted constituent, the method comprising: (i) extracting a constituent from the plant material with a first solvent to obtain a loaded extractant; (ii) contacting the loaded extractant with an adsorbent, a desorbent, or a combination thereof to obtain a first refined extractant; (iii) concentrating the first refined extractant to obtain a first refined oil; (iv) contacting the first refined oil with at least one substance selected from the group consisting of a basic amino acid, a protamine, clay, water, brine, activated carbon, filter aid, and ion exchange resin, or a combination thereof to obtain a second refined extractant; (v) concentrating the second refined extractant to obtain a second refined oil; (vi) optionally distilling the second refined oil to obtain a purified oil; and (vii) remediating the second refined oil or the purified oil into at least one constituent to obtain at least one plant-extracted constituent.

A schematic integrated process for providing extracted, refined, and remediated products from plant material is shown in FIG. 1. In some embodiments, the integrated process comprises an extraction unit (1000), a first refining unit (1100), and a second refining unit (1200), that receives regenerated, recycled solvent from the solvent recovery system (900). Fresh or dried plant material can be fed into the extraction unit, where the solvent extracts the plant material to provide a loaded extractant comprising plant constituents and water. Solvent can be recovered at each refining unit and transferred to recovery (900) for removal of excess water and impurities it may carry and recycling it for further use. The refined oil can be further refined at third refining (1350), to provide a purified oil. In some embodiments, prior to the third refining, the refined oil can be treated by heat, catalyst, or any combination thereof to convert carboxylic acid constituents to their respective de-carboxylated form. In some embodiments, the refined oil is treated by heat under vacuum to convert carboxylic acid constituents to their respective de-carboxylated form. In some embodiments, the purified oil can be fractionated by a chromatography process to at least two fractions, wherein one fraction is enriched with a specific constituent and the other fraction is depleted of the specific constituent. In some embodiments, the purified oil can be remediated to remove intoxicating compounds by fractionating it by a chromatography process to at least two fractions, wherein the at least one undesired compound is extracted and removed as one fraction, and the remaining purified oil is collected in a second fraction. For example, if the plant is a cannabis plant, one fraction can be enriched with THC and the other fraction can be depleted of THC. In some embodiments, a full spectrum of cannabinoids and other constituents (e.g., terpenes, fatty acids, etc.) may be present in the purified oil. The fractioned streams are recovered by evaporating or stripping the solvent(s) to provide streams of the products, these products being of high purity and a controlled composition of constituents. In some embodiments, the solvent of the solvent streams can be recovered and recycled back into the remediation system.

Figure 2A:
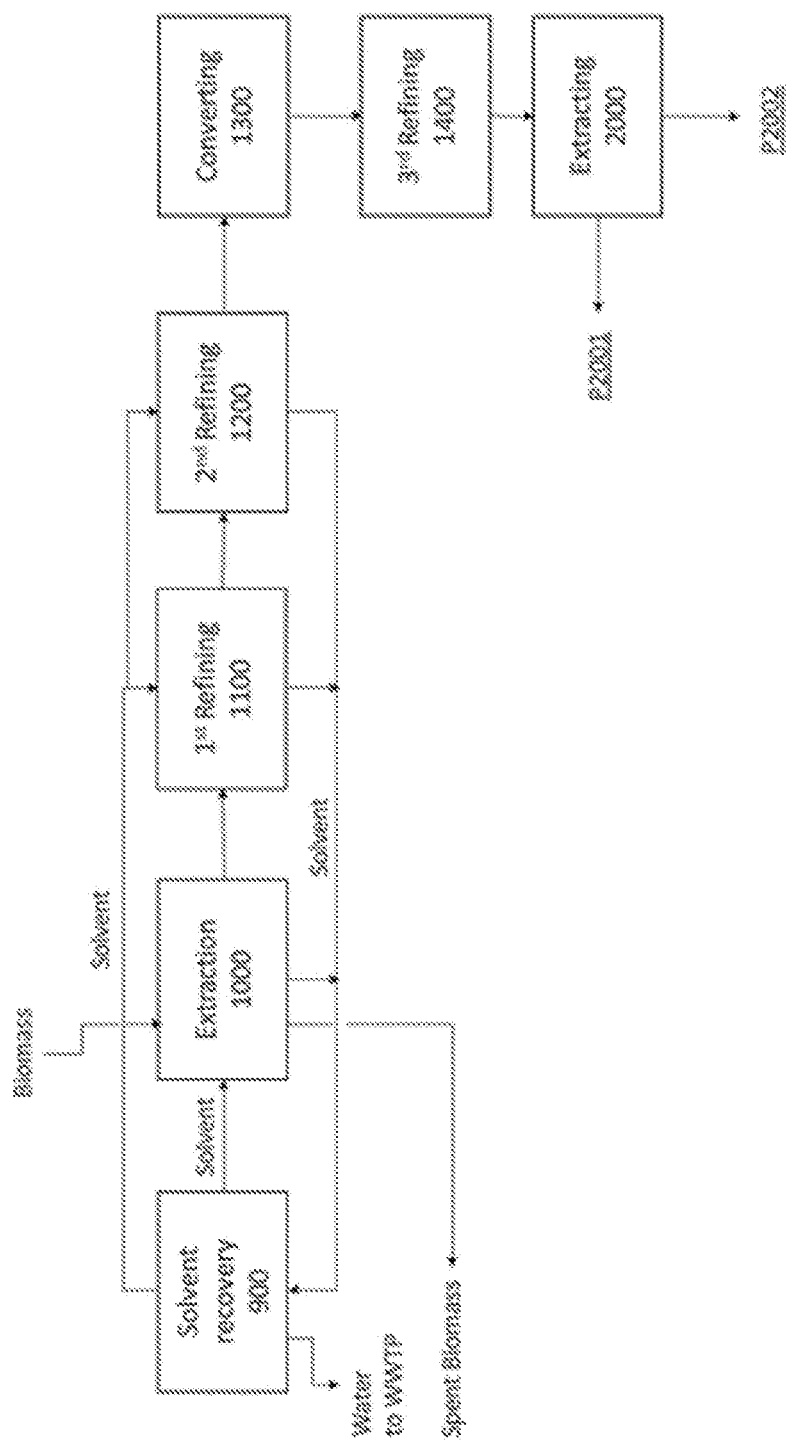
FIG. 2A illustrates an alternative schematic diagram of a modular process to extract, refine and fractionate constituents from plant material, to provide products enriched with a certain constituent or group of constituents, and to convert carboxylic acid constituents to their respective de-carboxylated constituents.

An alternative schematic integrated process for providing extracted, refined and fractionated products from plant material is shown in FIG. 2A. In some embodiments, the integrated process comprises an extraction unit (1000), a first refining unit (1100), and a second refining unit (1200), that receive regenerated, recycled solvent from the solvent recovery system (900). Fresh or dried plant material may be feed into the extraction unit, where the solvent extracts the plant material to provide a loaded extractant comprising plant constituents and water. Solvent may be recovered at each refining unit and transferred to recovery (900) for removal of excess water and impurities it may carry and recycling it for further use. The refined oil may be further refined at third refining (1300), to provide purified oil. In some embodiments, subsequent to the third refining, the refined oil may be treated by heat and/or catalyst to convert carboxylic acid constituents to their respective de-carboxylated form. In some embodiments, the refined oil may be treated by heat under vacuum to convert carboxylic acid constituents to their respective de-carboxylated form. In some embodiments, the purified oil may be fractionated by extracting with a supercritical or sub-supercritical liquid to two fractions, wherein one fraction is enriched with a specific constituent and the other fraction is depleted of the specific constituent. For example, if the plant is a cannabis plant, one fraction is enriched with THC and the other fraction is depleted of THC. In another example, the plant is a cannabis plant, one fraction is enriched with CBG or CBN and the other fraction is depleted of CBG or CBN, respectively. The extraction liquid is removed in at expansion tank, thus providing the products, these products being of high purity and a controlled composition of constituents.

Alternatively, the purified oil can be fractionated by chromatography, to provide a fraction further enhanced with one constituent. For example, if the plant is a cannabis plant, one fraction can be enriched with CBG or CBN and the other fraction can be depleted of CBG or CBN.

In some embodiments, the system and method can be designed to operate at a feed rate of at least about 50 kg/hr, 100 kg/h, 150 kg/h, 200 kg/h, 300 kg/h, 400 kg/h, 500 kg/h, 600 kg/h, 700 kg/h, 800 kg/h, 900 kg/h, 1,000 kg/h, 10,000 kg/h, or more of dried plant material. The feed rate may be of at most 10,000 kg/hr, 1,000 kg/h, 900 kg/h, 800 kg/h, 700 kg/h, 600 kg/h, 500 kg/h, 400 kg/h, 300 kg/h, 200 kg/h, 150 kg/h, 100 kg/h, 50 kg/h, or less of dried plant material. The feed rate may be from about 50 kg/hr to about 10,000 kg/h, about 100 kg/hr to about 1,000 kg/h, or about 200 kg/hr to about 500 kg/h, The plant material may comprise about 10% to about 65% liquid.

The type of product and the relative yield of each constituent may depend on the amount of each constituent present in the plant. In some embodiments, the process can yield at least 70%, 75%, 80%, 85%, 90%, 95%, 99%, or more of the major constituent present in the plant as refined oil. The major constituent may be CBD. The percentage of CBD in the refined oil may be at least about 80%, 85%, 90%, 95%, 99%, or more. In some embodiments, the plant is a *cannabis* plant, and the process can yield at least 70%, 75%, 80%, 85%, 90%, 95% of the major constituent present in the plant as refined oil. The extraction process may yield at least 70%, 80%, 90%, 95%, 99%, or more of the cannabinoids in the plant material. The refining process can recover at least about 60%, 65%, 70%, 75%, 80%, 85%, 90%, 99%, or more of the extracted cannabinoids.

Extraction Unit

Figure 3:
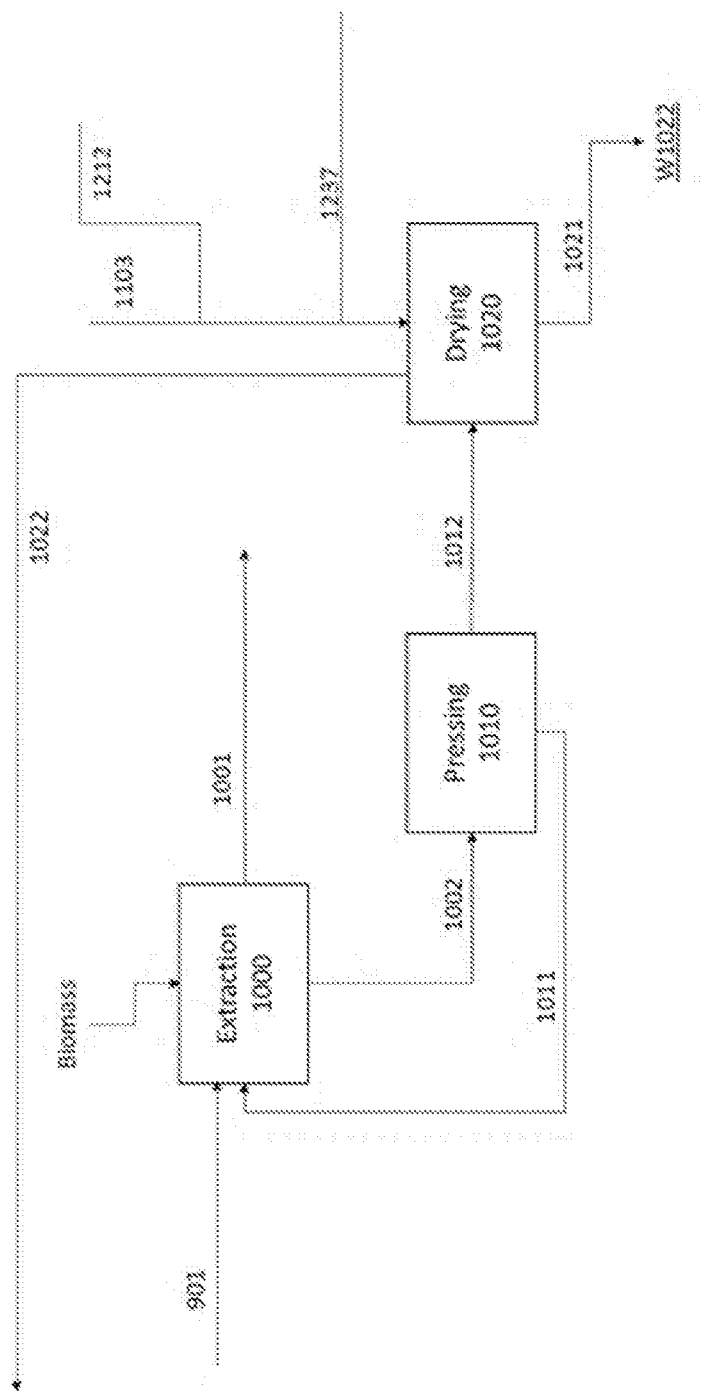
FIG. 3 illustrates a schematic diagram of a process unit for extracting plant material.

FIG. 3 shows a schematic process for extracting plant material. Plant material can be fed into the extracting system (1000), where it can be extracted with solvent that can be transferred via conduit 901 from the solvent recovery unit (900) to provide a loaded extractant stream 1001. A slurry of extracted plant material can be transferred via conduit 1002 to pressing 1010. The liquid collected by pressing can be recycled back to extracting via conduit 1011, and the pressed biomass can be transferred via conduit 1012 to a drying process (1020). The drying system 1020 can receive additional streams of moist solids from the refining units further downstream. All solids can be dried together at dryer 1020, where all vapors can be collected and returned via conduit 1022 to solvent recovery (900). The dry solids can be collected as solid waste stream 1021 and can be dispensed off according to local regulations. The loaded extractant stream 1001 can be transferred to a refining process. Streams of extracted plant material and other solids can be dried separately in two dryers. In some embodiments, the drying removes volatile solvents from the solids or the extracted plant to provide solvent-removed extracted plant material and solvent-removed solids, each one comprising less than about 0.1%, less than about 0.01% volatiles solvent. In some embodiments, the solvent-removed extracted plant material can be used as animal feed or landfill material. In some embodiments, the solvent-removed solids can be used as landfill material or as fuel.

Figure 4:
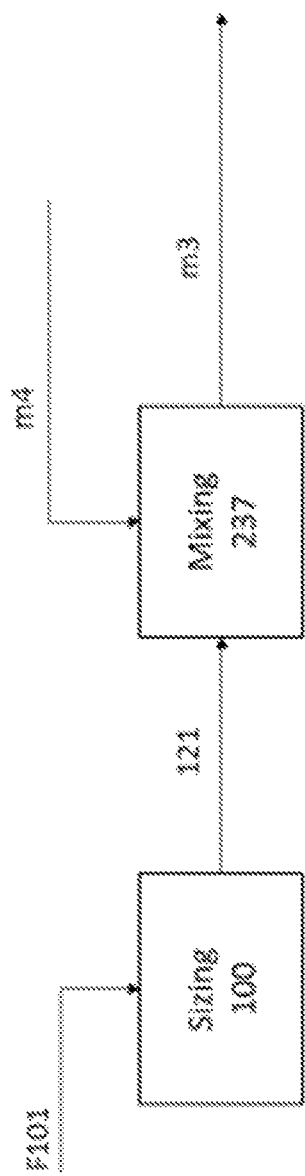
FIG. 4 illustrates a schematic diagram of a pretreating process of plant material by sizing the plant material and mixing it with a solvent or a partially loaded solvent.

In some embodiments, plant material may be pretreated prior to extraction. Pretreatment may comprise separating the different parts of the plants, e.g., buds, leaves, stalk, etc., such that each part can be treated separately. Pretreatment may comprise a reduction in plant material size (e.g. mechanical breaking, milling, grinding), or disintegrating or breaking up if the plant material is provided as pellets. In some embodiments, the plant material may be provided as green, dried, or pelletized material. In some embodiments, the green material may comprise at most about 62% moisture. Size reduction may be done on the plant material before adding a solvent, during mixing with the solvent or after adding a solvent. In some embodiments, different parts of the plant may separate at or after sizing by density. In some embodiments, sized particles of low density, e.g., a density lower than the extractant solvent density, are separated by floatation. In some embodiments, a stream of floated low-density slurry is transferred directly to pressing (1010). FIG. 4 illustrates a schematic pretreatment process, comprising a sizing operation (100) and a mixing operation (237), wherein F101 denotes the feed of plant material and 121 denotes the sized plant material stream. Stream m4, comprising partially loaded solvent (e.g. comprising some extracted constituents), transfers liquid from the extraction unit (1000) via a conduit. The slurry of plant material and solvent can be fed into extraction 1000 (FIG. 5) via conduit m3. Alternatively, stream m4 and stream 121 can be feed directly to extraction 1000 and mixed in the first extractor to contact biomass in extraction 1000.

Figure 5:
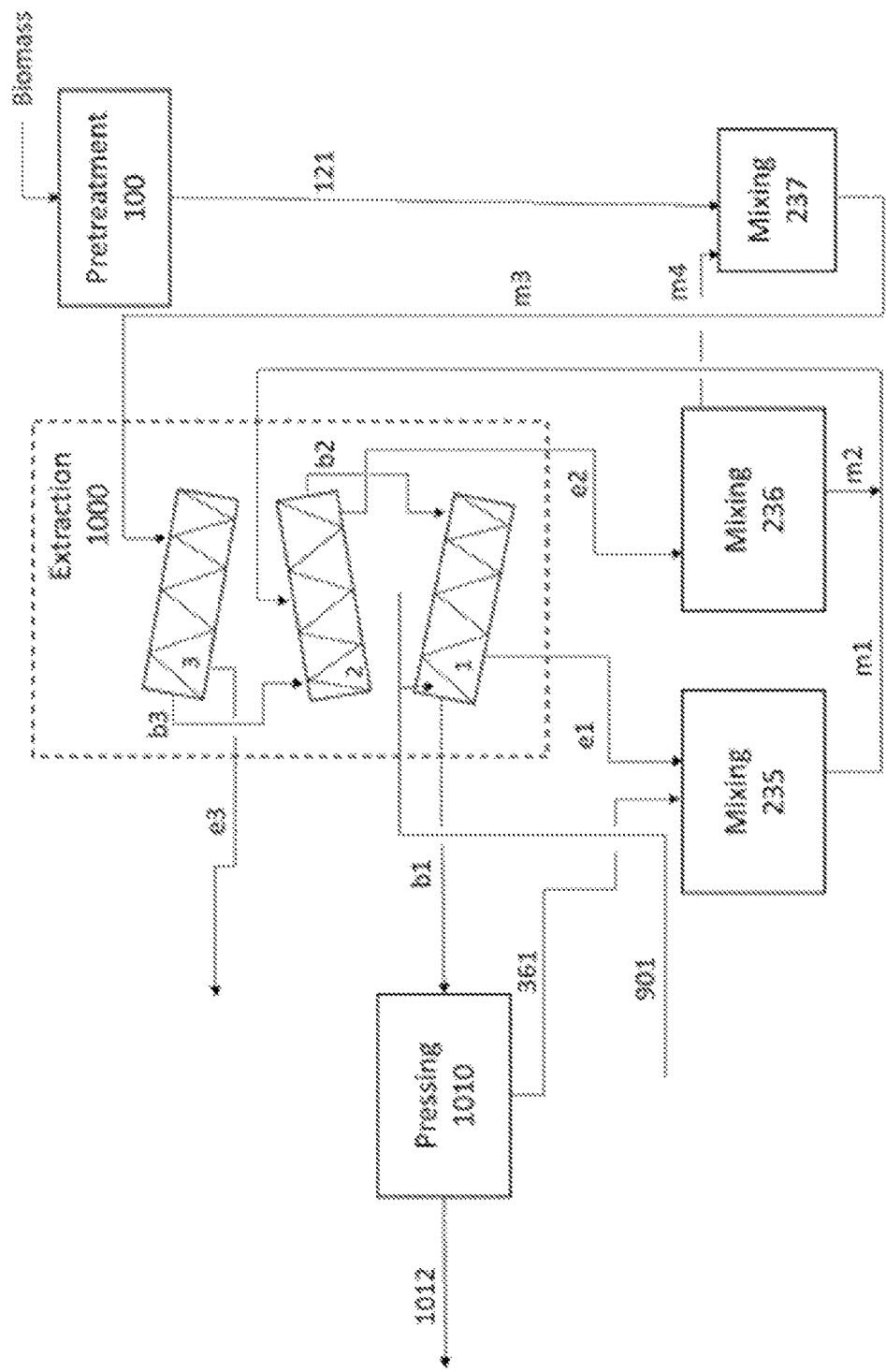
FIG. 5 illustrates a schematic diagram of a continuous process for extracting the constituents of interest from the plant material. The figure shows the configuration of an extractor comprising three extraction conveyor screw units, and three mixing units, wherein each unit operates in a co-current mode, while the flows between different units is in counter-current mode. The scheme presents three units. More units may be added in series or in parallel to any of the three conveyor screw units, to optimize extraction.

FIG. 5 illustrates extraction unit 1000 in more detail. U.S. Pat. No. 4,617,177 discloses a system for the solid/liquid extraction of in particular vegetable raw materials, such as oilseeds and oil-yielding plants, with low-boiling solvents, such as gasoline and the like, in continuous co-current manner. The equipment, which is also to be regarded as the actual extraction unit, can be formed by the combination of a conveyor screw having a screw flight pitch which widens in the direction of the transport of material, and a screen, such as wedge wire, provided at a short distance upstream of the discharge of the extracted material. The equipment can be closed on all sides and can be vapor tight. It can be employed in the solvent extraction of oilseeds and oil-yielding plants, the glyceride constituents (e.g., oils and fats) extracted from the predominantly solid raw material passing into the liquid phase, the so-called miscella. It is particularly suitable for extracting oil-yielding plants in industrial operation where the extracting solvent has a low boiling point, in the ranges of 60°-100° C. These relatively low-boiling extracting agents pose stringent requirements on the constructional expense on both the equipment and the processes. The expense relates to the safety of the maintenance and operating personnel coming into contact with the solvents and to optimum operational control, so that the extraction remains within economically acceptable limits.

Extraction unit 1000 is formed by the combination of conveyor screws and mixing tanks that provide a way to contact the pretreated biomass with the extracting solvent. The design of the system can allow for different ratios of liquid to solvent in its subunits by pumps and buffer volume in the mixing tanks. For example, FIG. 5 depicts three conveyor screw units, wherein each unit can be operated at co-current mode, while the flow of solvent and biomass can be in counter-current mode between the different units. The conveyor screws are mounted in an inclined arrangement, optionally at an angle of about 0° to about 60°, 0° to 45°, or 15° to 45°, or at about 30°. In some embodiments, a conveyor may be horizontal or partially inclined. In some embodiments, the conveyor screw may comprise a combination of screw flight pitches to mix, compress, and transport the solid material. In some embodiments, the screw flight pitch is the same along its whole length.

In some embodiments, the slurry, comprising biomass, may be flowed from one extractor to the next with gravitational force. In some embodiments, the flow of biomass slurry from the mixing tanks to the extractors may be accomplished using pumps, allowing control of flow rates. The solids discharge end of each conveyor is fitted with a wedge wire screen, allowing liquid to pass through while the slurry remains on top of the screen. The conveyors can provide solid/liquid separation at the extraction unit. The conveyor screws can be inclined at a determined angle, wherein the angle is about 0 degrees to about 45 degrees to control the residence time of material in each conveyor and screening area. A conveyor may be horizontal or partially inclined. The angle may be about 45 degrees or less.

In some embodiments, extractor 1000, mixing tanks 235, 236, 237 and other parts of the system are jacketed for thermal insulation, such that the extraction is conducted at low temperature, such as lower than about 0° C., lower than about −5° C., lower than about −10° C., lower than about −15° C., lower than about −20° C., lower than about −25° C., lower than about −35° C., lower than about −45° C., or lower. In some embodiments, the extraction is conducted at about −25° C. In some embodiments, the extraction system disclosed herein comprises a chiller (260), with capacity to cool down the freshly regenerated solvent to the designated temperature while feeding into extractor 1000(1) via conduit 261. In some embodiments, extractor 1000, mixing tanks 235, 236, 237 and other parts of the system are jacketed for thermal insulation, such that the extraction is conducted at a temperature of about 35° C. or more. In some embodiments, extractor 1000, mixing tanks 235, 236, 237 and other parts of the system are jacketed for thermal insulation, such that the extraction is conducted at a temperature of about −25° C., or less. In some aspects, extractor 1000, mixing tanks 235, 236, 237 and other parts of the system are jacketed for thermal insulation, such that the extraction is conducted at a temperature of about −25° C. (minus 25° C.) to about +35° C. (plus 35° C.), about −5° C. (minus 5° C.) to about +25° C. (plus 25° C.), or about +5° C. (plus 5° C.) to about +25° C. (plus 25° C.). In some embodiments, extraction is conducted at a temperature of about +10° C. to (plus 10° C.) to about +25° C. (plus 25° C.), or at a temperature of about +15° C. to (plus 15° C.) to about +20° C. (plus 20° C.).

Referring to FIG. 5, pre-treated biomass can be mixed in mixing tank 237 with an overflow stream of mixing tank 236 (m4) comprising partially loaded solvent, to provide slurry stream (m3), which can be fed into the uppermost conveyor, extractor 1000(3). Biomass and liquid can be conveyed up along extractor 1000(3), where the initial extraction of fresh biomass into a partially loaded extractant can occur. The loaded solvent can be separated on the screen to provide a through stream comprising the fully loaded extracted stream (e3), and a retained stream of partially extracted stream comprising biomass (b3), which can be transferred as feed to the middle conveyor, extractor 1000(2). Additional volumes of extracting solvents can be fed into extractor 1000(2) by a stream comprising low levels of extractives from mixing tank 235 (m1). In some embodiments, additional volumes of extracted solvent, comprising low levels of extractives, are feed into this stream from mixing tank 236 (m2). The extraction process may occur at extractor 1000(2); thus, it may be advantageous to have greater amounts liquid available at this stage. Biomass and liquid can be conveyed up extractor 1000(2) and can be separated to a partially loaded liquid stream (e2), which can be transferred to mixing tank 236, while the biomass comprising steam (b2) can be transferred to the lower-most conveyor, extractor 1000(1). The extracted biomass can then be washed in extractor 1000(1) that can also be fed with freshly regenerated chilled solvent (261), which may be essentially free of extractives, having a strong capacity to remove the low levels of extractives remaining with the biomass at that stage. Biomass and liquid can be conveyed up extractor 1000(1) and can be separated to a partially loaded extractant at low level of extractives (e1), which can be transferred to mixing tank 235, and a spent biomass slurry (b1), which can be transferred to solid/liquid separation 310 for recovery of the loaded solvent and drying of the spent biomass.

In some embodiments, extractor 1000(2) comprises more than one conveyor (e.g., additional conveyor(s) are arranged in parallel or in series with respect to conveyor 2 as depicted in FIG. 5. In some embodiments, the additional conveyor or conveyors are arranged in a counter-current mode with respect to conveyor 2.

In some embodiments, wetting, extraction, and solid/liquid separation in each conveyor can be controlled by physical attributes of the screw and the wire screen. In some embodiments, wet extraction and solid/liquid separation is optimized by operational parameters of the conveyor screws. In some embodiments, the inclination angle can be controlled to about 0, 10, 20, 30, 40, or 45, degrees with respect to the horizontal. In some aspect, the inclination angle can be controlled to about 45 degrees. The conveyor may be horizontal or partially inclined. In some embodiments, at the designated angle of inclination the internal conveyor volume is flooded from the leading edge of the drainage screen to the biomass inlet of the conveyor. In some embodiments, the flight pitch is the same along the conveyor. In some embodiments, the flight pitch is varied along the conveyor to optimize for initial wetting and solvent penetration in the flooded section and drainage in the screening section. In some embodiments, the rotation speed of the screw is about 0.15-20 rpm, or about 0.5 to 5 rpm, depending on the pitch of the flights. In some embodiments, the overall residence time of biomass in extractor 1000 is controlled to be about 60 minutes or more. In some embodiments, the overall residence time of biomass in extractor 1000 is controlled to be about 1 minute, or less. In some embodiments, the overall residence time of biomass in extractor 1000 is controlled to be between about 1 minute to about 60 minutes, between about 5 minutes to about 30 minutes, or between about 10 minutes to about 20 minutes.

In some embodiments, the ratio of liquid to solid in each section of extraction 1000 is different. In some embodiments, the liquid to solid (L/S) ratio in extractor 1000(1) and in extractor 1000(3) is controlled at the range from about 1 to about 50 weight parts of liquid to solid, while the L/S ratio in extractor 1000(2) is controlled at the range from about 1 to about 100 weight parts liquid to solid. In some embodiments, the liquid to solid (L/S) ratio in extractor 1000(1) and in extractor 1000(3) is controlled at the range from about 5 to about 20 weight parts of liquid to solid, while the L/S ratio in extractor 1000(2) is controlled at the range from about 20 to about 60 weight parts liquid to solid. In some embodiments, the solvent, water, or mixture thereof can be easily added into the process via fresh solvent to conveyor 1 to mixer tank 235.

In some embodiments, extraction unit 1000 is designed to extract constituents from plant material at high efficiency. In some embodiments, extraction unit 1000 is capable of extracting at least about 50%, such as at least about 60%, 70%, 80%, 90%, 95%, or more, of the amount present of each constituent in the plant material. Provided the different chemical character of multiple extracted constituents, the extraction yield can be set at different efficiency values for different components, which may allow production of variable combinations of extracted constituents. Operation parameters of the extractor can be modified to allow for optimal yields.

In some embodiments, the fully loaded extract stream (e3) comprises the liquids, due to solid/liquid separation that is performed within the conveyors. In some embodiments, the fully loaded extract stream (e3) is transferred via conduit 1001 to the first refining (1100).

In some embodiments, the extraction unit further comprises a solid/liquid separation unit comprising a press 1010 and a dryer 1020 (FIG. 3, FIG. 5). The spent biomass slurry can be transferred directly via conduit b1 (FIG. 5) to press 1010. In some embodiments, the spent biomass slurry comprises about 5-20% wt/wt solids. Press 1010 recovers loaded solvent that is transferred to mixing 235 via conduit 361, while the concentrated solids stream is transferred via 362 to drying 370. The press may be a screw press, for example, such as Vincent Corporation CP-4 press, or larger units. In some embodiments, the concentrated solids stream comprises about 35-75% wt/wt solids. The vapors released from the spent biomass at dryer 370, comprising solvent and water, can be collected, condensed in a barometric condenser, and transferred to the solvent recovery unit 900. In some embodiments, dryer 370 is a paddle dryer (e.g., GEA model Rosinaire Paddle dryer). In some embodiments, other spent solid materials used in processing and refining of the extractives, for example, use PAC or GAC, and, optionally, other adsorbent materials that may be used in refining of biomass extractives, such as clays and minerals, can be combined in the paddled dryer with the spent biomass and dried together. In some embodiments, the spent biomass and the spent solids are dried separately. In some embodiments, bottom residues of the third refining (e.g., FIG. 1 and FIG. 8), comprising a distillation process, can also be combined with either the extracted biomass or the spent solids in the dryer. In some embodiments, the dried spent solids may be used as solid fuel, animal feel, or landfill material.

The dry spent biomass (W1022) can be transferred via conduit 1021 to a solid waste treatment facility, where it can be treated according to local regulations. In some embodiments, the dry solid waste may be used for energy production. In some embodiments, the dry solid waste can be pelletized. Since the spent biomass has been effectively extracted, it may comprise trace amounts of active constituents. In some embodiments, the residual level of each constituent is less than 20% wt/wt, such as less than or equal to about 15%, 10%, 9%, 8%, 7%, 6%, 5%, 4%, 3%, 2%, 1%, or even less than or equal to about 0.1% wt/wt, of the original concentration. In some aspects, when cannabis is the plant being extracted, the residual amount of active constituents can be low enough to discard the spent biomass as unregulated dry biomass.

In some aspect, the present disclosure provides an extracted cannabis plant composition, wherein the composition comprises one or more of the following characteristics: (i) less than or equal to about 10% wt/wt dry base cannabinoids compared to the pre-extracted plant; and (ii) and less than or equal to about 0.01, 0.1, or 1% wt/wt solvent. In some embodiments, the composition comprises less than or equal to about 5% wt/wt dry base cannabinoids compared to the pre-extracted plant, such as less than or equal to about 4%, less than or equal to about 3%, less than or equal to about 2%, or less than or equal to about 1% wt/wt dry base cannabinoids.

In some embodiments, the dried solids W1022 comprises at least about 80%, or more, organic matter. In some embodiments, the organic matter can be characterized as spent biomass, comprising cellulose, hemicellulose pectin and lignin, such as comprising at least about 90% cellulose, hemicellulose, pectin and lignin, or more, in total. In some embodiments, the about 0.0001 to 1% wt/wt solvent. In some embodiments, the organic matter comprises spent PAC. In some embodiments, the organic matter comprises distillation residue comprising a high-boiling compound, such as a triglyceride, high-boiling fatty acids, fatty acid methyl esters, or any combination thereof. In some embodiments, the high boiling compounds are selected from homogeneous or heterogeneous triglycerides of at least 8 carbon atoms. In some embodiments, the fatty acids, methyl ester fatty acids, or triglycerides can comprise glycerol, oleic acid, palmitic acid, linoleic acid, linolenic acid, or derivatives thereof. The high-boiling compound may comprise a symmetrical triglyceride derived from glycerol. The high-boiling compound may comprise three units of an unsaturated fatty acid oleic acid. The high-boiling compound may comprise triolein (i.e., glyceryl trioleate). In some embodiments, the composition comprises about 0.0001% to 1% wt/wt solvent. In some embodiments, the composition comprises about 0.001 to about 5% wt/wt dry base cannabinoids, such as about 0.001 to about 1% or about 0.001 to about 0.1% wt/wt dry base cannabinoids. In some embodiments, spent process solids are dried separately from the spent biomass.

In some embodiments, the spent solids comprise spent PAC, amino acid or a protamine, and clay. The spent process solids are mixed with distillation residues comprising high boiling compound, wherein the high boiling compound is selected from homogeneous or heterogeneous triglycerides of at least 8 carbon atoms. The distillation residue may comprise residual cannabinoids and other extracted high boiling compounds.

Refining Units

In some embodiments, as biomass may be a complex composition of constituents, the target constituents, e.g., cannabinoids and terpenes, are co-extracted with lipids, phospholipids, waxes and gums, color bodies, as well as residues of pesticides and herbicides, various natural toxins, inorganic elements, including heavy metal ions. Aiming to provide a well-controlled extract, it is critical that all potentially harmful compounds are removed at least below the required regulatory concentration, and that all compounds that cause high viscosity, stickiness or any other physical property that may hinder downstream processing or adversely affect in any way the quality of the products, be removed. The relative amount of each undesired compound may change depending on growing conditions, type of the strain, season, geographic location and extraction process. It is an important aspect of the current disclosure to provide refining processes that can be successfully applied to crude products of diverse biomass feeds, extracted by different processes.

Various degumming processes for the refining of edible oils can be used, which is usually categorized as "water degumming", "acid degumming", and "enzymatic degumming". Such processes are commonly used in the production of edible oil from crude extracted oils of many grains, seeds, nuts, olives, palm fruit and so on, as well as in the biodiesel industry (Edible Oil Processing, Second Edition. Edited by Wolf Hamm, Richard J. Hamilton and Gijs Calliauw. 2013 by John Wiley & Sons, Ltd.). Crude vegetable oils obtained from either pressing or solvent extraction methods can be a complex mixture of triacylglycerols, phospholipids, sterols, tocopherols, free fatty acids, trace metals, and other minor compounds. In some embodiments, the phospholipids, free fatty acids and trace metals can be removed in order to produce a quality oil with a blend taste, light color, and a long shelf life.

The disclosure described herein provides systems and methods for the refinement of crude extracted oil when the target constituents are not the triglycerides but rather constituents, such as cannabinoids and terpenes, which are soluble in triglycerides but are different in their molecular structure and are typically more sensitive to temperature and pH conditions. Moreover, some constituents of edible oil can be removed in the refining process, e.g., some of the tocopherols (*Food Fats and Oils,* 2016 Institute of Shortening and Edible Oils); thus, the refining process can be designed to avoid losses of the target constituents. In some embodiments, as described herein, methods and processes suitable for refining the crude extract of the cannabis genre and hemp, such that phytocannabinoids, i.e. the cannabinoids as produced in the plant and extracted, are preserved to a large extent through the process and are not chemically modified or removed.

Removal of pesticides and herbicides from the extracted oil can be a challenge, and such agents may be present at trace amounts depending on the method of growth of the biomass, e.g., indoors in a shielded area or outdoors in a field, the geography, the season, neighboring fields where other crops may be grown and treated in different ways and so on. Moreover, pesticides and herbicides are organic pollutants can persist in soil in many parts of the world (A. Marican et. al., A review on pesticide removal through different processes, Environmental Science and Pollution Research (2018) 25:2051-2064), and thus may be found in growing plants even if not used at the growing season, or due to their use in neighboring fields for different crops. In some embodiments, as described herein, multiple steps for the removal of trace amounts of pesticides and herbicides can be accomplished while maintaining the level of the target constituents. In some embodiments, pesticides and herbicides may be cationic, anionic or non-ionic in nature, some may be protonated or deprotonated depending on acidity of the solution.

It may be essential to ensure removal of heavy metals to very low levels, as required by regulations already in place in some states. For example, Nevada state Division of Public and behavioral Health Policy # MME005 titled *Medical Marijuana Establishment Heavy Metals Testing Standards*, effective as of 18 Feb. 2015 requires that the limits of the following heavy metals for medical marijuana are: Arsenic less than or equal to about 0.14; Cadmium less than or equal to about 0.09; Lead less than or equal to about 0.29; Mercury less than or equal to about 0.29 µg/kg. A study by P. Atkins and J. Akers of SPEX CertiPrep, titled *Analysis of Cannabis and Hemp Products for Heavy Metals*, details the analysis of heavy metals in 18 samples of commercial oil prepared by different methods and sold in different forms in the USA. The samples can vary significantly in their profile, but most samples have been shown to contain some Arsenic, Cadmium and Lead, while Mercury was below level of detection for all but one sample. In addition, most samples contained some level of Chromium. The level measured in some of the products can be of concern if used to treat a child, having inherently lower body mass, and particularly child with health concern. Furthermore, the challenge in ensuring removal of heavy metals from cannabinoids products is aggravated by inherent properties of the plant: the cannabis genre can accumulate heavy metals and are sometimes used to reclaim contaminated soils (V. Angelova et. al., *Bioaccumulation and distribution of heavy metals in fibre crops (flax, cotton and hemp)*, Industrial Crops and Products 19(3):197-205, 2004). In some embodiments, the current disclosure provides multiple steps for the effective removal of heavy metals.

Depending on the extraction method and solvent, crude extracted product can have high viscosity at room temperature and feel "tacky". In certain embodiments, it appears as a resinous material, which can be almost solid at room temperature or may not flow well. When mixing it at a ratio of about 1:1 with a solvent, filtration can be very difficult and slow. To allow refining of the crude oil, it is essential to remove the compounds that contribute to high viscosity and "stickiness" of the crude oil, e.g. phospholipids, gums and waxes, by a "degumming" process.

In some embodiments, design of various refining steps where concentration, temperature, viscosity and flow rate to be optimal and specific for different classes of impurities, allow the construction of an integrated process for the stepwise refining of the crude extracted oil to a degree that makes plant extracted constituents suitable for human consumption.

First Refining Unit

Figure 6A:
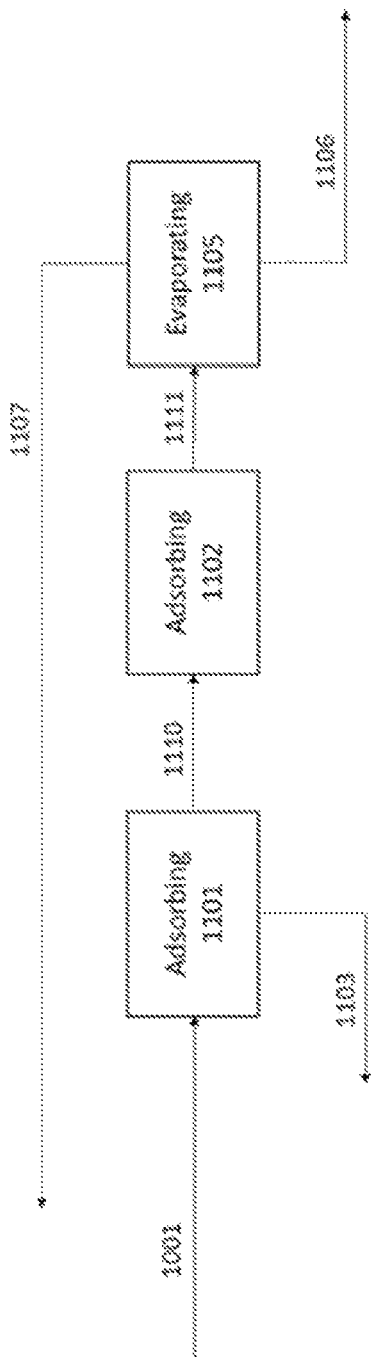
FIG. 6A illustrates a schematic diagram of a process unit for a first refining of the loaded solvent comprising extracted constituents to provide a first refined oil.

FIG. 6A, shows a schematic process for a first refining of a loaded extractant. The loaded extractant comprising solvent, water, extracted constituents, and extracted impurities, can be transferred via conduit 1001 to the first refining (1100). The first refining unit may comprise at least one adsorbing unit 1101, also, optionally, may comprise at least a second adsorbing unit 1102. The stream may then be transferred via conduit 1111 to evaporating unit 1105. Fully loaded adsorbing media can be transferred via conduit 1103 to drying (FIG. 3, 1020) or regenerated for reuse. At evaporating 1105, solvent and water are partially evaporated from the stream to provide a first refined oil, which can be transferred to the second refining unit via conduit 1006. Vapors can be collected, condensed in a barometric condenser, and transferred via conduit 1107 to solvent recovery unit 900.

Figure 6B:
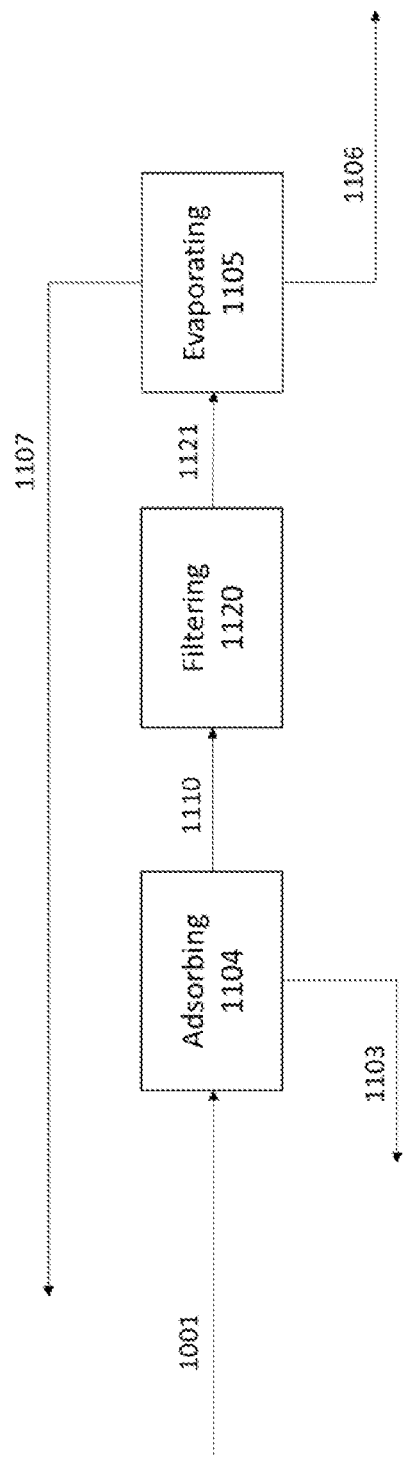
FIG. 6B illustrates an alternative schematic diagram of a process unit for a first refining of the loaded solvent comprising extracted constituents to provide a first refined oil.

When extracting thermally sensitive extractives, it is often desired to maintain a low temperature. Moreover, low temperature can provide better selection of target extractives, e.g. cannabinoids and terpenes, while minimizing extraction of undesired species, such as gums, waxes, chlorophyll, such selection is sometimes termed "winterizing". Alternatively, extraction can be performed at higher temperatures to achieve faster kinetics of extraction and higher yield, such as about −5° C. to +25° C., or even about +5° C. to +25° C., or even about +10° C. to +25° C. Such higher temperature of extraction can cause higher extraction of various undesired compounds from biomass, such as chlorophyll, color bodies, and other impurities. The additional undesired compounds can be removed from the extract by contacting the loaded solvent, comprising all extracts (i.e. target constituents and impurities), with activated carbon (e.g., PAC or GAC). In some embodiments, when the extracted plant is a cannabis plant, contact with activated carbon can also reduce the amount of THC and THCA in the extracted constituents. In some embodiments, at least 10%, 20%, 30%, 40%, 50%, or more of the THC and THCA are removed from the loaded solvent. In some embodiments, contacting is conducted by flowing the loaded solvent through at least one column packed with GAC. In some embodiments, the loaded solvent flows through at least two sequential GAC columns 1101 and 1102 (FIG. 6A). Alternatively, the loaded solvent can be contacted with PAC by flowing it through a cascade of stirred reactors 1104 (FIG. 6B) followed by filtration to remove the loaded PAC. In some embodiments, adsorbing 1104 comprises one, two, three, four, five, or more continuously stirred reactors that are connected in series to effectively mix the loaded solvent with added PAC. In some embodiments, filtering 1120 comprises a rotary vacuum filter. In some embodiments, the PAC used is a commercially available activated carbon, such carbons are available from multiple suppliers, e.g. PWA bituminous carbon or BG HHM wood char carbon from Calgon, SA-20 wood char carbon or SN-20 wood char, neutralized carbon from Nuchar.

In some embodiments, the ratio of solvent to loaded extractant in stream 1001 is about 100:1 to 1:1. In some embodiments, the ratio of solvent to crude oil in stream 1001 is about 70:1 to 20:1. In some embodiments, the ratio of solvent to crude oil in stream 1001 is about 20:1. In some embodiments, the solution is controlled to have a viscosity of about 0.5 to about 50 cPs at 25° C. In some embodiments, contacting with the GAC or PAC is done at about 50° C., or more. In some embodiments, contacting with the GAC or PAC is done at about 10° C. or less. In some embodiments, contacting with the GAC or PAC is done at about 10° C. to about 60° C., at about 30° C. to about 55° C., or at about 40° C. to about 50° C.

Solvent and water can be partially evaporated from this stream at evaporating 1105 to provide a first refined oil. In some embodiments, evaporation can be conducted at temperatures at all stages below 100° C., such as below 90° C., 80° C., 70° C., 60° C., or even below 50° C., to minimize product degradation. In some embodiments, evaporation is conducted at about 45° C. to about 50° C. In some embodiments, the ratio of solvent to oil in stream 1106 is about 12:1, or more. In some embodiments, the ratio of solvent to oil in stream 1106 is about 5:1, or less. In some embodiments, the ratio of solvent to oil in stream 1106 is about 5:1 to about 12:1, or about 6:1 to about 10:1. In some embodiments, stream 1106 comprises about 15%, or more, extracted oil. In some embodiments, stream 1106 comprises about 5%, or less, extracted oil. In some embodiments, stream 1106 comprises about 5% to about 15% extracted oil. In some embodiments, stream 1106 comprises about 30%, or more, water. In some embodiments, stream 1106 comprises about 3%, or less, water. In some embodiments, stream 1106 comprises about 90%, or more, solvent. In some embodiments, stream 1106 comprises about 60%, or less, solvent. In some embodiments, stream 1106 comprises about 3% to 30% water, and about 60% to about 95% solvent. In some embodiments, stream 1107 comprises about 0.1%, or less, oil. In some embodiments, stream 1107 comprises about 85%, or less, solvent and water. In some embodiments, stream 1107 comprises about 0.1%, or less, oil, and about 85%, or more, solvent and water.

Second Refining Unit

Figure 7:
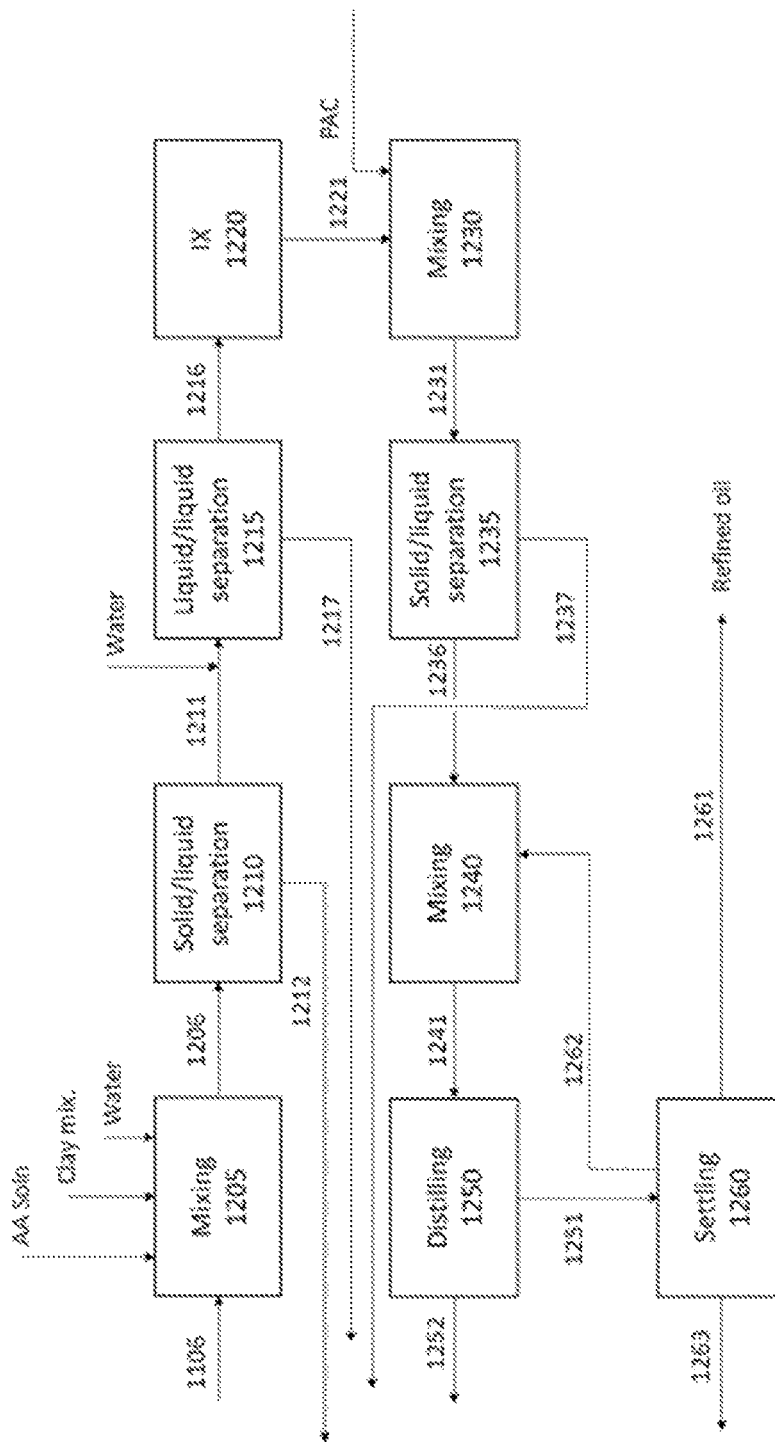
FIG. 7 illustrates a schematic diagram of a process module for a second refining of the first refined oil to provide a second refined oil.

FIG. 7 illustrates schematically a process for a second refining method, process, and system. The first refined oil can be transferred via conduit 1106 to mixing 1205. In some embodiments, mixing 1205 may be a temperature-controlled mixing tank, comprising at least one additional feeding port that facilitates dosing refining agents as solution or suspension in water and/or solvent, or as solids. In some embodiments, the temperature in mixing 1205 may be controlled to be about 10° C. to 80° C., or about 30° C. to 70° C., or about 60° C. In some embodiments, the refining agents include at least one of a basic amino acid or a solution of a protamine, at least one clay or a clay mixture, a filter aid such as diatomaceous earth, and optionally additional water. In some embodiments, prior to contacting with basic amino acid or protamine, the first refined oil is washed with water to extract flavonoids and flavonoid derivatives (e.g. aglycone flavonoids or glycoside flavonoids) into the water phase. The flavonoid can be recovered from the aqueous phase.

Basic amino acids or a protamine can form salts with certain fatty acids that have solubility in water and low solubility in certain solvents (T. H. Jukes and C. L. A. Schmidt, *The Combination of Certain Fatty Acids with Lysine, Arginine and Salmine*, J. Biol. Chem. 1935, 110). In some embodiments, this property is utilized to reduce the concentration of fatty acids present in the first refined oil by adding an aqueous solution comprising at least one of lysine, arginine or salmine, and stirring for about 2 minutes to 20 minutes, or about 10 minutes to cause the formation of a combination salt of low solubility in the mixing tank. In some embodiments, an aqueous solution comprising 1 mole lysine is added per mole fatty acid present in first refined crude oil. In some embodiments, about 0.1%, 0.2%, 0.3%, 0.4%, 0.5%, 0.6%, 0.7%, 0.8%, 0.9%, 1.0%, 1.5%, 2.0%, 2.5%, 3.0%, 4.0%, 5.0%, 6.0%, 7.0%, 8.0%, 9.0%, 10.0%, or more wt/wt lysine is added. In some embodiments, about 10.0%, 9.0%, 8.0%, 7.0%, 6.0%, 5.0%, 4.0%, 3.0%, 2.5%, 2.0%, 1.5%, 1.0%, 0.5%, 0.1%, or less wt/wt lysine is added. In some embodiments, further agents are added to mixing 1205, comprising at least one of Fuller's Earth, Kaolin clay, bentonite, diatomaceous earth, magnesium silicate (such as Florisil® or Magnesol® Polysorb) or mixtures thereof. In some embodiments, about 5% to about 20% wt/wt of a refining agent mixture is added, where the mixture comprises perlite, aluminum silicate and magnesium silicate. In some embodiments, the mixture comprises about 50% perlite, about 40% aluminum silicate and about 10% magnesium silicate. In some embodiments, the mixing is continued for about 15 minutes at about 60° C. In some embodiments, some of the impurities precipitate with the added mixture on the walls of the mixing tank. In some embodiments, additional water is added to the mixture to solubilize the precipitate, such as about 5%, 10%, 15%, 20%, 25%, 30%, 35%, 40%, or more wt/wt water/precipitate. In some embodiments, about 5% water wt/wt, or less, is added to the mixture.

In some embodiments, the solution is transferred to solid/liquid separation 1210 via conduit 1206. In some embodiments, solid/liquid separation 1210 is a filter (e.g. a rotary vacuum filter with an adjustable knife system). In some embodiments, additional water is applied to wash the solids; the additional filtrate is added to the first filtrate. In some embodiments, the added water can be about equal to the amount of water added in mixing 1205 or can be about double or about triple the amount added in mixing 1205. The liquid phase can be transferred via conduit 1211 to liquid/liquid separation 1215. In some embodiments, liquid/liquid separation is a decanting tank or centrifuge. The organic phase can be transferred via conduit 1216 for further refining, while the aqueous phase 1217 can be collected and transferred to the solvent recovery unit 900. The solids collected at the solid/liquid separation may be transferred via conduit 1212 to drying 1020 to recover the solvent.

In some embodiments, the filtrate is visually much clearer than the first refined oil. In some embodiments, at least about 50%, 60%, 70%, 80%, or more of the fatty acids are removed. In some embodiments, at most about 80%, 70%, 60%, 50%, or less of the fatty acids are removed. In some embodiments, at least about 30%, 40%, 50%, 60%, 70%, 80%, 90%, or more of sterols present in the oil are still present in the filtrate. In some embodiments, at most about 90%, 80%, 70%, 60%, 50%, 40%, 30%, or less of sterols present in the oil are still present in the filtrate. In some embodiments, additional impurities are washed out at this stage, including, for example, sugars, salts or any other water-soluble impurity.

In certain aspects, the organic phase 1216 can be contacted by an ion exchange resin, (i.e., contacting can be conducted by flowing the stream through at least one column packed with an ion exchange resin, 1220).

Some pesticides are strong or weak bases or comprise a nitrogen atom that can be protonated under acidic conditions, for example, Microbutanil, Paclobutrazol, Fenoxycarb, Befenazate, Spirotetramat, Spinosad, Imidacloprid, Thiacloprid, Spiroxamine, Propoxur, Paclobutrazol, Methyl parathion, Imazalil, Fenoxycarb, Aldicarb, Abamectin. Analytical methods for their analysis at low levels, where pre-concentration is required, utilizes the protonated nitrogen functionality for capturing them on PTFE membranes having a strong cation exchange functionality, such membranes are commercially available from 3M (Empore™ SPE).

Such compounds can be effectively removed from the solution comprising the solvent and the first refined extracted oil by weak acid cation exchange resin (WAC), which advantageously can be regenerated under milder conditions than a strong acid or base resin (SAC or SBA, respectively). When regenerating an SBA or SAC resin ensuring that no regenerating agents (e.g. strong base)

remain in the resin is difficult and costly. WAC resin can be applied for softening water, as it is effective in capturing divalent cations from aqueous solutions. WAC resins are commercially available from several suppliers, including, for example, Purolite, Dow, Sorbtech, GE and more. Contacting with a WAC resin may remove trace amounts of heavy metals. Alternatively, a SAC resin may be used to adsorb pesticides.

In some embodiments, contacting with WAC resin is performed by flowing the partially refined stream 1216 through a column packed with the resin (1220). In some embodiments, the resin is controlled to be in the $H^+$, $Na^+$, $K^+$, $Rb^+$, or $Cs^+$ form. In some embodiments, the resin is controlled to be in a mixed $Na^+$ and $H^+$ form. Two sequential columns can be used, wherein the first is in the $Na^+$ form and the second is in the form. In some embodiments, the resin is contacted at about 60° C., or more. In some embodiments, contacting with the resin is done at about 10° C. to 60° C., about at 20° C. to 50° C., about at 35° C. to 45° C. In some embodiments, the contacting with WAC resin provides the purified oil, comprising reduced amounts of pesticides and herbicides compared to the feed stream 1216. In some embodiments, about 70%, 80%, 90%, 95%, or more of the residual pesticides and herbicides present in the purified oil is removed by contacting with the WAC resin, as can be tested in stream 1216. In some embodiments, contacting with the WAC is also efficient at removing divalent or trivalent metallic cations. In some embodiments, contacting with the WAC resin efficiently removes heavy metal cations.

Referring to FIG. 7, the purified oil can be transferred to mixing 1230, where it can be contacted with PAC or with a mixture of PAC and Filter aid for polishing, by mixing for about 5 minutes to about 30 minutes, or about 10 minutes to about 20 min at temperature of about 10° C. to 60° C. In some embodiments, the mixing with PAC is for about 30 minutes, or more. In some embodiments, the mixing with PAC is for about 5 minutes, or less. In some embodiments, the mixing with PAC is at a temperature of about 60° C., or more. In some embodiments, the mixing with PAC is at a temperature of about 10° C., or less. The slurry can be transferred via conduit 1231 to solid/liquid separation 1235. The filtrate can be transferred to mixing tank 1240 via conduit 1236, the solid can be collected and transferred via conduit 1237 to the dryer, to recover the solvent. The liquid can be mixed in mixing tank with deionized water or with an aqueous salt solution and transferred via conduit 1241 to distilling 1250. The solvent can be removed by azeotropic distillation. The solvent-removed liquid, comprising refined oil and an aqueous solution, can be transferred via conduit 1251 to settling 1260. The vapors may be collected and condensed in a barometric condenser and transferred via conduit 1252 to solvent recovery 900. In some embodiments, the phases separate in settling 1260 to provide an upper phase comprising the refined oil and a bottom phase comprising the aqueous solution. The refined oil can be transferred via conduit 1261 to converting 1300. The aqueous solution may be recycled back into mixing 1240. The aqueous solution may comprise a salt such as, for example, sodium chloride, sodium acetate, or sodium formate. In some embodiments, the salt comprises sodium acetate.

A high-boiling compound can be added to the azeotropic distillation feed, wherein the high-boiling compound is a food grade compound. The high-boiling compound may be characterized to: (i) have a density of about 0.8 $g/cm^3$ to about 1.10 $g/cm^3$, or about 0.95 $g/cm^3$; (ii) have a boiling point greater than about 200° C., 250° C., 300° C., 350° C., 400° C., 450° C., or more at 60 torr; (iii) have a viscosity of less than 30 cStokes, 20 cStokes, 15 cStokes, or less at 90° C.; (iv) be miscible with the refined oil; or any combination thereof. The high-boiling compound may be characterized to: (i) have a density of about 0.8 $g/cm^3$ to about 1.10 $g/cm^3$, or about 0.95 $g/cm^3$; (ii) have a boiling point greater than about 200° C., 250° C., 300° C., 350° C., 400° C., 450° C., or more at 60 torr; (iii) have a viscosity of less than 30 cStokes, 20 cStokes, 15 cStokes, or less at 90° C.; and, (iv) be miscible with the refined oil. The high-boiling compound may be a fatty acid or a methyl ester fatty acid. In some embodiments, the high-boiling compound is a triglyceride. In some embodiments, the high boiling compounds are selected from homogeneous or heterogeneous fatty acids of at least 8 carbon atoms. In some embodiments, the fatty acids or methyl ester fatty acids comprise oleic acid, palmitic acid, linoleic acid or linolenic acid, or mixtures thereof. In some embodiments, a refined extract of a cannabis plant can have a percentage of active constituents that is at least about 80%, 85%, 90%, 95%, 99%, or more. In some embodiments, a refined extract of a cannabis plant can have a percentage of active constituents that is at most about 99%, 95%, 90%, 85%, 80%, or more. In some embodiments, a refined extract of a cannabis plant can have a percentage of active constituents that is from about 80% to about 99%, about 90% to about 99%, about 95% to about 99%. The refined extract may be fed to the remediation step of (vii).

Third Refining Unit

Figure 8:
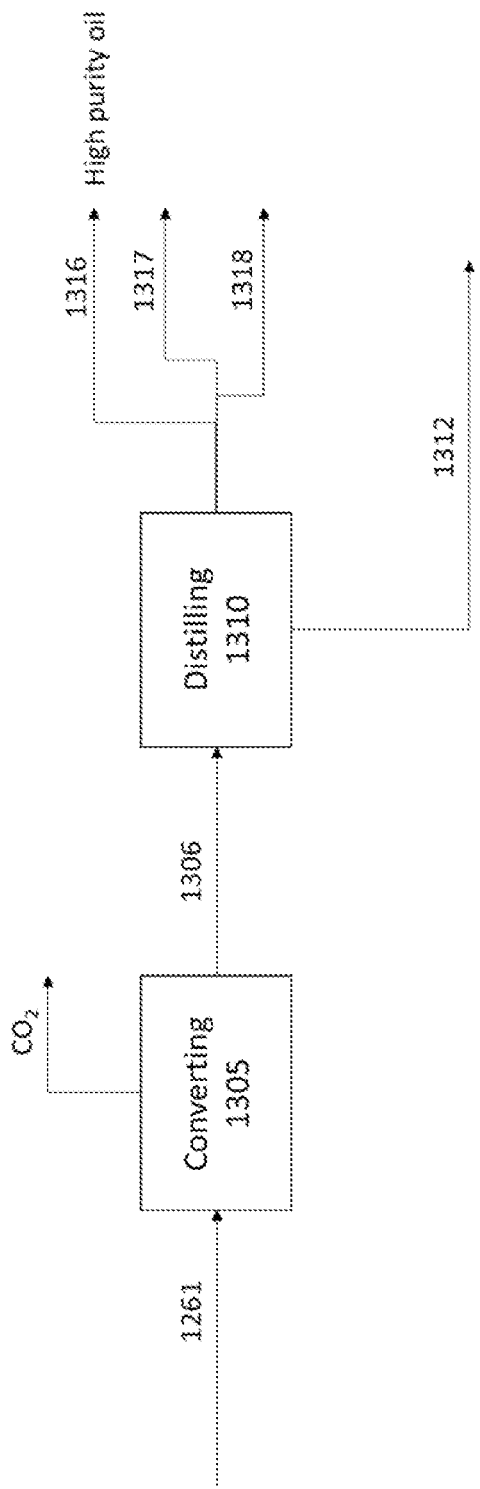
FIG. 8 illustrates a schematic diagram of a process unit for converting carboxylic acid constituents to their de-carboxylated constituents and further refining in a third refining unit to provide a purified oil.

FIG. 8 illustrates schematically a process for a third refining method, process and system. The second refined oil may be transferred via conduit 1261 to converting 1305, wherein carboxylic acid constituents can be converted to their de-carboxylated constituents. In some embodiments, the refined oil is heated to about 150° C. or more. In some embodiments, the refined oil is heated to about 45° C. or less. In some embodiments, the refined oil is heated from about 45° C. to about 170° C., or from about 130° C. to about 160° C. for 0.5 to 4 h. In some embodiments, heating is conducted under vacuum. In some embodiments, 95% or less of carboxylic acid constituents are converted to their respective de-carboxylated constituents. In some embodiments, at least about 95%, 96%, 97%, 98%, 99%, or more of carboxylic acid constituents are converted to their respective de-carboxylated constituents. In some embodiments, less than 2%, 1%, 0.5%, 0.2%, or even less than 0.1% of the constituents are present in carboxylated form. In some embodiments, when the extracted plant is a cannabis plant, at least some of the THC and THCA present in the refined oil is oxidized to CBN. In some embodiments, at least 10%, 20%, 30%, 40%, 50% of the THC/THCA present in the oil is oxidized to CBN. The de-carboxylated purified oil can be transferred via conduit 1306 to distilling 1310.

Distilling 1310 may comprise a short path distillation. In some embodiments, distilling 1310 comprises a wiped film distillation system. Such systems are commercially available from multiple suppliers at all scales from lab to industrial, for example Pope Scientific Inc., Root Sciences, UIC GmbH and others. In some embodiments, the distillation temperature is at least about 100° C., 150° C., 200° C., 250° C., 300° C., 350° C., 400° C., or more. In some embodiments, the distillation temperature is at most about 400° C., 350° C., 300° C., 250° C., 200° C., 150° C., 100° C., or less. In some embodiments, the distillation temperature is about 100° C. to about 400° C., about 100° C. to about 250° C., or about 150° C. to about 200° C. In some embodiments, the distillation pressure is at most about 500 Torr, 450 Torr, 400 Torr, 350 Torr, 300 Torr, 250 Torr, 200 Torr, 150 Torr, 100 Torr, 50 Torr, 10 Torr, about 1 Torr, or less. In some embodiments, the distillation pressure is at least about 1 Torr, 10 Torr, 50 Torr, 100 Torr, 150 Torr, 200 Torr, 250 Torr, 300 Torr, 350 Torr, 400 Torr, 450 Torr, about 500 Torr, or more. In some embodiments, the distillation pressure is from about 500 Torr to about 1 Torr, about 250 Torr to about 1 Torr, or about 100 Torr to about 1 Torr. In some embodiments, the distillation pressure is from about 0.01 Torr to about 450 Torr. In some embodiments, the temperature is about 150° C. to about 200° C. and the pressure is less than 5 Torr, less than 1 Torr, or less. In some embodiments, the temperature is initially about 130° C. to about 140° C. and the pressure is about 3000 mTorr to about 100 mTorr and is then about 160° C. to about 180° C. and the pressure is about 80 mTorr or about 60-65 mTorr.

In some embodiments, a high-boiling compound is added to the distillation feed wherein the compound is a food grade compound. The high-boiling compound may be characterized to: (i) have a density of about 0.8 $g/cm^3$ to about 1.10 $g/cm^3$, or about 0.95 $g/cm^3$; (ii) have a boiling point greater than about 200° C., 250° C., 300° C., 350° C., 400° C., 450° C., ore more at 60 torr; (iii) have a viscosity of less than 30 cStokes, 20 cStokes, 15 cStokes, or less at 90° C.; or, (iv) be miscible with the refined oil. The high-boiling compound may be characterized to: (i) have a density of about 0.8 $g/cm^3$ to about 1.10 $g/cm^3$, or about 0.95 $g/cm^3$; (ii) have a boiling point greater than about 200° C., 250° C., 300° C., 350° C., 400° C., 450° C., or more at 60 torr; (iii) have a viscosity of less than 30 cStokes, 20 cStokes, 15 cStokes, or less at 90° C.; and, (iv) be miscible with the refined oil. The high-boiling compound may be a fatty acid or a methyl ester fatty acid. In some embodiments, the high-boiling compound is a triglyceride. In some embodiments, the high boiling compounds are selected from homogeneous or heterogeneous fatty acids of at least 8 carbon atoms. In some embodiments, the fatty acids or methyl ester fatty acids comprise oleic acid, palmitic acid, linoleic acid or linolenic acid, or mixtures thereof. In some embodiments, at least about 1, 2, 3, 4, or more fractions are collected. In some embodiments, a first fraction comprises monoterpenes hydrocarbons and oxygenated monoterpenes (e.g., α-pinene, myrcene and terpinolene); a second fraction comprises Sesquiterpene hydrocarbons, Oxygenated sesquiterpenes (e.g., (E)-caryophyllene, α-humulene and caryophyllene oxide); a third fraction comprises cannabinoids and residual fatty acids. In some aspects, the purified oil is transferred via conduit 1316 to extracting fractionating 1400 (FIG. 1). In some embodiments, the bottom residue is transferred via conduit 1312 to drying 1020 (FIG. 3). In some embodiments, additives such as acids, medium chain triglycerides, propylene glycol, and vegetable glycerine can be added to the purified oil to inhibit crystallization.

Supercritical Extracting Unit

Supercritical $CO_2$ can extract constituents from plant materials. For example, J. M Prado et. al., J. Supercritical Fluids, 2011, 56, 231, show extraction of sugarcane and clove with supercritical $CO_2$. H. PERROTIN-BRUNEL *Sustainable Production of Cannabinoids with Supercritical $CO_2$ Technologies*, PhD Thesis submitted to the Technische Universiteit Delft in April 2011 teaches the different solubilities of different cannabinoid constituents in supercritical $CO_2$. L. J. Rovetto and N. V. Aieta, J. Supercritical Fluids, 2017, 129, 16 demonstrate higher efficiency of cannabinoid extraction by adding pulses of ethanol to the supercritical $CO_2$. However, these earlier publications utilize supercritical $CO_2$ to extract constituents from the plant material, and struggle with solubility limitations in the supercritical fluid of various constituents, as well as kinetics of diffusion of the extracting fluid into the plant compartments or cells. For extraction systems that utilize sub-supercritical or supercritical $CO_2$, there may be a tradeoff between capacity and speed to purity, and most use hybrid systems that require additional purification steps, for example, by ethanol winterization and further refining. One of the challenges of supercritical extraction can be handling of a fibrous plant material, in addition to limited solubility of some constituents and slow kinetics at low temperatures, which may be sometimes applied to reduce co-extraction of impurities.

In contrast to the above, we realized that the difference in solubility in $CO_2$ of extracted plant constituents, and in particularly the difference in solubility of cannabinoid constituents, can be utilized for fractionating purified oil to a fraction which is depleted of THC and a fraction that is enriched in THC. In some aspects, control of the ratio of supercritical $CO_2$ to purified oil, temperature and pressure provide multiple products, such as THC-free oil, high THC oil, high CBD oil, high CBN oil, and full spectrum oils, comprising multiple cannabinoids at different desired ratios. Control of these parameters may allow maintaining products at high yield with minimal cannabinoids loss.

Figure 9:
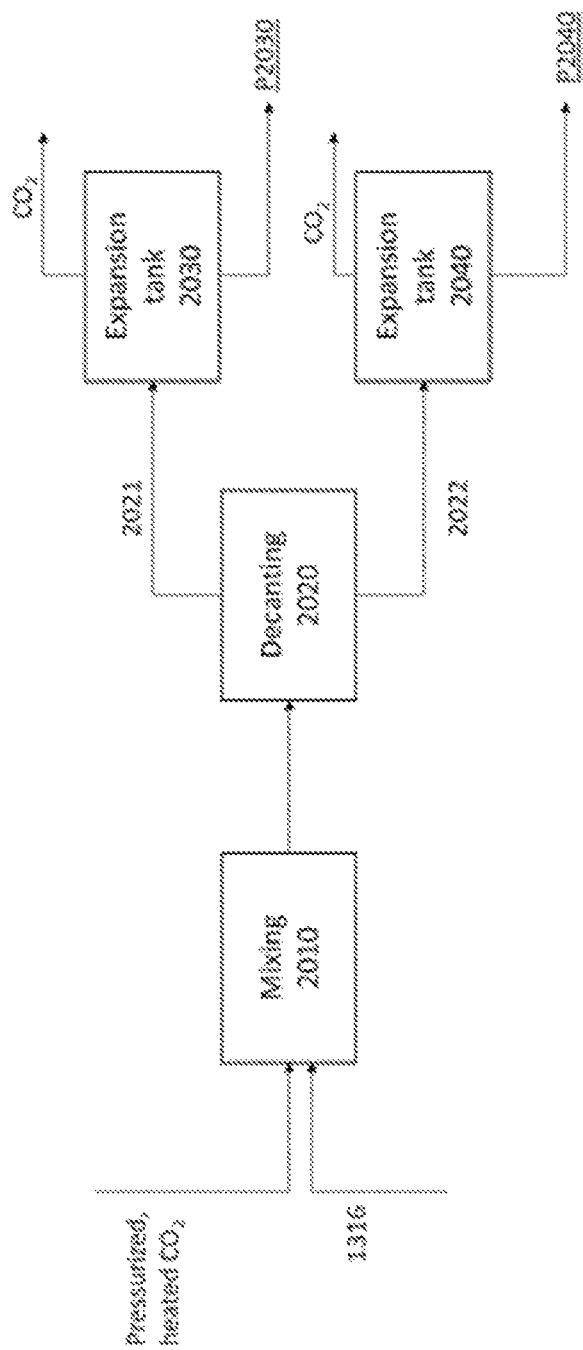
FIG. 9 illustrates a schematic diagram for a process unit for extracting the purified oil with supercritical liquid.

Referring to FIG. 9, the purified oil 1316 may be mixed with supercritical $CO_2$ in mixing 2010. In some embodiments, mixing 2010 is a static mixer or a mixing tank. The mixture can be fed into a high-pressure separation tank, wherein the mixture separates to an upper phase and a bottom phase. In some aspects, the upper phase comprises supercritical $CO_2$ extractant loaded with the more soluble cannabinoids. In some aspects, the bottom phase comprises purified oil of lower solubility cannabinoids and $CO_2$. The upper phase may be transferred via conduit 2021 to expansion tank 2030, wherein $CO_2$ is released as gas to provide a purified oil product P2030, enriched with THC. The bottom phase can be transferred via conduit 2022 to expansion tank 2040, wherein $CO_2$ is released as gas to provide a purified oil product P2040, depleted of THC. In some embodiments, the pressure of the supercritical $CO_2$ is fed at a pressure of more than or equal to about 1, 2, 3, 4, 5, 6, 7, 8, 9, 10, 11, 12, 13, 14, 15, 16, 17, 18, 19, 20, 21, 22, 23, 24, 25, 30, 40, 50, 60, 70, 80, 90, 100 MPa, or more. In some embodiments, the pressure of the supercritical $CO_2$ is fed at a pressure of less than or equal to about 100, 90, 70, 60, 50, 40, 30, 25, 20, 15, 10, 5 MPa, or less. In some embodiments, the pressure of the supercritical $CO_2$ is fed at a pressure from about 1 MPa to about 100 MPa. In some embodiments, the supercritical $CO_2$ is fed at a pressure of about 10 to 25 mPa. In some embodiments, the supercritical $CO_2$ is fed at temperature of less than or equal to about 400, 390, 380, 370, 360, 350, 340, 330, 320, 310, 300 K, or less. In some embodiments, the supercritical $CO_2$ is fed at temperature of more than or equal to about 300, 310, 320, 330, 340, 350, 360, 370, 380, 390, 400 K, or more. In some embodiments, the supercritical $CO_2$ is fed at temperature of about 300 K to about 400 K. In some embodiments, the supercritical $CO_2$ is fed at temperature of about 310 K to 335 K. In some embodiments, more than or equal to about 150, 200, 300, 400, 500, 600, 700, 800, 900, 1000, 2000, 3000, 4000, 5000, 6000, 7000, 8000, 9000, or more unit mass $CO_2$ are provided per unit mass of THC present in the purified oil. In some embodiments, less than or equal to about 9000, 8000, 7000, 6000, 5000, 4000, 3000, 2000, 1000, 900, 800, 700, 600, 500, 400, 300, 200, 100, or less unit mass $CO_2$ are provided per unit mass of THC present in the purified oil. In some aspects, about 2000 to about 8000 unit mass of $CO_2$ are provided per unit mass of THC present in the purified oil stream 1316.

Figure 10:
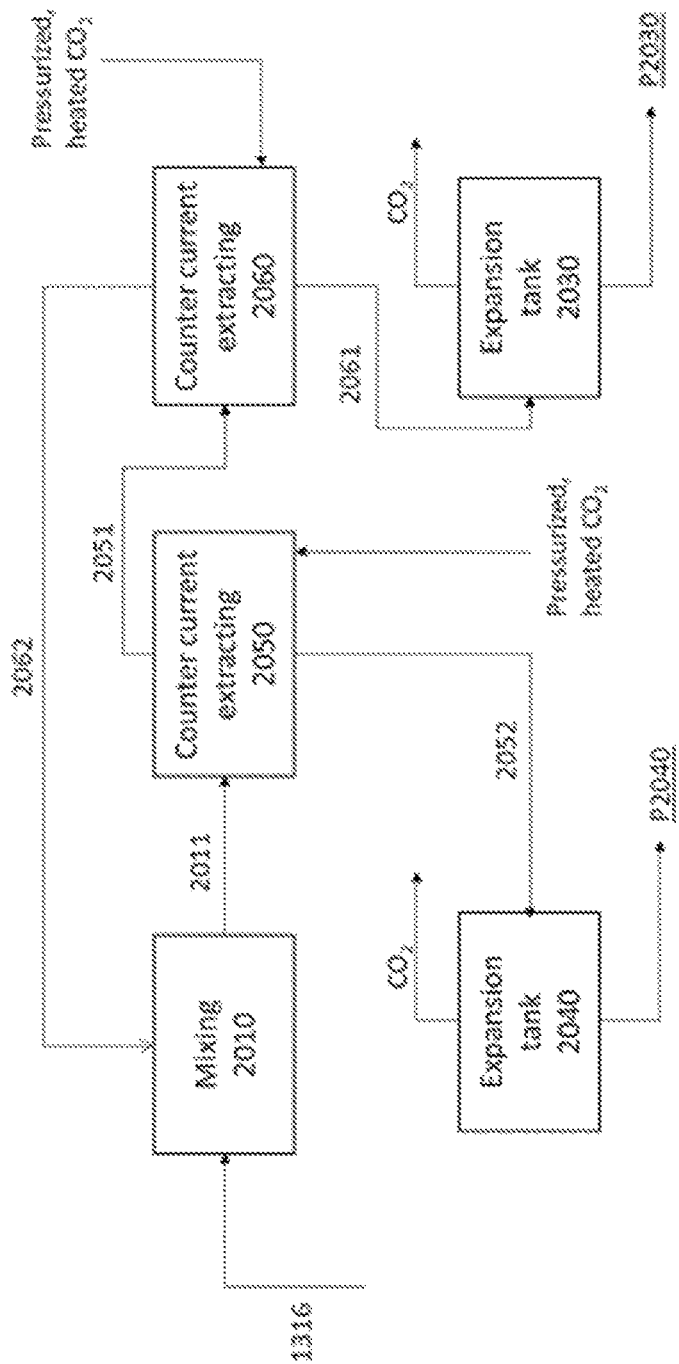
FIG. 10 illustrates an alternative schematic diagram for a process unit for extracting the purified oil with supercritical liquid.

In some embodiments, the purified oil 1316 is contacted with supercritical $CO_2$ in at least one counter current extraction column (FIG. 10), having at least one, two or at least 3 stages, wherein each stage may be held at different temperature. In some aspects, supercritical $CO_2$ is fed through the bottom inlet of the column, while the purified oil is feed through the top inlet of the column. The two phases can be effectively mixed and separated within the extraction column to provide an effluent of loaded supercritical $CO_2$ at the top outlet, comprising the THC-enriched stream, and an effluent of THC-depleted stream and the bottom outlet. 10 illustrates a process of counter current extracting of high purity cannabis oil with supercritical $CO_2$. Stream 1316, comprising purified oil, can be mixed in mixing 2010 with returning stream 2062, comprising supercritical $CO_2$ and residual amounts of cannabinoids. The mixture may be fed to the top of a counter current column extractor 2050. In some embodiments, the pressure of the supercritical $CO_2$ in the column is more than or equal to about 1, 2, 3, 4, 5, 6, 7, 8, 9, 10, 11, 12, 13, 14, 15, 16, 17, 18, 19, 20, 21, 22, 23, 24, 25, 30, 40, 50, 60, 70, 80, 90, 100 MPa, or more. In some embodiments, the pressure of the supercritical $CO_2$ in the column is less than or equal to about 100, 90, 80, 70, 60, 50, 40, 30, 25, 20, 15, 10, 5, MPa, or less, In some embodiments, the pressure of the supercritical $CO_2$ in the column is from about 1 MPa to about 100 MPa. In some aspects, the pressure of the supercritical $CO_2$ in the column is about 15, 16, 17, 18, 19, 20, 21, 22, 23, 24, 25 MPa. In some embodiments, the temperature is more than or equal to about 20, 30, 40, 50, 55, 56, 57, 58, 59, 60, 61, 62, 63, 64, 65, 66, 70, 75, 80, 90, 100° C., or more at the bottom of the column. In some embodiments, the temperature is less than or equal to about 100, 90, 80, 70, 65, 60, 55, 50, 45, 40, 35, 30, 25, 20° C., or less at the bottom of the column. In some embodiments, the temperature is from about 20° C. to about 100° C. at the bottom of the column. In some embodiments, the temperature is about 55, 56, 57, 58, 59, 60, 61, 62, 63, 64, 65, 66° C. at the bottom of the column. In some embodiments, the temperature is more than or equal to about 20, 30, 40, 50, 55, 56, 57, 58, 59, 60, 61, 62, 63, 64, 65, 66, 70, 75, 80, 90, 100° C., or more at the top of the column. In some embodiments, the temperature is less than or equal to about 100, 90, 80, 70, 65, 60, 55, 50, 45, 40, 35, 30, 25, 20° C., or less at the top of the column. In some embodiments, the temperature is from about 20° C. to about 100° C., at the top of the column. In some embodiments, the temperature is from about 35, 36, 37, 38, 39, 40, 41, 42, 43, 44, 45, 46° C. at the top of the column. In some embodiments, more than or equal to about 150, 200, 300, 400, 500, 600, 700, 800, 900, 1000, 2000, 3000, 4000, 5000, 6000, or more unit mass $CO_2$ are provided with respect to THC unit mass. In some embodiments, less than or equal to about 6000, 5000, 4000, 3000, 2000, 1000, 900, 800, 700, 600, 500, 400, 300, 200, 150, or less unit mass $CO_2$ are provided with respect to THC unit mass. In some aspects, about 2000 to about 6000 unit mass $CO_2$ are provided with respect to THC unit mass. In some embodiments, more than or equal to about 30, 40, 50, 60, 70, 80, 90, 100, 200, 300, 400, 500, 600, or more unit mass $CO_2$ are provided with respect to total cannabinoids unit mass. In some embodiments, less than or equal to about 600, 500, 400, 300, 200, 100, 90, 80, 70, 60, 50, 40, 30, or less unit mass $CO_2$ are provided with respect to total cannabinoids unit mass. In some embodiments, about 20 to about 300 unit mass $CO_2$ is provided with respect to total cannabinoids unit mass. In some aspects, the bottom effluent of the extractor is transferred via conduit 2052 to expansion tank 2040, where $CO_2$ is released as gas. In some aspects, stream 2052 comprises less than 0.001% THC. In some aspects, the yield of CBD in stream 2052 is at least 70, 75, 80, 85, 90, 95, 96, 97, 98, 99%, or more of the CBD in stream 1316. In some aspects, the yield of CBD in stream 2052 is at most 99, 95, 90, 85, 80, 75, 70%, or less of the CBD in stream 1316.

The top effluent of the column can be transferred via conduit 2051 to a second counter current column extractor 2060. In some embodiments, an additional amount of supercritical $CO_2$ is fed into extractor 2060. In some embodiments, the pressure of the supercritical $CO_2$ in the column is more than or equal to about 1, 2, 3, 4, 5, 6, 7, 8, 9, 10, 11, 12, 13, 14, 15, 16, 17, 18, 19, 20, 21, 22, 23, 24, 25, 30, 40, 50, 60, 70, 80, 90, 100 MPa, or more. In some embodiments, the pressure of the supercritical $CO_2$ in the column is less than or equal to about 100, 90, 70, 60, 50, 40, 30, 25, 20, 15, 10, 5 MPa, or less. In some embodiments, the pressure of the supercritical $CO_2$ in the column is from about 1 MPa to about 100 MPa. In some embodiments, the pressure of the supercritical $CO_2$ in the column is about 5, 6, 7, 8, 9, 10, 11, 12, 13, 14, 15, 16, 17, 18, 19, or 20 MPa. In some embodiments, the temperature is more than or equal to about 20, 30, 40, 50, 55, 56, 57, 58, 59, 60, 61, 62, 63, 64, 65, 66, 70, 75, 80, 90, 100° C., or more at the bottom of the column. In some embodiments, the temperature is less than or equal to about 100, 90, 80, 70, 65, 60, 55, 50, 45, 40, 35, 30, 25, 20° C., or less at the bottom of the column. In some embodiments, the temperature is from about 20° C. to about 100° C. at the bottom of the column. In some embodiments, the temperature is about 50, 55, 56, 57, 58, 59, 60, 61, 62, 63, 64, 65, 66, 67, 68, 69, or 70° C. at the bottom of the column. In some embodiments, the temperature is more than or equal to about 20, 30, 40, 50, 55, 56, 57, 58, 59, 60, 61, 62, 63, 64, 65, 66, 70, 75, 80, 90, 100° C., or more at the top of the column. In some embodiments, the temperature is less than or equal to about 100, 90, 80, 70, 65, 60, 55, 50, 45, 40, 35, 30, 25, 20° C., or less at the top of the column. In some embodiments, the temperature is from about 20° C. to about 100° C. at the top of the column. In some embodiments, the temperature is about 20, 30, 40, 50, 55, 56, 57, 58, 59, 60, 61, 62, 63, 64, 65, 66, 70, 75, 80, 90, 100° C., at the top of the column. In some embodiments, the temperature is from about 35, 36, 37, 38, 39, 40, 41, 42, 43, 44, 45, 46° C. at the top of the column. In some embodiments, more than or equal to about 150, 200, 300, 400, 500, 600, 700, 800, 900, 1000, 2000, 3000, 4000, 5000, 6000, or more unit mass $CO_2$ are provided with respect to THC unit mass. In some embodiments, less than or equal to about 6000, 5000, 4000, 3000, 2000, 1000, 900, 800, 700, 600, 500, 400, 300, 200, 150, or less unit mass $CO_2$ are provided with respect to THC unit mass. In some aspects, about 150 to about 6000 unit mass $CO_2$ are provided with respect to THC unit mass. In some embodiments, about 30, 40, 50, 60, 70, 80, 90, 100, 200, 300, 400, 500, 600, or more unit mass $CO_2$ are provided with respect to total cannabinoids unit mass. In some embodiments, less than or equal to about 600, 500, 400, 300, 200, 100, 90, 80, 70, 60, 50, 40, 30, or less unit mass $CO_2$ are provided with respect to total cannabinoids unit mass. In some embodiments, about 30 to about 600 unit mass $CO_2$ are provided with respect to total cannabinoids unit mass. In some aspects, the bottom effluent of the extractor is transferred via conduit 2061 to expansion tank 2030, where $CO_2$ is released as gas. In some aspects, stream 2016 comprises at least about 25, 30, 40, 50, 60, 70% wt/wt, or more THC with respect to total cannabinoids. In some aspects, stream 2016 comprises at most about 70, 60, 50, 40, 30, 25% wt/wt, or less THC with respect to total cannabinoids. The top effluent of extractor 2060 is transferred via conduit 2062 back to mixing for further extracting. In some embodiments, stream 2061 can be further fractionated by supercritical extraction or by chromatography to further enrich the THC concentration, or to fractionate a minor cannabinoid. In some embodiments, the THC-enriched product P2030 comprises at least about 50%, 60%, 70%, 80%, 90%, 95%, or more of the THC present in the purified oil. In some embodiments, the THC-enriched product P2030 comprises at least about 95% of the THC present in the purified oil. In some embodiments, the THC-enriched product P2030 comprises at least about 99% of the THC present in the purified oil. In some embodiments, the THC enriched product P2030 comprises at least about 99.9% of the THC present in the purified oil. In some embodiments, the THC-enriched product P2030 comprises about 25%, or less, of the CBD present in the purified oil. In some embodiments, the THC-enriched product P2030 comprises about 15%, or less, of the CBD present in the purified oil. In some embodiments, the THC-enriched product P2030 comprises about 5%, or less, of the CBD present in the purified oil. In some embodiments, the THC-depleted product P2040 comprises about 0.300%, or less, THC. In some embodiments, the THC-depleted product P2040 comprises about 0.001%, or less, THC.

Solvent Recovery and Recycling Unit and Systems

In some embodiments, full recovery and recycling of solvent used in the extraction and refining methods and processes is accomplished. In some embodiments, the system is designed such that all vapors are collected from all process stages where vapors are generated in an evaporation, drying or distillation process. In some aspects, the system is further designed to condense vapor in a simple set up at minimal energy requirements by employing barometric condenser systems, also referred to as atmospheric evaporators, at all relevant stages in the extraction and refining processes disclosed herein, such systems are described in U.S. Pat. No. 6,254,734 and are commercially available from multiple vendors, for example, Poly Products Inc., Condorchem Envitech, Aqua Logic Inc., Schutte & Koerting and others. An important aspect to being able to fully recover and recycle the solvent for further use is the selection of a solvent as disclosed in the next section below. Another important aspect of the solvent recovery system is that while solvent is recycled, water that was introduced into the solvent with the plant material is efficiently and effectively decanted from the solvent, such that it can be directed to a waste water treatment facility, while complying with regulations with respect to volatile organics and solvents.

In some aspects, the solvent recycling system comprises: (i) at least one decanting tank for separating solvent phase and aqueous phase; (ii) evaporating systems equipped with barometric condensers for removing solvent and water from process streams, wherein the vapors are collected and transferred to the decanting tank; (iii) at least one stripper distillation for stripping solvent residues from waste water stream, wherein the distillate is collected and transferred to the decanting tank; (iv) decanting systems for separating process streams into an aqueous phase and organic phase, wherein the aqueous phase is transferred to the stripper to recover the solvent; (v) a press for separating depleted biomass from liquids, wherein the pressed depleted biomass is transferred to a dryer and the liquids are transferred for further refining; (vi) a dryer for drying solids, wherein the vapors are collected and transferred to the decanting tank, and wherein the solids comprise depleted plant material after extraction and loaded solid adsorbents; (vii) a chiller, wherein the solvent is chilled to a designated temperature; and, (viii) pumps and piping systems operated under a controller to continuously collect streams from operation units and transfer recycled stream of chilled solvent to the extraction unit and the barometric evaporators.

In some embodiments, at least 99% of the solvent is recovered as freshly regenerated solvent for further extraction. In some embodiments, the aqueous stream comprises less than or equal to about 0.1%, 0.01% or even less than or equal to about 0.005% solvent and is suitable to be treated in industrial waste water plants. In some embodiments, the solids comprise less than or equal to about 0.5%, 0.1% or even less than or equal to about 0.01% solvent, and less than or equal to about 0.1% water.

Solvent

In some aspects, the solvent may comprise a solvent or a mixture of solvents, wherein the solvent or mixture of solvents (i) is categorized as class 3 according to Q3C—Table and Lists Guidance for Industry (US Department of Health and Human Services, FDA, CDER, CBER), June 2017 ICH rev. 3; and/or (ii) forms a heterogeneous azeotrope with water, wherein the azeotrope has a boiling point lower than the boiling point of water. In some embodiments, the solvent or a mixture of solvent forms a heterogeneous azeotrope with water, wherein the solvent and the azeotrope have a boiling point lower than the boiling point of water. In some embodiments, the ratio of water to solvent, $R_w/R_s$, may be greater in the vapor phase of the azeotrope than in the solvent liquid phase. In some embodiments, the solvent or mixture of solvents is selected to have a Hildebrand solubility parameter of at least about 10.0 $MPa^{1/2}$, or more. In some embodiments, the solvent or mixture of solvent is selected to have a Hildebrand solubility parameter of about 40.0 $MPa^{1/2}$, or less. In some embodiments, the solvent or mixture of solvent is selected to have a Hildebrand solubility parameter of about 26.0 $MPa^{1/2}$, or less. In some embodiments, the solvent or mixture of solvent is selected to have a Hildebrand solubility parameter of about 20.0 $MPa^{1/2}$, or less. In some embodiments, the solvent or mixture of solvents is selected to have a Hildebrand solubility parameter in the range of about 18.0 to about 20.0 $MPa^{1/2}$. The solvent may be selected from 1-butanol, ethyl acetate, ethyl formate, 2-methyl-1-butanol, ethanol, heptane, cyclohexane, 2-butanone, 2-propanol, propylene glycol and mixtures thereof. In some embodiments, the solvent is ethyl acetate or ethyl formate. Alternatively, the solvent may be selected from pentanol, hexanol, heptanol, 2-ethyl hexanol, octanol, 2-butanone (MEK), methyl isobutyl ketone (MIBK).

In some embodiments, the solvent is dry, or saturated with water, or is present at its water azeotrope composition. In some embodiments, the solvent comprises a carboxylic acid, e.g. acetic acid, citric acid, formic acid. In some embodiments, the concentration of the carboxylic acid is about 0.01%, 0.05%, 0.1%, 0.2%, 0.3%, 0.4%, 0.5%, 0.6%, 0.7%, 0.8%, 0.9%, 1%, or more.

In some embodiments, the water stream comprises less than 30% wt/wt solvent, such as less than 25%, 20%, 15%, 10%, 9%, 8%, 7%, or 6%, or less wt/wt solvent. In some embodiments, stripper 340 comprises a distillation unit, suitable to distill the solvent/water azeotrope at the top, while water remains at the bottom of the distillation unit. In some embodiments, the stripper comprises a packed column distillation unit. The top distillate of stripper 340 may be transferred by conduit 341 back to liquid/liquid separator 330. In some embodiments, the temperature of the distillation top can be controlled at about 40-95° C., such as about 50-85° C. or about 65-75° C. In some embodiments, the temperature of the distillation top is about 70° C. In some embodiments, the bottom stream comprises about 2% wt/wt, or less, solvent, such as less than or equal to about 1, 0.1, or even less than or equal to about 0.05% wt/wt solvent. In some embodiments, bottom distillates W301 of stripper 340 are transferred by conduit 342 to a waste water treatment facility.

Remediating Unit

Intoxicating compounds can be fully removed from the final product, while maintaining the presence of "full spectrum" of extracted constituents, comprising a variety of beneficial extracted constituents. Selective removal of the undesired constituents, referred to as remediation, can be achieved by chromatography. Chromatography can be carried out by any chromatographic technique (e.g., using a simulated moving bed (SMB) or sequential simulated moving bed (SSMB) process). Some chromatographic methods afford a continuous fractionating process that provide at least two streams of products, termed extract stream(s) and raffinate stream. Examples of simulated moving bed processes are disclosed, for instance, in U.S. Pat. Nos. 6,379,554; 5,102,553; 6,093,326; and 6,187,204, and examples of sequential simulated moving bed processes can be found in GB 2,240,053; and U.S. Pat. Nos. 4,332,623; 4,379,751; and 4,970,002, each of which is incorporated herein by reference in its entirety. SSMB can be described as sequential steps of batch separation. In an SMB or SSMB setup, the resin bed can be divided into a series of discrete vessels, each of which sequence through a series of 4 zones (e.g., extraction, separation, feed/separation/raffinate and safety) connected by a recirculation loop. In some embodiments, the at least one zone of the 4 zones comprise a feed zone, an extraction zone, a separation zone, a feed/separation/raffinate zone, and a safety zone. In some embodiments, the series of 4 zones comprises an extraction zone, a separation zone, a feed/ separation/raffinate zone, and a safety zone. Any zone may be connected by a recirculation loop. A manifold system can connect the vessels and directs, in appropriate sequence to (or from) each vessel, each of the four media accommodated by the process. Those media may be referred to as feed, eluent, extract and raffinate. For example, a feed can be the purified oil mixture 1316 (FIG. 2B, 2C, or 2D), the eluent can be the solvent, the extract is a solution enriched with THC (as well as at least one more cannabinoid such as CBN or CBC), while raffinate is a solution comprising CBD and other extracted constituents such as CBG.

In some embodiments, the extract can be enriched with THCV, CBN, Δ9-THC, Δ8-THC, CBL, CBC, CBCA, or any combination thereof, wherein enrichment is compared to the feed stream or the raffinate stream. In some embodiments, the raffinate can be enriched with CBDVA, CBDV, CBG, CBD, CBCA, or any combination thereof, wherein enrichment is compared to the feed stream or the extract stream. For example, the feed may comprise about 0.3% CBN, while the extract can comprise about 4.5% CBN and the raffinate can comprise less than 0.001%; the feed may comprise about 2.4% δ9-THC, and the extract can comprise about 12% δ9-THC while the raffinate can comprise less than 0.3% or even less than 0.1% δ9-THC; the feed may comprise about 0.2% CBL and the extract can comprise about 0.9% CBL while the raffinate can comprise less than 0.01% CBL; the feed may comprise about 1.5% CBCA and the extract can comprise about 0.8% CBCA while the raffinate can comprise less than 0.3% CBCA. In another example, the feed may comprise less than 0.001% CBDVA and the raffinate can comprise about 0.08% CBDVA while the extract can comprise less than 0.2% CBDVA; the feed may comprise about 0.5% CBDV and the raffinate can comprise about 0.5% CBDV while the extract can comprise less than 0.01% CBDV; the feed may comprise about 1.2% CBG and the raffinate can comprise about 1.3% CBG while the extract can comprise less than 0.1% CBG; the feed can comprise about 86% CBD and the raffinate can comprise about 91% CBD while the extract can comprise less than 40% CBD.

In some embodiments, the extract stream can be used as feed for another separation process. In some embodiments, at least one of CBN, δ9-THC, δ8-THC, CBL, CBC, CBCA can be isolated from the extract stream by an additional chromatography step, by crystallization, by liquid/liquid extraction, by membrane filtration or by combination of thereof. In some embodiment, the raffinate stream can be used as feed for another separation process. In some embodiments, at least on of CBD, CBDVA, CBDV, CBG, can be isolated from the extract stream by an additional chromatography step, by crystallization, a liquid/liquid extraction, by membrane filtration or by combination thereof. In some embodiments, the concentration of CBD in the raffinate is so high that it is necessary to inhibit crystallization by adding at least one of medium chain triglycerides, propylene glycol or vegetable glycerin.

In some embodiments, the second refined oil and the raffinate stream are substantially the same purity. In some embodiments, the purified oil and the raffinate stream are substantially the same purity. SSMB chromatography may not affect the purity of the second refined oil or the purified oil. SSMB chromatography can affect the ratio of the constituents (e.g., cannabinoids) of the second refined oil or the purified oil. For example, the second refined oil or the purified oil may consist essentially of a mixture of CBN, δ9-THC, δ8-THC, CBL, CBC, CBCA, CBD, CBDVA, CBDV, or CBG, and the raffinate stream(s) may essentially consist of one or two of these constituents, wherein each of the second refined oil and the raffinate stream, the purified oil and the raffinate, or a combination thereof may consist essentially of the same purity. In other words, while the SSMB chromatography method can be used to change the ratio of each constituent in the raffinate stream, it may not be used to remove intoxicating or non-active constituents (e.g., because there are none to remove during the SSMB chromatography method).

The chromatographic fractionation can be carried out in a batch mode, a simulated moving bed (SMB) mode or a sequential simulated moving bed (SSMB) mode, which is a form of batch operation. The temperature of the chromatographic fractionation can be in the range of 5° C. to 90° C. The chromatographic fractionation can be carried out with a linear flow rate from about 0.40-5 ml/min·cm$^2$, about 0.25-10 ml/min·cm$^2$, or about 0.25-20 ml/min·cm$^2$ in the separation column.

A method for medium and large-scale chromatographic separations can be the sequential simulated moving bed (SSMB) mode. The chromatographic separation can be conducted using a simulated moving bed (SMB) mode. Both methods may use a number of columns packed with a suitable adsorbent and connected in series. There can be inlet ports for feed and solvent (which may include recycled solvent), and outlet ports for two or more products (or other separated fractions). The injection of the mixture solution to be separated may be periodically switched between the columns along the direction of the liquid flow, thereby simulating continuous motion of the adsorbent relative to the ports and to the liquid. In some embodiments, the chromatography system may comprise more than or equal to 14 packed bed columns comprising one or more of the above resins. In some embodiments, the chromatography system comprises 1 to 14 packed bed columns comprising one or more of the above resins. In some embodiments, the number of packed columns is about 2 to 10, or 4 to 8 or about 6. In a preferred embodiment, the number of packed columns is 6. In a preferred embodiment, a single type of adsorbent resin is used. In a preferred embodiment, there are six adsorbent beds in a 1-2-2-1 arrangement. In some embodiments, there are six adsorbent beds in a 1-2-2-1 arrangement, wherein one adsorbent bed is operated in an extraction zone, two adsorbent beds are operated in a separation zone, two adsorbent beds are operated in an adsorption (e.g., feed/separation/raffinate) zone, and one adsorbent bed is operated in a safety zone, respectively. In some embodiments, there are six adsorbent beds in a 1-2-2-1 arrangement, wherein one adsorbent bed is operated in a desorption zone, two adsorbent beds are operated in a no-flow zone, two adsorbent beds are operated in an adsorption zone, and one adsorbent bed is operated in a no-flow zone, respectively.

In some embodiments, purified cannabinoid oils can be remediated to remove intoxicating constituents, i.e., THC, by sequentially adsorbing and desorbing, using a SSMB system. In some embodiments, a plant-derived (e.g., cannabis) extract from a process not described herein can be subjected to the remediation process described herein. In some embodiments, the adsorbent is a reverse phase adsorbent, i.e., a polymer based reverse phase or a modified silica based reverse phase. Suitable reverse phase polymeric based adsorbents are available, for example, from Purolite (Chromalite® PCG600M, PCG900M, PCG1200M, PCG600C, PCG900C, PCG1200C). In some embodiment, the adsorbing media is a PCG600M or a PCG600C polymers, which have particle size >45 micron.

Reverse phase chromatography is a widely used, well proven method to separate multiple compounds and biomolecules. Typically, eluted molecules are adsorbed onto the hydrophobic resin in a relatively polar mobile phase. Decreasing the mobile phase polarity by adding more organic solvent reduces the hydrophobic interaction between the solute and the solid support resulting in desorption. The more hydrophobic the molecule, the more time it will spend on the solid support and the higher the concentration of organic solvent required to promote desorption. However, reverse phase media can have high affinity to multiple constituents that may be present in a plant-based extract, such affinity may lead to gradual fouling of the solid phase resin, eventually resulting in gradual loss of separation ability. This can be the result of constituents that were co-extracted from the plant being more strongly adsorbed on the resin, such that eventually the surface it presents to the eluted molecules is altered, resulting in loss of separation. One approach to prevent such loss of separation power is the use of a pre-column, which typically comprises the same resin as the main column system, which is positioned at the entry to the chromatography system to adsorb fouling compound. Such a pre-column can be periodically changed, and the loaded pre-column can be regenerated, thus ensuing higher cost of operation, and higher material loss. Another approach is to periodically stop operating the system to regenerate the fouled columns by rinsing them with a different desorbent of higher desorbing power. Such approach results in down time and loss of materials, as the regeneration solution is typically treated as waste, which may be unpractical if fouling occurs often. Therefore, the purity of a mixture that is feed into a sequential simulated moving bed chromatography system is a major factor in the ability to run the remediation system for prolonged periods and at acceptable costs.

The run time for the sequential simulated moving bed chromatography can be at least about 1 day, 2 days, 3 days, 4 days, 5 days, 6 days, 7 days, 2 weeks, 4 weeks, 2 months, 4 months, 6 months, 8 months, 10 months, 1 year, 2 years, 3 years, 5 years, 10 years, or more. The run time for the sequential simulated moving bed chromatography can be at most about 10 years, 5 years, 3 years, 2 years, 1 year, 10 months, 8 months, 6 months, 4 months, 2 months, 1 month, 2 weeks, 1 week, 6 days, 5 days, 4 days, 3 days, 2 days, 1 day, or less. In some embodiments, the run time for the sequential simulated moving bed chromatography can be multiple years, for example more than 1 year, 2 years, 3 years, 4 years, 5 years, or more than 10 years. The run time for the sequential simulated moving bed chromatography can be from about 1 day to about 1 year, about 2 days to about 1 month, or about 3 days to about 7 days. The run time for the sequential simulated moving bed chromatography can be from about 1 year to about 10 years.

The remediation system may be desorbed with a non-polar (e.g., D2 solvent) during the repeating step sequence of the remediation process. For example, the D2 solvent may be part of the solvent mixture introduced to the remediation process. The point at which the non-polar solvent is introduced to the remediation system may not affect the effectiveness of the desorption of the remediation system. The remediation process may be performed on a filtered and decarboxylated distillate oil (which may be unwinterized), a purified oil, a refined oil (e.g., first refined oil, second refined oil, etc), or any combination thereof. The non-polar solvent may be a D2 described herein (e.g., hexanes, pentane, heptane, acetone, or any combination thereof). The remediation system may comprise fouling agents, which embed themselves within the remediation columns. The fouling agents may desorb from the remediation system using the non-polar solvent. The desorption of the remediation system described herein may prevent or eliminate fouling and subsequent loss of capacity of the remediation system. The desorption of the remediation system described herein may allow the remediation system and remediation process described herein to run for at least at least about 1 day, 2 days, 3 days, 4 days, 5 days, 6 days, 7 days, 2 weeks, 4 weeks, 2 months, 4 months, 6 months, 8 months, 10 months, 1 year, 2 years, 3 years, 5 years, 10 years, or more. The desorption of the remediation system described herein may allow the remediation system and remediation process described herein to run for at most about 10 years, 5 years, 3 years, 2 years, 1 year, 10 months, 8 months, 6 months, 4 months, 2 months, 1 month, 2 weeks, 1 week, 6 days, 5 days, 4 days, 3 days, 2 days, 1 day, or less. The scalability of the systems and methods described herein may be feasible as a result of the ability to desorb the remediation system with a non-polar (e.g., D2 solvent) as an integral step in the repeating sequence of the remediation system. Desorbing the remediation system with a non-polar solvent may be done at any point in the remediation process described herein.

In some embodiments, cannabinoids can be fractionated using a cross-linked dextran gel that is commercially available from Amersham Biosciences (Sephadex® LH20), Biotech GmbH (Zetadex 20-LH), Sorbtech (SorbaDex™ LH20) or equivalent products. In some embodiments, a macroreticular nonionic aliphatic acrylic polymer can be used as the chromatography media, such media available from, for example, Dow (AMBERLITE™ XAD7HP), Purolite (Purosorb™ PAD900RFM or Purosorb™ PAD600RFM). In some embodiments, a macroreticular strong cation exchange resin in the $Ag^+$ form can fractionate cannabinoids. Such resins are available, for example, from Dow (Amberlyst XN-1010), Bio-Rad (Bio-Rex™ 70). An amberlyst XN-1010 resin in the $Ag^+$ form was used to separate different resin acids where separated (S. S. Curran et. al., *JAOCS*, 1981, 58, 980-982). Other chromatographic media can also be modified to be in the $Ag^+$ form to achieve separation, such modification is also termed "argentation" or Immobilized Metal Affinity Chromatography (IMAC) or Metal Chelate Affinity Chromatography (MCAC). For example, U.S. Pat. No. 4,961,881 discloses the separation of polyunsaturated triglycerides from monounsaturated triglycerides and polyunsaturated fatty acids from monounsaturated fatty acids is performed by an adsorptive chromatographic process in liquid phase using silver- or copper-exchanged aluminosilicates as the adsorbent. In another example, U.S. Pat. No. 4,305,882 disclosed mixtures containing polyunsaturated fatty esters are fractionated by partial argentation resin chromatography, in which the mixture is eluted through a column packed with a partially silvered sulfonic acid ion exchange resin. In some embodiments, the silverized chromatography media can be chitosan, spherical highly pure silica of defined particle size and defined pore size, wherein the defined pore size may be in the range of about 10 Angstroms to 100 Angstroms, or irregular silica having a size range of from about 60-200 microns and a defined pore size, wherein the pore size may be in the range of about 10 Angstroms to about 100 Angstroms, such as available from SiliCyle, Quebec City. In some embodiments, a different metal cation or mixture of metal cation can be used to modify the chromatographic media, for example $K^+$, $Na^+$, $Ag^+$, $Cs^+$, $Rb^{3O}$, $Li^+$, $Mn^{2+}$, $Cu^{2+}$, $Ca^{2+}$, $Mg^{2+}$, $Ba^{2+}$, $Be^{2+}$, $Sr^{2+}$, $Fe^{3+}$, $La^{3+}$, $Ce^{3+}$, $Sc^{3+}$, $Y^{3+}$, as well as organic cations such as $NH_4^+$, $CH_3NH_3^+$, $(CH_3)_2NH_2^+$, $C_2H_5NH_3^+$, etc., and mixtures thereof.

In some embodiments, the desorbent is a dry solvent, wherein the solvent may be the same solvent used in extraction and refining or a different solvent. In some embodiments, the desorbent comprises a solvent, wherein the solvent is saturated with water or wherein the composition is the azeotrope composition of solvent and water. In some embodiments, the adsorbent and/or desorbent comprises the water-saturated solvent, wherein the solvent further comprises about 0.0001 M, or more, carboxylic acid. In some embodiments, the adsorbent and/or desorbent comprises the water-saturated solvent, wherein the solvent further comprises about 1 M, or less, carboxylic acid. In some embodiments, the adsorbent and/or desorbent comprises the water-saturated solvent, wherein the solvent comprises about 0.0001 to 1 M carboxylic acid.

In some embodiments, the solvent is a mixture of ethanol and ethyl acetate at a ratio of about 1:5, or less. In some embodiments, the solvent is a mixture of ethanol and ethyl acetate at a ratio of about 5:1, or more. In some embodiments, the solvent is a mixture of ethanol and ethyl acetate at a ratio of about 1:5 to 5:1, or the azeotrope ratio of ethanol and water and the resin is Purosorb™ PAD900RFM or Purosorb™ PAD600RFM.

In some embodiments, the method of fractionating a high purity cannabis extract comprises a sequential simulated moving bed chromatography sequence, wherein the sequence comprises: (1) passing a feed stream comprising high purity cannabis oil into an adsorbent, thereby flushing a raffinate stream comprising THC and additional cannabinoids from the adsorbent; (2) flushing an extract stream enriched in CBD and additional cannabinoids relative to the feed stream with a desorbent stream; and (3) recycling the desorbent stream back to the adsorbent.

In some embodiments, the method of fractionating a high purity cannabis extract comprises a sequential simulated moving bed chromatography sequence, wherein the sequence comprises: (1) passing a feed stream comprising high purity cannabis oil into an adsorbent, thereby flushing a raffinate stream comprising THC and additional cannabinoids from the adsorbent; (2) flushing an extract stream enriched in CBD and additional cannabinoids relative to the feed stream with a desorbent stream; and (3) advancing at least one oil wave front by recycling the whole system from the last column to the first column of the sequence, wherein the at least one oil wave front comprises at least one plant-extracted constituent.

In some embodiments, for remediating purified cannabis extract, a highly refined oil is feed into the chromatography separation, comprising at least about 82%, 84%, 85%, 86%, 87%, 88%, 89%, 90%, 91%, 92%, 93%, 94%, 95%, or more wt/wt pure cannabinoids. In some embodiments, the purity of the feed is not less than about 82% cannabinoids. In some embodiments, resolution and yield of the chromatography process is enhanced by feeding a purified oil, comprising at most about 95%, 90%, 85%, or less pure cannabinoids. In some embodiments, the purified oil fed to chromatography comprises less than or equal to about 5%, 4%, 3%, 2%, 1% wt/wt sterols, terpenes and fatty acids. In some embodiments, the purified oil fed to chromatography comprises more than or equal to about 1%, 2%, 3%, 4%, 5%, or more wt/wt sterols, terpenes and fatty acids. In some embodiments, the feed into the chromatography separation is contacted with a solution of the basic amino acid, the protamine, or a combination thereof. In some embodiments, contacting the feed with the basic amino acid, the protamine, or a combination thereof effectively removes fatty acids prior the chromatography separation. In some embodiments, fatty acids foul the chromatography resin. Fouled chromatography resin may reduce efficiency of the chromatography separation. In some embodiments, the feed is distilled prior to introduction to the chromatography separation. Distilling the feed prior to chromatography separation reduces the content of higher and lower boiling point compounds in the feed, such, for example, terpenes, sesquiterpenes, oxi-sesquiterpenes, sterols, fatty acids, or combinations thereof. In some embodiments, terpenes, sesquiterpenes, oxi-sesquiterpenes, sterols or fatty acids foul the chromatography resin.

In some embodiments, a fraction of THC-depleted is collected, that is characterized as having about 0.3%, or less, or not more than about 0.001% THC. In some embodiments, a second fraction is collected, which as characterized as having more than or equal to about 1%, 2%, 3%, 4%, 5%, 6%, 7%, 8%, 9%, 10%, or more, THC.

In another aspect, most chromatography separations, and particularly reverse phase chromatography entail significant dilution of the product in the desorbent phase. The excess desorbent can be removed from the products and recycled for further use, preferable at minimal energy requirements. Ease of solvent stripping from products and solvent recyclability may be highly impacted by the choice of the desorbent system.

In some embodiments, a dual-desorbent chromatography (DDC) can be applied, wherein two desorbents (denoted D1 and D2) of different polarities are applied in sequence to the chromatography system. In some embodiments, D1 and D2 comprise the same solvents in different volume (or weight) ratios. In some embodiments, D1 and D2 comprise solvents that form an azeotrope with water in a binary or ternary mixture. In some embodiments, the boiling point of the azeotrope is lower than 85° C., 70° C., 60° C., or even lower than 50° C., and is lower than the boiling point of each individual solvent of the mixture. In some embodiments, D1 and D2 separate into two liquid phases at temperature of about 10° C. to about 50° C., wherein one phase comprises D1 and the second phase comprises D2. In some embodiments, D1 and D2 form azeotropes with distinctively different boiling point, such that a mixture of D1 and D2 can be stripped in a first stripping distillation column under first conditions of temperature and pressure, wherein D2 is recovered by condensing the vapor phase, while the bottom liquid phase can then be stripped in a second striping to recover D1 in the vapor phase under different temperature and pressure, with the stripped oil phase remaining at the bottom liquid phase. In some embodiments, the relative polarity of D1 is evaluated according to Christian Reichardt, *Solvents and Solvent Effects in Organic Chemistry*, Wiley-VCH Publishers, 3rd ed., 2003, in the range 0.60-0.75, and the relative polarity of D2 is in the range of 0.001-0.65. D1 and D2 can comprise, for example, binary mixtures of ethanol-water or propanol-water, or ternary mixtures of ethanol-water or propanol-water, and the ternary mixtures are selected from pentane-ethanol-water, hexane-ethanol-water, acetone-propanol-water, ethyl acetate-ethanol-water, heptane-ethanol-water, or cyclohexane-ethanol-water.

In some embodiments, the method of remediating a high purity cannabis extract comprises a sequential simulated moving bed chromatography sequence operated in a dual desorbent mode, wherein the sequence comprises: (1) passing a feed stream comprising high purity cannabis oil and D1 into a reverse phase adsorbent while simultaneously drawing a raffinate fraction rich in the desired constituent (e.g. CBD), and at the same time flushing at a different point with D2 an extract stream comprising at least one constituent to be removed (e.g. THC) from the adsorbent; (2) further flushing an extract stream with D1; (3) flushing a raffinate stream with D1 to complete the desired constituent (e.g. CBD) recovery (4) advancing at least one oil wave front in the presence of D1 by recycling the whole system from a last column to a first column of the sequence, wherein the at least one oil wave front comprises at least one plant-extracted constituent. In some embodiments, eluted compounds are not recycled back to the adsorbent (i.e. eluted compounds travel once through the chromatography system). In some embodiments, the at least one constituent to be removed comprises at least one intoxicating constituent and constituents that foul the chromatography resin. In some embodiments, the method can be operated for prolonged periods with no need for stopping for regenerating the adsorbent.

In some embodiments, the SSMB sequence may consist of D1 as the desorbent. The extract stream can be highly purified oil when the SSMB sequence consists of D1. The extract stream may comprise constituents that foul the adsorbent of the SSMB sequence. The constituents that foul the adsorbent of the SSMB sequence can be removed before introducing the extract stream to the SSMB sequence. The constituents that foul the adsorbent of the SSMB sequence can be removed while the extract stream is processed by the SSMB sequence.

Figure 2B:
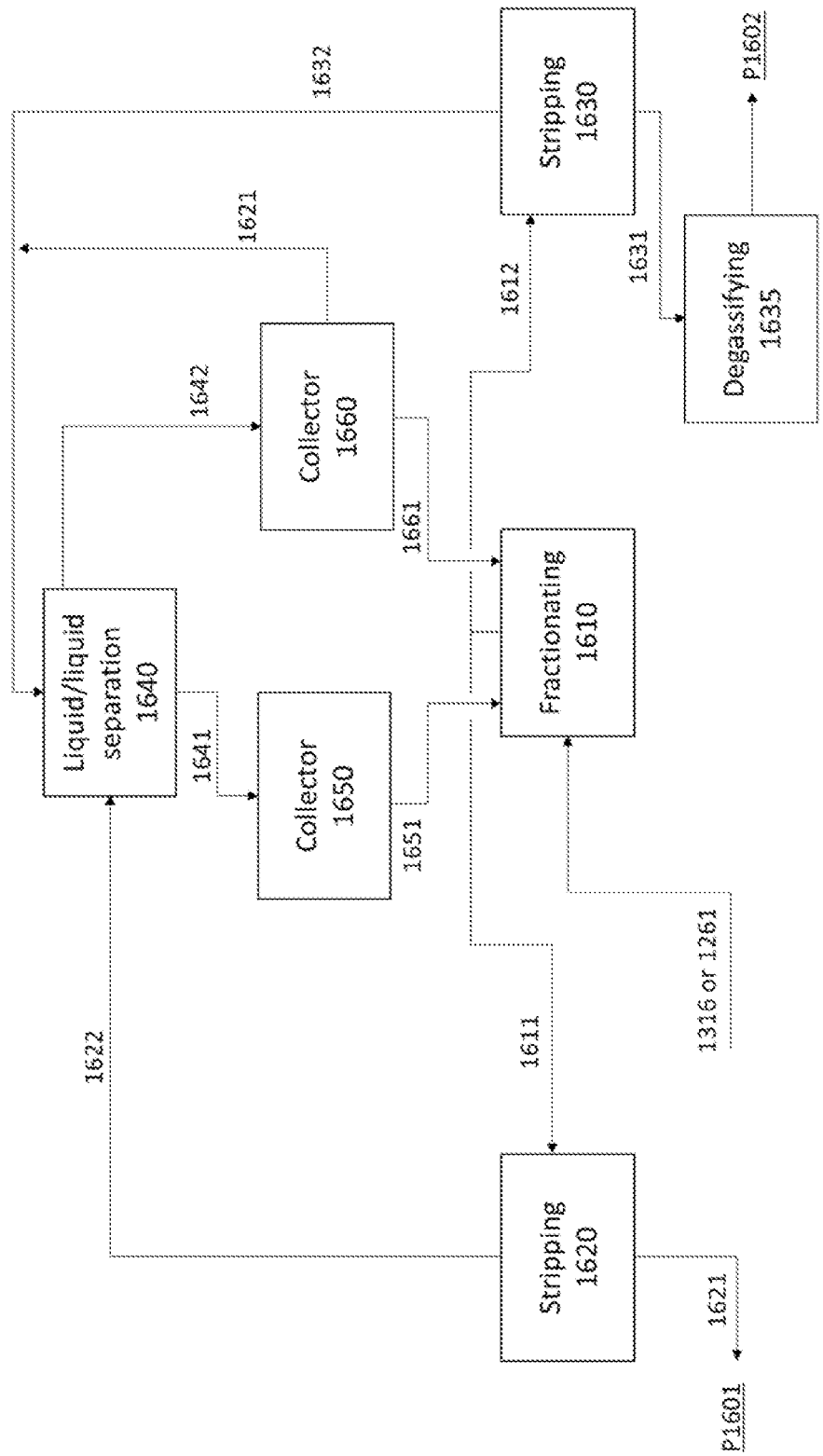
FIG. 2B illustrates a schematic diagram of a process for the remediation of the purified extracted oil by fractionation to obtain two product streams, and to recover the solvents used in the remediation process.
Figure 2C:
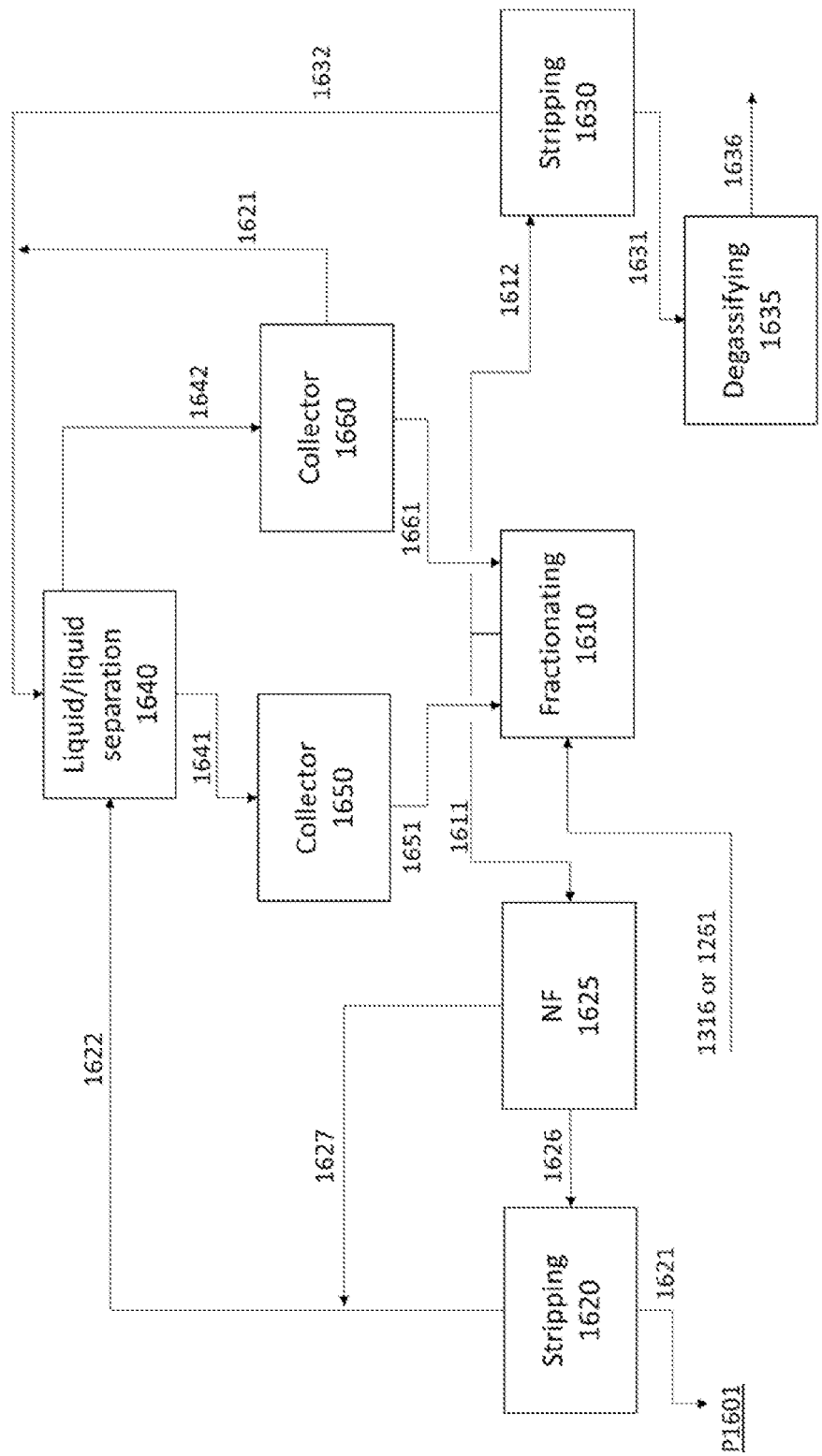
FIG. 2C illustrates an alternative schematic diagram of a process for the remediation of the purified extracted oil by fractionation to obtain two product streams, and to recover the solvents used in the remediation process.
Figure 2D:
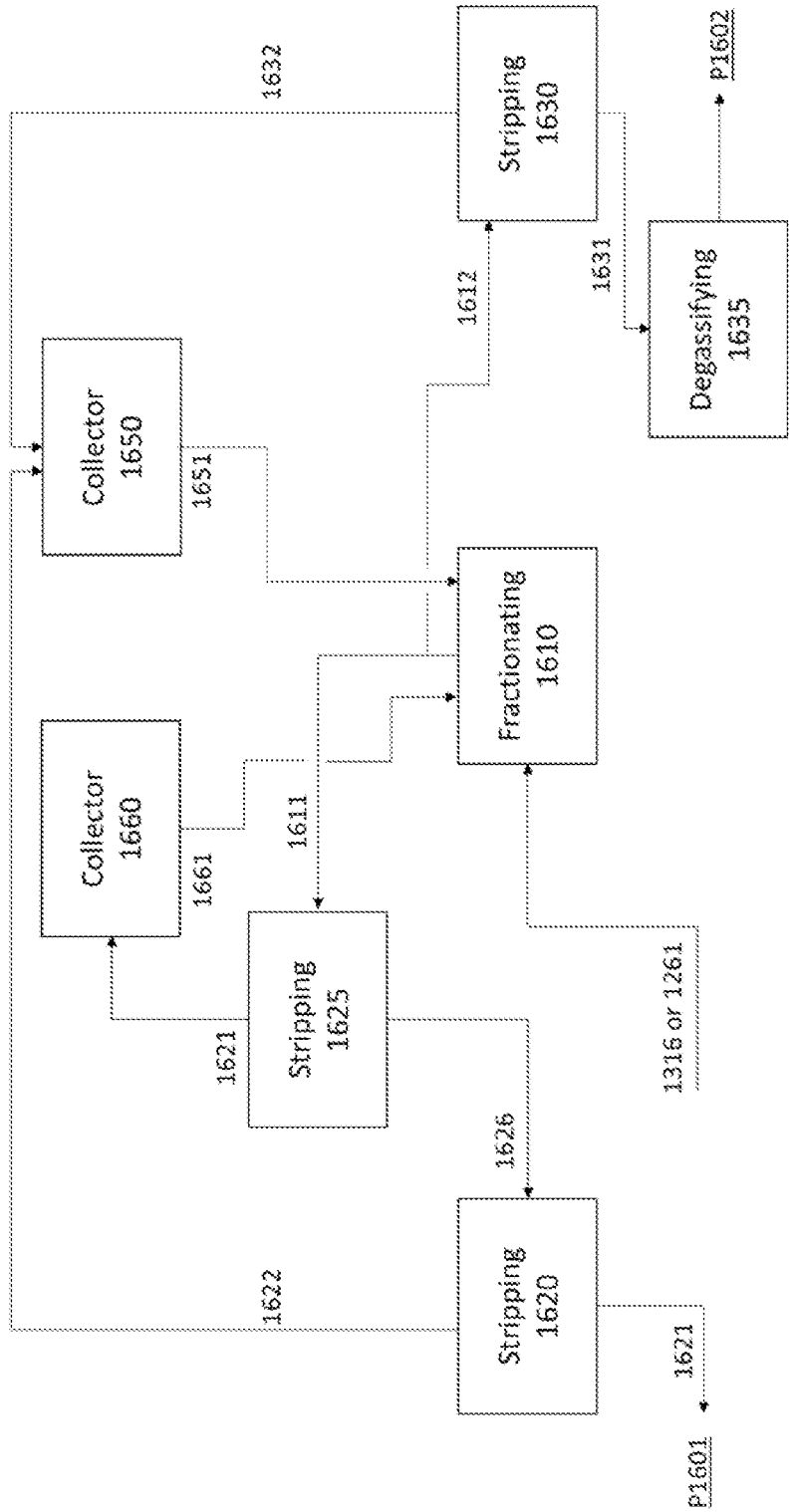
FIG. 2D illustrates another alternative schematic diagram of a process for the remediation of the purified extracted oil by fractionation to obtain two product streams, and to recover the solvents used in the remediation process.

Referring to FIG. 2B, a sufficiently refined oil (e.g. the purified oil or the second refined oil as disclosed herein above) can be mixed with D1 to make it flow at 10° C. to 30° C. and can be fed to fractionating (1610) by reverse phase chromatography, while D2 is transferred from collector 1660 via conduit 1661 to flush and extract. The extract stream can be optionally transferred via conduit 1611 to stripper 1620 for solvent recovery. The product stream 1631 can then be fed into degasifier 1635, where residues of solvent and water are eliminated to yield product P1601. In some embodiments, degassing is conducted at temperature of about 100° C. to 140° C. and pressure of about 10 Torr to about 30 Torr. In some embodiments, the temperature of degassing is about 120° C. D1 is then transferred from collector 1650 via conduit 1651, to flush a raffinate, which is transferred via conduit 1612 to stripping 1630, where it is stripped off the D1 solvent to collect product P1602. D1 can then be transferred from collector 1650 via conduit 1651, to flush the extract and can be transferred via conduit 1611 to stripping 1620 for solvents recovery. In some embodiments, prior to stripping (FIG. 2C), stream 1611 is transferred through nano-filter (NF) 1625, separating permeate 1627, comprising solvents and water, and retentate 1626, comprising molecules having molecular wt greater than 90 g/mol, 100 g/mol, 110 g/mol, 120 g/mol, 130 g/mol, 140 g/mol, 150 g/mol. In some embodiments, 50%, 60%, 70%, 75%, 80%, 85% of the solvent and water in stream 1611 is recovered in permeate 1627. Any fouling material that accumulates in the system can be flushed with this stream. Both stripper 1620 and 1630 transfer the vapor phase, via a condenser, to liquid/liquid separation 1640. The combined phases can be mixed at 1640, forming a ternary azeotrope mixture, which separates to form a D1 phase and a D2 phase. The D1 heavier phase can be transferred via conduit 1641 to collector 1650 and the light phase D2 can be transferred via conduit 1642 to collector 1660. In some embodiments, excess water can be removed by simple azeotrope distillation and decantation. A portion of D2 phase can be recycled via conduit 1621 back to separation 1640 to control the ternary mixture composition. In some embodiments, chromatography, liquid/liquid separation and the collectors are controlled at a temperature of about 15° C. to about 25° C., or at about 20° C. In some embodiments, stripping is conducted at about 40° C. to about 100° C. and at pressure of about 100 Torr to about 300 Torr. In some embodiments, about 1 kw, 2 kw, 3 kw, 4 kw, 5 kw, 6 kw, 7, 8 kw, 9 kw, 10 kw, 15 kw energy is required per kg CBD. In some embodiments, not more than 5 kw, 6 kw, 7 kw, 8 kw, 9 kw, 10 kw 15 kw of energy is required per kg of CBD. In some embodiments, about 3.7 kw of energy is required per kg of CBD.

In an alternative setup of the remediation module (FIG. 2D), a sufficiently refined oil (e.g. the purified oil or the second refined oil as disclosed herein above) is mixed with D1 to make it flow at 10° C. to 30° C., and is fed to fractionating (1610) by reverse phase chromatography, while D1 is transferred from collector 1650 via conduit 1651 to flush an extract, followed by flushing of the extract with D2, which is transferred via conduit 1116 from collector 1660. D1 can then be transferred from collector 1650 via conduit 1651, to flush the extract and can be transferred via conduit 1611 to stripping 1625 to recover D2 by a first azeotrope stripping, wherein the vapors can be condensed and transferred via conduit 1621 to collector 1660; the bottom liquid phase can be transferred via conduit 1626 to stripping 1620, wherein D1 can be recovered in a second azeotrope stripping, wherein vapors can be condensed and transferred vial conduit 1622 to collector 1650, and the bottom liquid phase can be optionally degasified to produce product P1601. In some embodiments, D2 can be stripped at temperature of about 28° C. to about 35° C. and pressure of about 580 Torr to about 620 Torr, while D1 can be stripped at temperature of about 45° C. to about 55° C. and pressure of about 150 Torr to about 250 Torr. Sequentially, D1 can then be transferred from collector 1650 via conduit 1651, to flush a raffinate, which can be transferred via conduit 1612 to stripping 1630, where it can be stripped off the D1. The product stream 1631 can then be fed into degasifier 1635, where residues of solvent and water can be eliminated to collect product P1602. In some embodiments, degasifier is conducted at temperature of about 100° C. to 140° C. and pressure of about 10 Torr to about 30 Torr. In some embodiments, the temperature of degassing is about 120° C. Any fouling material that accumulates in the system can be flushed with the extract stream. In some embodiments, excess water can be removed by simple azeotrope distillation and decantation. In some embodiments, chromatography, liquid/liquid separation and the collectors are controlled at a temperature of about 15° C. to about 25° C., or at about 20° C. In some embodiments, stripping of D1 desorbent is conducted at about 40° C. to about 100° C. and at pressure of about 100 Torr to about 300 Torr. In some embodiments, about 5 kw, 6 kw, 7 kw, 8 kw, 9 kw, 10 kw, or about 20 kw energy is required per kg CBD. In some embodiments, not more than 15 kw, 16 kw, 17 kw, 18 kw, 19 kw, 20 kw or about 15 kw of energy is required per kg of CBD. In some embodiments, about 12.0 kw of energy is required per kg of CBD recovered in raffinate.

In some embodiments, product P1602 comprises at least about 85%, 86%, 87%, 88%, 89%, 90%, 91%, 92%, 93%, 94%, 95%, or more wt/wt pure cannabinoids. In some embodiments, the product P1602 comprises at most about 2%, 3%, 4%, 5%, 6%, 7%, 8%, 9%, 10% water. In some embodiments, the product P1602 comprises less than 0.1%, 0.01%, 0.001% solvent. In some embodiments, product P1602 comprises less than 0.3%, 0.2%, 0.1% or even less than 0.05% of intoxicating constituents, e.g., THC. In some embodiments, at least 80%, 81%, 82%, 83%, 84%, 85%, 86%, 87%, 88%, 89%, 90%, 95%, or more of the major constituent of the feed (e.g. CBD) is recovered in P1602. In some embodiments, product P1602 can comprise CBD and other cannabinoids. In some embodiments, this product can be further fractionated to separate rare cannabinoids or another bioactive constituent. In some embodiments, this product can be crystallized to collect crystalline CBD.

In some embodiments, the product P1601 comprises at least about 85%, 86%, 87%, 88%, 89%, 90%, 91%, 92%, 93%, 94%, 95%, or more wt/wt pure cannabinoids. In some embodiments, the product P1602 comprises up to 2%, 3%, 4%, 5%, 6%, 7%, 8%, 9%, 10% water. In some embodiments, the product P1601 comprises less than 0.1%, 0.01%, 0.001% solvent. In some embodiments, product P1601 can comprise relative enhanced fraction of THC, as well as CBD and other cannabinoids at lower amounts. In some embodiments, this product can be further fractionated to separate rare cannabinoids or another bioactive constituent. In some embodiments, this product can be reacted chemically to convert CBD to THC. In some embodiments, this product can be reacted chemically to provide a specific cannabinoid at enhanced concentration.

System Controls

In certain aspects, the system is equipped with various sensors and human interface (HMI) reporting points, all data is continuously collected, monitored and archived at a central computer.

Efficiency of extraction can be optimized by controlling parameters, such as particle size of the extracted biomass, contact time with the extractant, liquid to solid ratio, conveyor speed. concentration of extractives in the extracting solvent at each step and temperature.

In some aspects of this disclosure, contact time between biomass and the extracting solvent is controlled at each conveyor by the inclination angle of the conveyor, the rotational speed of the screw, and the pumping rate of the feeding pump.

In some aspects, feed weights of biomass and solvent are constantly monitored and logged in the data historian of the process control computer(s). Feed biomass can be analyzed for constituents composition by an online monitoring system, which may comprise NIR or a UV-VIS spectrometer. The output of extracted oil can also be analyzed by similar spectrometers and by flow meter, such that full mass control of specific constituents is facilitated.

Refined Oil

In some aspects, the refined oil may be sufficiently pure for some applications. In some aspects, the color of the purified oil is colorless to light yellow-brown. In some aspects, the UV-VIS absorption of the purified oil when diluted 1:10 to 1:100 with water-saturated ethyl acetate is less than 0.1 OD at 640-670 nm. In some aspects, the concentration of chlorophyll is less than or equal to about $10^{-5}$ or even less than or equal to about $10^{-6}$ M. In some aspect, the total cannabinoids concentration of the refined oil is at least about 50, 60, 70% or more wt/wt. In some aspect, the total cannabinoids concentration of the refined oil is at most about 70, 60, 50, 40% or less wt/wt. In some aspects, at least about 20, 30, 40 50, 60, 70, 80%, or more of the cannabinoids are carboxylated cannabinoids. In some aspects, at most about 80, 70, 60, 50, 40, 30, 20%, or less of the cannabinoids are carboxylated cannabinoids. In some aspects, the refined oil comprises more than or equal to about 0.1, 0.5, 1, 2, 3, 4, 5, 6%, or more wt/wt terpenes and sesquiterpenes. In some aspects, the refined oil comprises less than or equal to about 6, 5, 4, 3, 2, 1, 0.5, 0.1%, or less wt/wt terpenes and sesquiterpenes. In some aspects, the refined oil comprises more than or equal to about 0.5, 1, 2, 4, 5%, or more sterols. In some aspects, the refined oil comprises less than or equal to about 5, 4, 3, 2, 1, 0.5%, or less sterols.

In some aspects, the refined oil comprises less than or equal to about 5, 4, 3, 2, 1%, or less wt/wt flavonoids. In some aspects, the refined oil comprises more than or equal to about 1, 2, 3, 4, 5%, or more wt/wt flavonoids. In some aspects, the refined oil comprises less than or equal to about 5, 4, 3, 2, 1%, or less wt/wt steroids. In some aspects, the refined oil comprises more than or equal to about 1, 2, 3, 4, 5%, or more wt/wt steroids. In some aspects, the refined oil comprises less than or equal to about 5, 4, 3, 2, 1%, or less wt/wt vitamins. In some aspects, the refined oil comprises more than or equal to about 1, 2, 3, 4, 5%, or more wt/wt vitamins. In some aspects, the refined oil comprises less than or equal to about 5, 4, 3, 2, 1%, or less wt/wt hydrocarbons. In some aspects, the refined oil comprises more than or equal to about 1, 2, 3, 4, 5%, or more wt/wt hydrocarbons. In some aspects, the refined oil comprises less than or equal to about 5, 4, 3, 2, 1%, or less wt/wt glycerides. In some aspects, the refined oil comprises more than or equal to about 1, 2, 3, 4, 5%, or more wt/wt glycerides.

In some aspects, the refined oil comprises less than or equal to about 5, 4, 3, 2, 1%, or less wt/wt sugars. In some aspects, the refined oil comprises more than or equal to about 1, 2, 3, 4, 5%, or more wt/wt sugars. In some aspects, the refined oil comprises less than or equal to about 5, 4, 3, 3, 1, 0.6, 0.4%, or less wt/wt fatty acids. In some aspects, the refined oil comprises more than or equal to about 0.3, 0.5, 1, 2, 3, 4, 5%, or more wt/wt fatty acids. In some aspects, the refined oil comprises less than or equal to about 1, 0.9. 0.8, 0.7. 0.6, 0.5, 0.4, 0.3, 0.2, 0.1%, or less palmitic acid. In some aspects, the refined oil comprises more than or equal to about 0.1, 0.2, 0.3, 0.4, 0.5, 0.6, 0.7, 0.8, 0.9, 1%, or more palmitic acid. In some aspects, the refined oil comprises less than or equal to about 0.5, 0.4, 0.3, 0.2, 0.1%, or less linoleic acid. In some aspects, the refined oil comprises more than or equal to about 0.1, 0.2, 0.3, 0.4, 0.5%, or more linoleic acid. In some aspects, the refined oil comprises less than or equal to about 0.5, 0.4, 0.3, 0.2, 0.1%, or less oleic acid. In some aspects, the refined oil comprises more than or equal to about 0.1, 0.2, 0.3, 0.4, 0.5%, or more oleic acid.

Purified Oil

In some aspects, the purified oil is an essentially pure product, i.e. the remaining concentration of impurities that are eliminated from the starting crude product is well below the relevant regulatory limit for each such impurity compound. In some aspects, the color of the purified oil is colorless to light yellow-brown. In some aspects, the UV-VIS absorption of the purified oil when diluted 1:10 to 1:100 with water-saturated ethyl acetate is less than 0.1 OD at 640-670 nm. In some aspects, the concentration of chlorophyll is less than or equal to about $10^{-5}$ or even less than or equal to about $10^{-6}$ M. In some aspects, the total cannabinoids concentration of the purified oil is at least about 70, 80, 82, 84, 86, 88, 90, 92, 94 95%, or more wt/wt. In some aspect, the total cannabinoids concentration of the purified oil is at most about 70, 60, 50, 40% or less wt/wt. In some aspects the purified oil comprises at least about 85, 86, 87, 88, 89, 90, 91, 92, 93, 94, 95%, or more wt/wt de-carboxylated cannabinoids. In some aspects, at most about 80, 70, 60, 50, 40, 30, 20%, or less of the cannabinoids are carboxylated cannabinoids.

In some aspects, the purified oil comprises at least about 0.1, 0.2, 0.3, 0.4, 0.5, 0.6, 0.7, 0.8, 0.9, 1, 1.1, 1.2, 1.3, 1.4, 1.5%, or more wt/wt terpenes. In some aspects, the purified oil comprises less than or equal to about 6, 5, 4, 3, 2, 1, 0.5, 0.1%, or less wt/wt terpenes. In some aspects, terpenes that are collected separately at distillation are added back to the purified oil fraction that comprises the cannabinoids.

In some aspects, the purified oil comprises less than or equal to about 5, 4, 3, 2, 1%, or less wt/wt sugars. In some aspects, the purified oil comprises more than or equal to about 1, 2, 3, 4, 5%, or more wt/wt sugars. In some aspects, the purified oil comprises less than or equal to about 5, 4, 3, 3, 1, 0.6, 0.4%, or less wt/wt fatty acids. In some aspects, the purified oil comprises more than or equal to about 0.3, 0.5, 1, 2, 3, 4, 5%, or more wt/wt fatty acids. In some aspects, the purified oil comprises less than or equal to about 1, 0.9. 0.8, 0.7. 0.6, 0.5, 0.4, 0.3, 0.2, 0.1%, or less palmitic acid. In some aspects, the purified oil comprises more than or equal to about 0.1, 0.2, 0.3, 0.4, 0.5, 0.6, 0.7, 0.8, 0.9, 1%, or more palmitic acid. In some aspects, the purified oil comprises less than or equal to about 0.5, 0.4, 0.3, 0.2, 0.1%, or less linoleic acid. In some aspects, the refined oil comprises more than or equal to about 0.1, 0.2, 0.3, 0.4, 0.5%, or more linoleic acid. In some aspects, the purified oil comprises less than or equal to about 0.5, 0.4, 0.3, 0.2, 0.1%, or less oleic acid. In some aspects, the refined oil comprises more than or equal to about 0.1, 0.2, 0.3, 0.4, 0.5%, or more oleic acid.

In some aspects, when the process is applied for the refining of crude extract of a cannabis plant, including a hemp plant, the purified oil can be tested according to the requirements of various regulators and proven suitable for human consumption. In the US, the authorities of various states have put in place such requirements with respect to residual amounts of volatile solvents (VOC), heavy metals, pesticides and herbicides, mycotoxins and aflatoxins, as well as total bacteria count, yeast & mold and some specific bacteria.

In some aspects, implementation of processes disclosed herein in equipment designed to be cleaned and sterilized if needed by proper manufacturing practices can routinely ensure the purified oil can meet all standards related to microbiology, particularly since much of the processing is conducted in a solvent that does not generally support microbiological contamination. In some aspects, the purified oil comprises less than or equal to about 100,000, less than or equal to about 10,000, or even less than or equal to about 1000 colony forming units/g (CFU/g) total aerobic bacteria. In some aspects, the purified oil comprises less than or equal to about 10,000, or even less than or equal to about 1000 (CFU/g) yeast and mold. In some aspects, the purified oil comprises less than or equal to about 1,000, or even less than or equal to about 100 (CFU/g) bile-tolerant gram-negative bacteria. In some aspects, the purified oil comprises less than or equal to about 1,000, or even less than or equal to about 100 (CFU/g) total coliforms. In some aspects, the purified oil comprises less than or equal to about 100, or even less than or equal to about 10 (CFU/g) E. Coll. In some aspects, the purified oil comprises less than or equal to about 100, or even less than or equal to about 10 (CFU/g) *Salmonella*.

In some aspects, The purified oil comprises any of the solvents acetonitrile, benzene, butane, 1-butanol, 2-butanol, 2-butanone (MEK), 1,2,-dichloroethane, dichloromethane, 1,2-dimethoxyethane, N,N-dimethylacetamide, 2,2-dimethylbutane (hexanes) 2,3-dimethylbutane (hexanes), N,N-dimethylformamide, 2,2-dimethylpropane (neopentane), dimethylsulfoxide (DMSO), 1,4-dioxane, chloroform, cumene, cyclohexane, ethanol, 2-ethoxyyethanol, ethyl acetate, ethyl ether, ethylene glycol, ethylene oxide, heptane, hexane, isopropyl acetate, methanol, 2-methylbutane (isopentane), 2-methylpentane (hexanes), 3-methylpentane (hexanes), 2-methylpropane (isobutane), naphtha, pentane, 1-pentanol, petroleum ether, propane, 1-propanol, 2-propanol (isopropyl alcohol), 2-propanone (acetone), sulfolane, trichlorethylene, tetrahydrofuran (THF), toluene, xylenes (o-xylene, m-xylene, p-xylene), pyridine, methyl tert-butyl ether at well below the Minimum Required Limit (MRL).

In some aspects, the purified oil comprises less than or equal to about 5000 µg/g ethanol. In some aspects, the purified oil comprises less than or equal to about 3000 µg/g, or less, methanol. In some aspects, the purified oil comprises about 5000 µg/g, or less ethyl acetate. In some aspects, the purified oil comprises about 5000 µg/g, or less, butane. In some aspects, the purified oil comprises about 290 µg/g, or less hexane. In some aspects, the purified oil comprises about 60 µg/g, or less, chloroform. In some aspects, the purified oil comprises about 600 µg/g, or less dichloromethane. In some aspects, the purified oil comprises about 5 µg/g, or less, 1,2-dichloroethane. In some aspects, the purified oil comprises about 5000 µg/g, or less, acetone. In some aspects, the purified oil comprises about 410 µg/g, or less, acetonitrile. In some aspects, the purified oil comprises about 2 µg/g, or less, benzene. In some aspects, the purified oil comprises about 5000 µg/g, or less, ethyl ether. In some aspects, the purified oil comprises about 50 µg/g, or less, ethylene oxide. In some aspects, the purified oil comprises about 5000 µg/g, or less, heptane. In some aspects, the purified oil comprises about 5000 µg/g, or less, 2-propanol. In some aspects, the purified oil comprises about 400 µg/g, or less, naphtha. In some aspects, the purified oil comprises about 5000 µg/g, or less pentane. In some aspects, the purified oil comprises about 400 µg/g, or less, petroleum ether. In some aspects, the purified oil comprises about 5000 µg/g, or less, propane. In some aspects, the purified oil comprises about 80 µg/g, or less, trichloroethylene. In some aspects, the purified oil comprises about 890 µg/g, or less, toluene. In some aspects, the purified oil comprises about 2170 µg/g, or less, total xylenes.

In some aspects, the purified oil comprises less than or equal to the maximum allowed limit of any pesticide or herbicide listed by state authorities with respect to the relevant product, e.g. cannabis products. In some aspects, the purified oil comprises about 1%, 0.5%, or even less than about 0.5% ash. In some aspects, the purified oil comprises about 0.14 µg/kg, or less, Arsenic. In some aspects, the purified oil comprises about 0.09 µg/kg, or less, Cadmium. In some aspects, the purified oil comprises about 0.29 µg/kg, or less, Lead. In some aspects, the purified oil comprises about 0.29 µg/kg, or less, Mercury. In some aspects, the purified oil comprises less than or equal to the allowed limit for any other heavy metal of potential harming effect. In some aspects, the purified oil further comprises about 0.1% wt/wt, or less, Calcium, about 0.1% wt/wt, or less Magnesium, about 0.1% wt/wt, or less, potassium, about 0.05% wt/wt, or less, phosphorous.

In some aspects, the purified oil comprises total metals other than Na, K, Rb, or Cs of less than or equal to about 6000, 5000, 4000, 3000, 2000, 1000, 500, 100, or even less than about 50 µg/kg (solvent removed base, SRB). In some aspects, the purified oil comprises less than or equal to about 0.29 µg/kg SRB, or even less than about 0.14 µg/kg SRB As. In some aspects, the purified oil comprises less than or equal to about 0.09 µg/kg SRB, or even less than or equal to about 0.05 µg/kg SRB Cd. In some aspects, the purified oil comprises less than or equal to about 0.29 SRB µg/kg, or even less than about 0.15 µg/kg SRB Pb. In some aspects, the purified oil comprises less than or equal to about 0.29 µg/kg SRB, or even less than about 0.15 µg/kg SRB Hg. In some aspects, the purified oil comprises less than or equal to about 500 µg/kg SRB Ca. In some aspects, the purified oil comprises less than or equal to about 500 µg/kg SRB Mg. In some aspects, the purified oil comprises less than or equal to about 100 µg/kg SRB Zn. In some aspects, the purified oil comprises less than or equal to about 100 µg/kg SRB Fe. In some aspects, the purified oil comprises less than or equal to about 50 µg/kg SRB Cu. In some aspects, the purified oil comprises less than or equal to about 50 µg/kg SRB, or even less than about 25 µg/kg SRB Cr.

In some aspects, the purified oil comprises less than or equal to about 5, 4, 3, 2, 1%, or less wt/wt flavonoids. In some aspects, the purified oil comprises more than or equal to about 1, 2, 3, 4, 5%, or more wt/wt flavonoids. In some aspects, the purified oil comprises less than or equal to about 5, 4, 3, 2, 1%, or less wt/wt steroids. In some aspects, the purified oil comprises more than or equal to about 1, 2, 3, 4, 5%, or more wt/wt steroids. In some aspects, the purified oil comprises less than or equal to about 5, 4, 3, 2, 1%, or less wt/wt vitamins. In some aspects, the purified oil comprises more than or equal to about 1, 2, 3, 4, 5%, or more wt/wt vitamins. In some aspects, the purified oil comprises less than or equal to about 5, 4, 3, 2, 1%, or less wt/wt hydrocarbons. In some aspects, the purified oil comprises more than or equal to about 1, 2, 3, 4, 5%, or more wt/wt hydrocarbons. In some aspects, the purified oil comprises less than or equal to about 5, 4, 3, 2, 1%, or less wt/wt glycerides. In some aspects, the purified oil comprises more than or equal to about 1, 2, 3, 4, 5%, or more wt/wt glycerides.

Remediated Oil

In some aspects, fractionated oil comprises at least about 70, 80, 82, 84, 86, 88, 90, 92, 94 or 95%, or more wt/wt cannabinoids, and maintains all other purity attributes of the purified oil. Different purified oil may be collected as fractionated oil, for example broad spectrum oil, comprising not more than about 0.1% wt/wt THC (1000 ppm). In some aspects, the remediated oil can comprise about 0.1 to 0.3% THC. In some embodiments, the remediated oil comprises at least about 10, 15, 20, 25, 30, 35%, or more wt/wt cannabinoids that are not CBD (e.g., THF, CBN, CBG, etc.). In some embodiments, the remediated oil comprises at most about 35, 30, 25, 20, 15, 10%, or less wt/wt THC. In some aspects, the fractionated oil comprises at least about 1, 2, 3, 4, 5, 6 7, 8, 9, 10, 20, 30%, or more wt/wt CBN. In some aspects, the fractionated oil comprises at most about 10, 9, 8 7, 6, 5, 4, 3, 2, 1%, or less wt/wt CBN. In some aspects, the fractionated oil comprises at least about 1, 2, 3, 4, 5, 6 7, 8, 9, 10%, or more wt/wt CBG. In some embodiments, the fractionated oil comprises at most about 10, 9, 8 7, 6, 5, 4, 3, 2, 1%, or less wt/wt CBG.

In some embodiments, the remediated oil comprises at least two CBD-type cannabinoids with C1 to C5 side chains. In some embodiments, the remediated oil can comprise CBD-type compounds identified as 329-11a and 329-11c, 327-13a to 327-13c, 313-16b and 331-18a (see L. Baram et. al., *The heterogeneity and complexity of Cannabis extracts as antitumor agents*, Oncotarget, 2019, Vol. 10, (No. 41), pp: 4091-4106). In some embodiments, the remediated oil can comprise less than 4%, less than 2%, less than 0.25 g/g terpenes. In some embodiments, the remediated oil can comprise at least two types of terpenes.

Cannabinoids

In some embodiments, the at least one plant-extracted constituent is a bioactive constituent that is extracted from a cannabis plant. In some embodiments, the bioactive constituents are yet to be studied (e.g., isolated, characterized, given a name) for their pharmaceutical potential. In some embodiments, the rare cannabinoid is selected from the group consisting of CBN, CBL, CBC, Δ9-THC, CBGA, CBG, CBGA-C4, CBG-C4, CBGVA, CBGV, CBGOA, CBGO, CBGMA, CBGM, Sesqui-CBGA, Sesqui-CBG, THCA, THC, THCA-C4, THC-C4, THCVA, THCV, THCOA, THCO, THCMA, THCM, CBDA, CBD, CBDA-C4, CBD-C4, CBDVA, CBDV, CBDOA (CBDA-C1), CBDO (CBD-C1), CBDMA, CBDM, CBCA, CBC, CBCA-C4, CBC-C4, CBCVA, CBCV, CBCOA, CBCO, CBNA, CBN, CBNA-C4, CBN-C4, CBNVA, CBNV, CBNOA, CBNO, CBNA-8-OH, CBN-8-OH, CBNM, CBEA-B, CBEA-A, CBE, CBEVA, CBEV, CBNDA, CBND, CBNDVA, CBNDV, d8-THC, CBLA, CBL, CBLV, CBLVA, CBTA-1, CBT-1, CBTV-1, CBTA-3, CBT-3, CBTV-3, CBT-2, CBT, CBV, OTHC, CBCF, CBF, CBR, DCBF, cis-THC and triOH-THC. In some embodiments, the weight ratio of the minor cannabinoid to the major cannabinoid in the second refined oil or the purified oil is less than 1:5. In some embodiments, the rare cannabinoid or the bioactive constituent is one of the yet to be characterized. The rare cannabinoid or the bioactive constituent may be present in extracts of cannabis plants. In some embodiments, the rare cannabinoid is described in *A new ESI-LC/MS approach for comprehensive metabolic profiling of phytocannabinoids in cannabis* P. Berman et. al., Scientific Reports, 2018, 8, 14280.

In some embodiments, the extract stream of a first chromatography process is the feed to a second chromatography process, to a crystallization process, to a liquid/liquid extraction process, to a membrane filtration process, or to any combination thereof. In some embodiments, the raffinate or the extract of the second chromatography process is combined with the feed of the first chromatography process. In some embodiments, combining the feed of the first chromatography process and the raffinate or the extract of the second chromatography process increases the overall yield of the rare cannabinoid. In some embodiments, the mother liquor of the crystallization process is combined with the feed of the first chromatography process to increase the overall yield of the rare cannabinoid. In some embodiments, the extract or retentate of the liquid/liquid extraction or the filtration is combined with the feed of the first chromatography to increase the overall yield of the cannabinoids (e.g., rare cannabinoids).

The biomass (e.g., cannabis) may comprise at least about 1, 5, 10, 15, 17, 20, 25, 30, 40, 50, 60, 70, 80, 90, 97, 100, 125, 150, 200, or more cannabinoids (e.g., cannabinoid-types). The systems and methods described herein may extract, refine, remediate, or any combination thereof, at least about 1, 5, 10, 15, 17, 20, 25, 30, 40, 50, 60, 70, 80, 90, 97, 100, 125, 150, 200, or more cannabinoids. The systems and methods described herein may extract, refine, remediate, or any combination thereof, may remediate each cannabinoid present in the biomass (e.g., cannabis). The cannabinoids may be, for example, THCA, THC, CBDA, CBD, CBGA, CBG, CBDVA, CBDV, THCV, CBNA, CBN, CBCA, CBC, CBL, CBCV, CBT, or any derivative thereof. The cannabinoids may be rare cannabinoids. The cannabinoids may be present in cannabis. The cannabinoids may be derived from cannabinoids present in cannabis.

The cannabinoid-types present in the biomass may be identified with, for example, high-pressure liquid chromatography (HPLC) techniques (e.g., ultra-performance liquid chromatography (UPLC)) or mass spectroscopy techniques (e.g., liquid chromatography with tandem mass spectrometry (LC-MS/MS)). The methods to identify the cannabinoid-types present in the biomass may identify at least about 1, 5, 10, 15, 17, 20, 25, 30, 40, 50, 60, 70, 80, 90, 97, 100, 125, 150, 200, or more cannabinoids. The methods to identify the cannabinoids present in the biomass may identify from about 10 to about 100 cannabinoid-types. About 10 to 20 cannabinoid-types may be identified using HPLC techniques (e.g., UPLC). About 50 to 100 cannabinoid-types may be identified using mass spectroscopy techniques (e.g., LC-MS/MS).

For example, UPLC techniques may not identify each cannabinoid-type present in the biomass (e.g., cannabis). UPLC techniques may identify about 15 to 20 cannabinoid-types present in the biomass (e.g., cannabis). UPLC techniques may identify at least about 10%, 20%, 30%, 40%, 50%, 60%, 70%, 80%, 90%, or more cannabinoid-types present in the biomass (e.g., cannabis). UPLC techniques may identify at most about 90%, 80%, 70%, 60%, 50%, 40%, 30%, 20%, 10%, or less cannabinoid-types present in the biomass (e.g., cannabis). UPLC techniques may identify from about 10% to about 90%, about 10% to about 40%, or about 10% to about 20% of cannabinoid-types present in the biomass (e.g., cannabis).

For example, LC-MS/MS techniques may not identify each cannabinoid-type present in the biomass (e.g., cannabis). LC-MS/MS techniques may identify about 50 to about 100 cannabinoid-types present in the biomass (e.g., cannabis). LC-MS/MS techniques may identify at least about 10%, 20%, 30%, 40%, 50%, 60%, 70%, 80%, 90%, 95%, or more cannabinoid-types present in the biomass (e.g., cannabis). LC-MS/MS techniques may identify at most about 95%, 90%, 80%, 70%, 60%, 50%, 40%, 30%, 20%, 10%, or less cannabinoid-types present in the biomass (e.g., cannabis). LC-MS/MS techniques may identify from about 10% to about 95%, about 50% to about 95%, or about 80% to about 95% of cannabinoid-types present in the biomass (e.g., cannabis).

Scale

The systems described herein may be configured to process biomass at industrial or semi-industrial scale. The methods described herein may be performed at industrial or semi-industrial scale. The biomass, or extracts thereof, may be processed at a scale that is practical for commercial use. The systems and methods described herein may be produce constituents derived from biomass at a scale that can provide, for example, a local supply, a national supply, or a global supply of the constituents derived from the biomass. The systems and methods described herein may process at least about 50 kilograms/day (kg/day), 100 kg/day, 250 kg/day, 500 kg/day, 1,000 kg/day, 5,000 kg/day, 10,000 kg/day, 50,000 kg/day, or more of biomass. The systems and methods described herein may process at most about 50,000 kg/day, 10,000 kg/day, 5,000 kg/day, 1,000 kg/day, 500 kg/day, 250 kg/day, 100 kg/day, 50 kg/day, or less of biomass. The systems and methods described herein may process from about 50 kg/day to about 50,000 kg/day, about 500 to about 10,000 kg/day, or about 1,000 to about 5,000 kg/day. The systems and methods described herein may produce at least about 0.5 kg/day, 1 kg/day, 5 kg/day, 10 kg/day, 50 kg/day, 100 kg/day, 250 kg/day, 500 kg/day, 1,000 kg/day, 10,000 kg/day, or more of the constituents derived from the biomass. The systems and methods described herein may produce at most about 10,000 kg/day, 1,000 kg/day, 500 kg/day, 250 kg/day, 100 kg/day, 50 kg/day, 10 kg/day, 5 kg/day, 1 kg/day, 0.5 kg/day, or more of the constituents derived from the biomass. The systems and methods described herein may produce from about 0.5 kg/day to about 10,000 kg/day, about 1 kg/day to about 1,000 kg/day, or about 10 kg/day to about 500 kg/day of the constituents derived from the biomass. Fewer rare cannabinoids in the biomass (e.g., 0.5 kg/day) may be produced per day than abundant cannabinoids in the biomass (e.g., 500 kg/day).

EXAMPLES

Example 1: HPLC Method for the Analysis of Cannabinoids

Figure 11A:
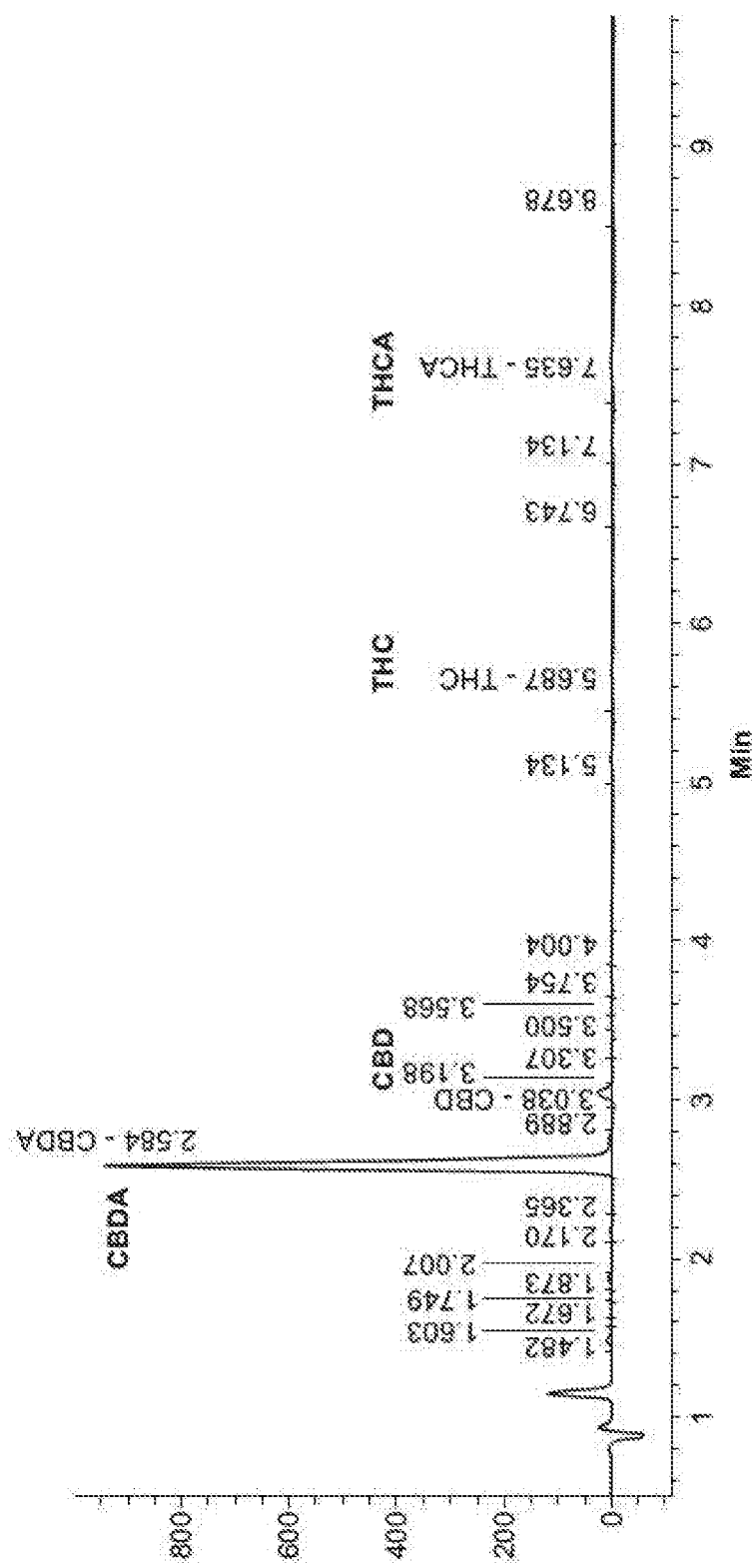
FIG. 11A depicts a HPLC chromatogram of a refined extract, detecting cannabinoids.

Process samples are diluted 1000-fold with 25:75 v/v methanol:acetonitrile, filtered and injected (54) onto a Raptor ARC-18 column (cat. #9314A65), 150 mm×4.6 mm ID. Elution done at 30° C., using isocratic mixture of 25% A:75% B, where A comprises 5 mM ammonium formate, 0.1% formic acid in water; B comprises Acetonitrile, 0.1% formic acid. CBDA, CBD, THCA and THC are calibrated against their standards, purchased from Restek. A typical chromatogram is shown in FIG. 11A.

Example 2: Characterization of Refined Extract by GCMS

Figure 11B:
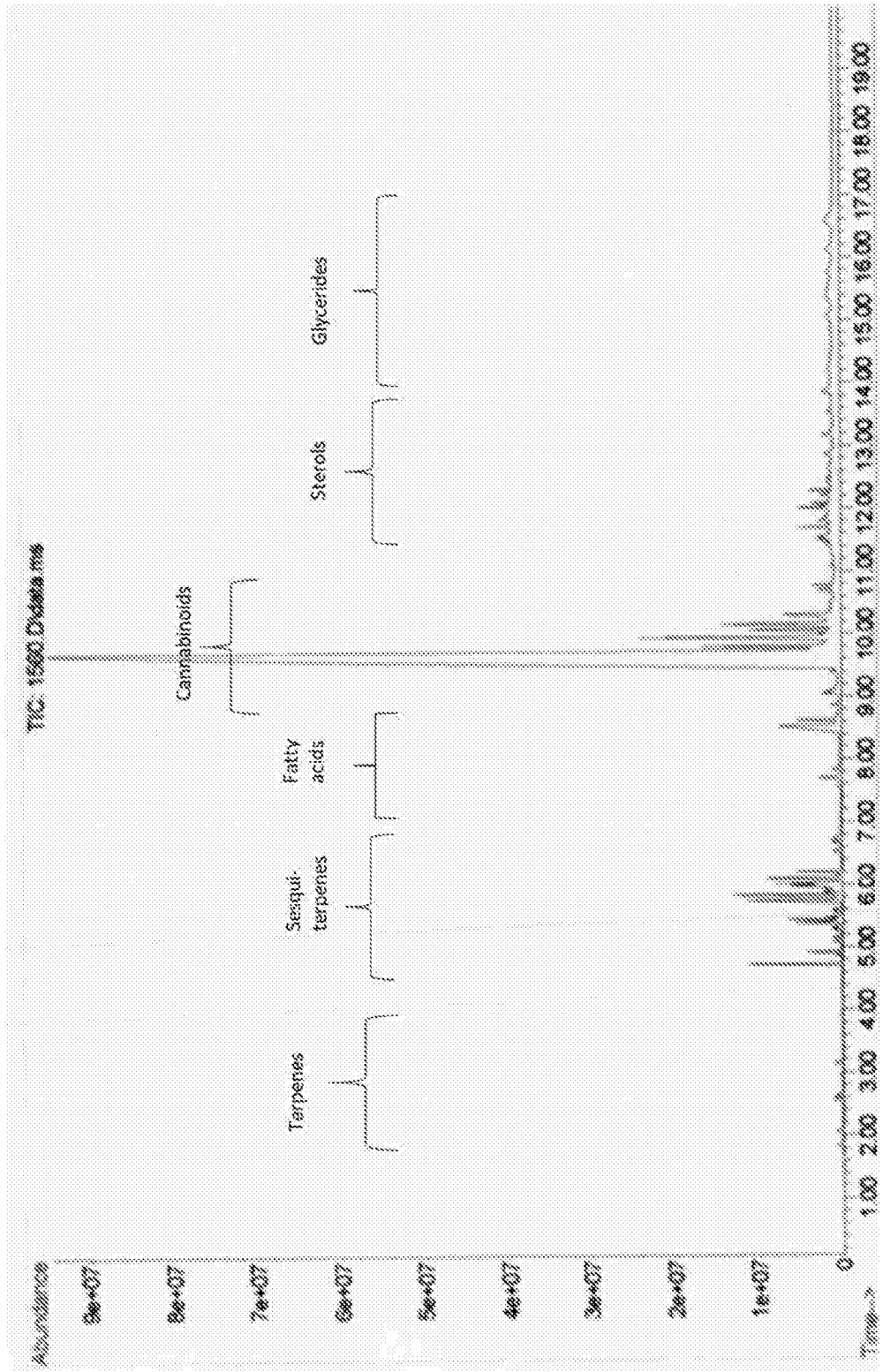
FIG. 11B depicts a chromatogram obtained by GCMS with Cold EI detector of a first refined extract of hemp, which was refined according to a method of this disclosure.
Figure 11C:
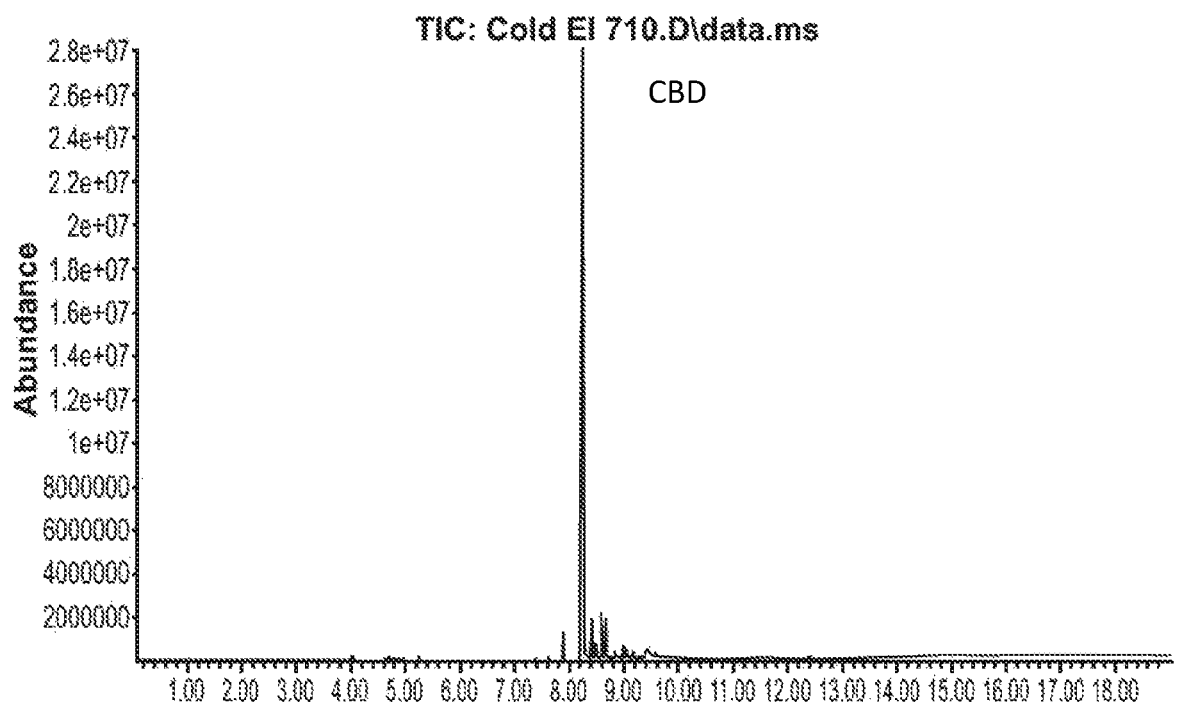
FIG. 11C depicts a chromatogram obtained by GCMS with Cold EI detector of a second refined extract of hemp, which was refined according to a method of this disclosure. The lower panel depicts the MS spectrum of the major peak, identified as CBD.
Figure 11C:
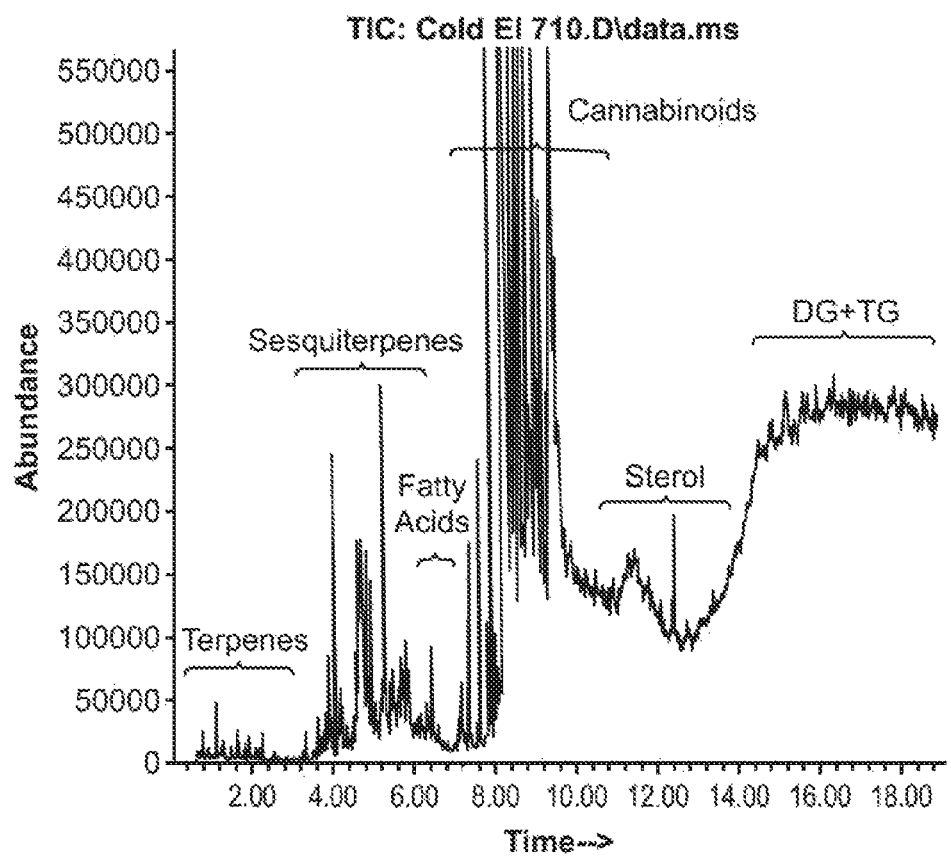
Figure 11D:
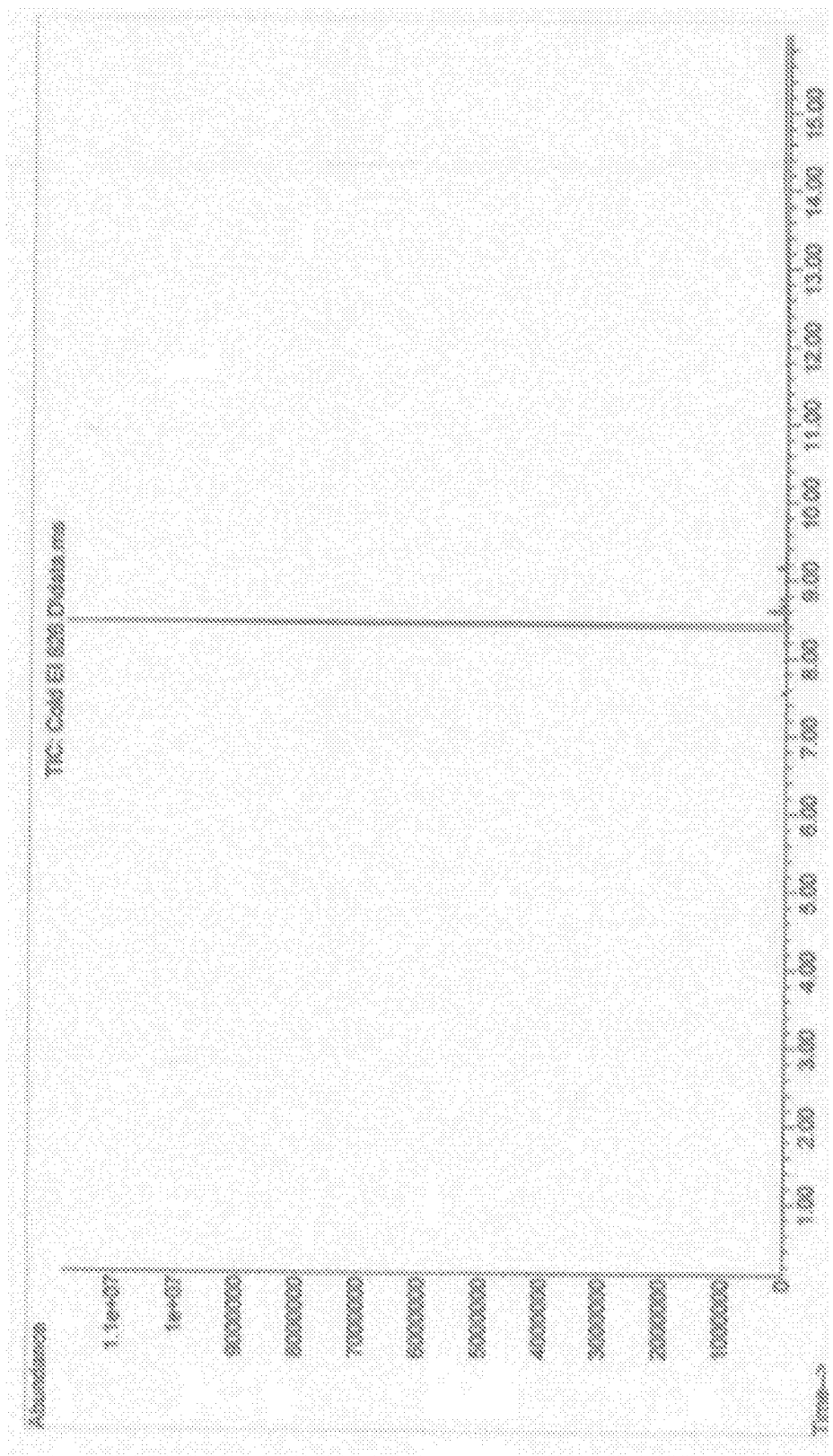
FIG. 11D depicts a HPLC chromatogram obtained by GCMS with Cold EI detector of a purified oil extracted from hemp, which was refined according to a method of this disclosure.
Figure 11E:
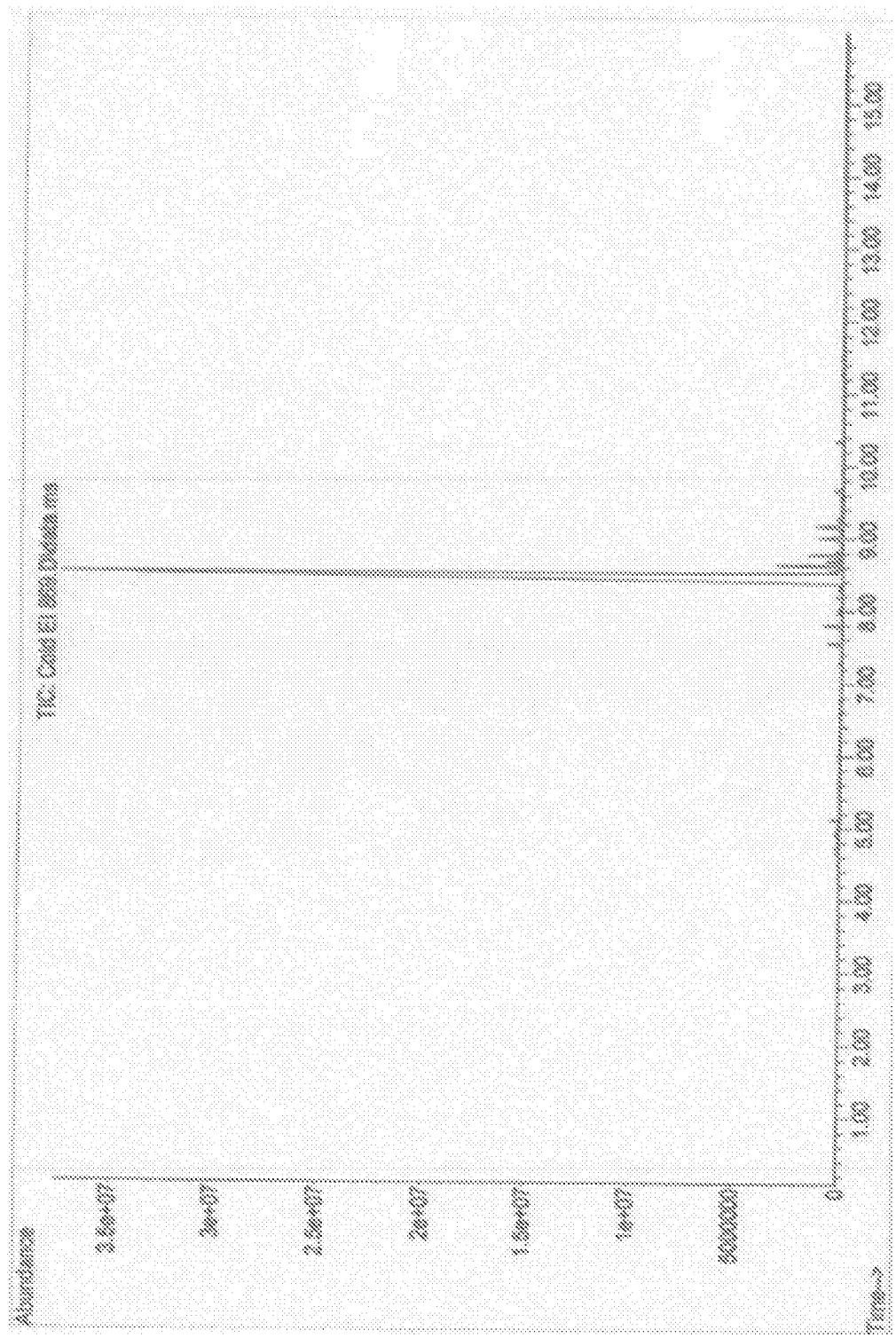
FIG. 11E depicts a chromatogram obtained by GCMS with Cold EI detector of a purified oil extracted from hemp, which was refined according to a method of this disclosure.

Samples are characterized by 5977-SMB GC-MS with Cold EI detector, which enables the detection of species having molecular weight in the range 400-1000 as their molecular ions (A. Amirav et. al., Rapid Communications in Mass Spectrometry 29(21):1954-1960, 2015). This method is highly suitable for identifying unknowns against the NIST library. Chromatograms obtained for the first refined extract (FIG. 11B), the second refined extract (FIG. 11C), and for purified oil (FIG. 11D and FIG. 11E) as disclosed herein.

Cannabinoids are decarboxylated at the injector, thus all cannabinoids are present in their decarboxylated form.

Example 3: Characterization of Refined Extract by HPLC

Figure 13:
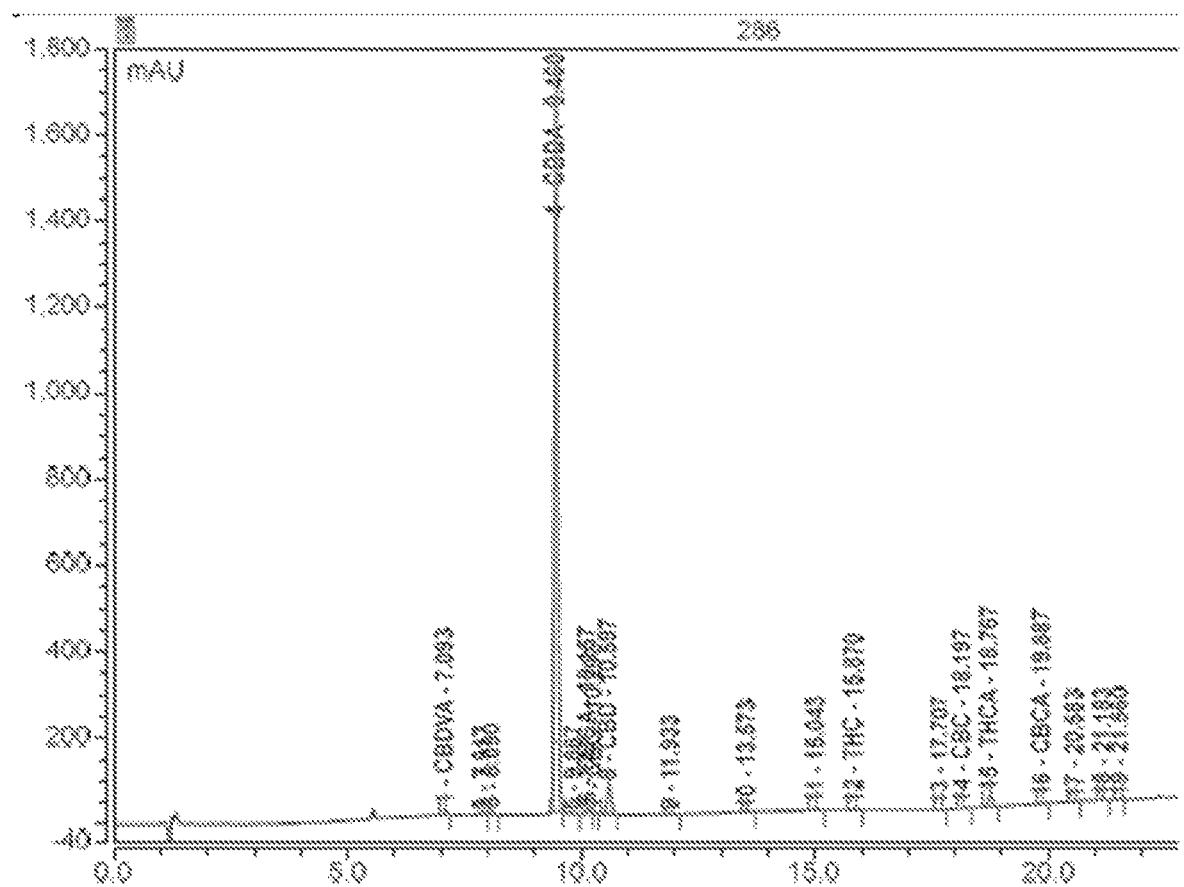
FIG. 13 depicts a HPLC chromatogram of a refined extract, detecting cannabinoids.

A sample of refined hemp extract, prepared according to example 4, was characterized by UPLC with UV detection. The method is suitable for quantification of multiple cannabinoids. The HPLC chromatogram is depicted in FIG. 13, the quantitative results are summarized in Table 1. The analysis quantified a total of 81.6% of the sample weight as cannabinoids. As expected, the cannabinoids comprised predominantly CBDA (89.1%), with small amounts of CBD, THCA, THC, CBCA, CBC, CBGA, CBG and CBDVA. While being highly refined, the sample has too high THCA and THC to comply with "THC free" limit of 0.3%, as regulations of many states require. To comply with such regulations further processing is performed, for example crystallizing the CBDA or chromatographic separation to enrich the composition with CBDA and lower THCA/THC concentration.

TABLE 1 cannabinoid analysis of refined samples

| Cannbinoid | % wt/wt | % wt/TC |
|---|---|---|
| THCA | 1.61 | 1.97 |
| THC | 0.40 | 0.49 |
| CBDA | 72.70 | 89.11 |
| CBD | 4.29 | 5.26 |
| CBGA | 0.65 | 0.80 |
| CBG | 0.18 | 0.22 |
| CBDVA | 0.44 | 0.54 |
| CBDV | ND | ND |
| THCV | ND | ND |
| CBNA | ND | ND |
| CBN | ND | ND |
| CBCA | 1.08 | 1.32 |
| CBC | 0.23 | 0.28 |
| CBL | ND | ND |
| CBCV | ND | ND |
| D8-THC | ND | ND |
| Cannbicitran | ND | ND |
| TC | 81.58 | |

Example 4: Extraction and Refining of Hemp 0.5 kg of fresh hemp or hemp pellets were ground in a grinder. The ground biomass was mixed with ×10 wt of water-saturated ethyl acetate for 20 at 15-20° C. The slurry was filtered, the filtrate was collected, and the solids were extracted once more by mixing again with a second portion of fresh solvent under the same conditions. Both filtrates were combined. The solution was warmed to ~45° C. and passed through two sequential GAC columns at flow rate of about 4 BV/h. The solvent was removed by evaporation to about 0.07 kg crude oil. The crude oil was mixed with ×10 water-saturated ethyl acetate. About 0.02 g of lysine were added per kg crude oil, the solution was stirred for about 20 min. at 60° C. Clay mixture was added as 10% wt of the crude oil wt, the mixture comprising 50% wt perlite; 40% bentonite; 10% Florisil®, the slurry was stirred for another 15 min. at 60° C. Water was added to the mixture, 20% wt/wt, optionally with 1-2% NaCl or sodium acetate, mixed for about 2 min. at 60° C. and filtered. The filtrate was allowed to separate to phases, the aqueous phase was removed. The organic phase was passed through a column loaded with Purolite C115E, 1:1 $Na^+$:$H^+$ at 45° C., 4 BV/h. Activated carbon was added to the solution and mixed at 45° C. for 15 min. The slurry was filtered, the filtrated evaporated at 60-70° C. under vacuum, a solution of 1-2% sodium acetate was added while evaporating to ensure full removal of the solvent. The remaining hot solution was collected, allowed to separate into phases, the aqueous phases was removed, and the refined oil collected.

Figure 12A:
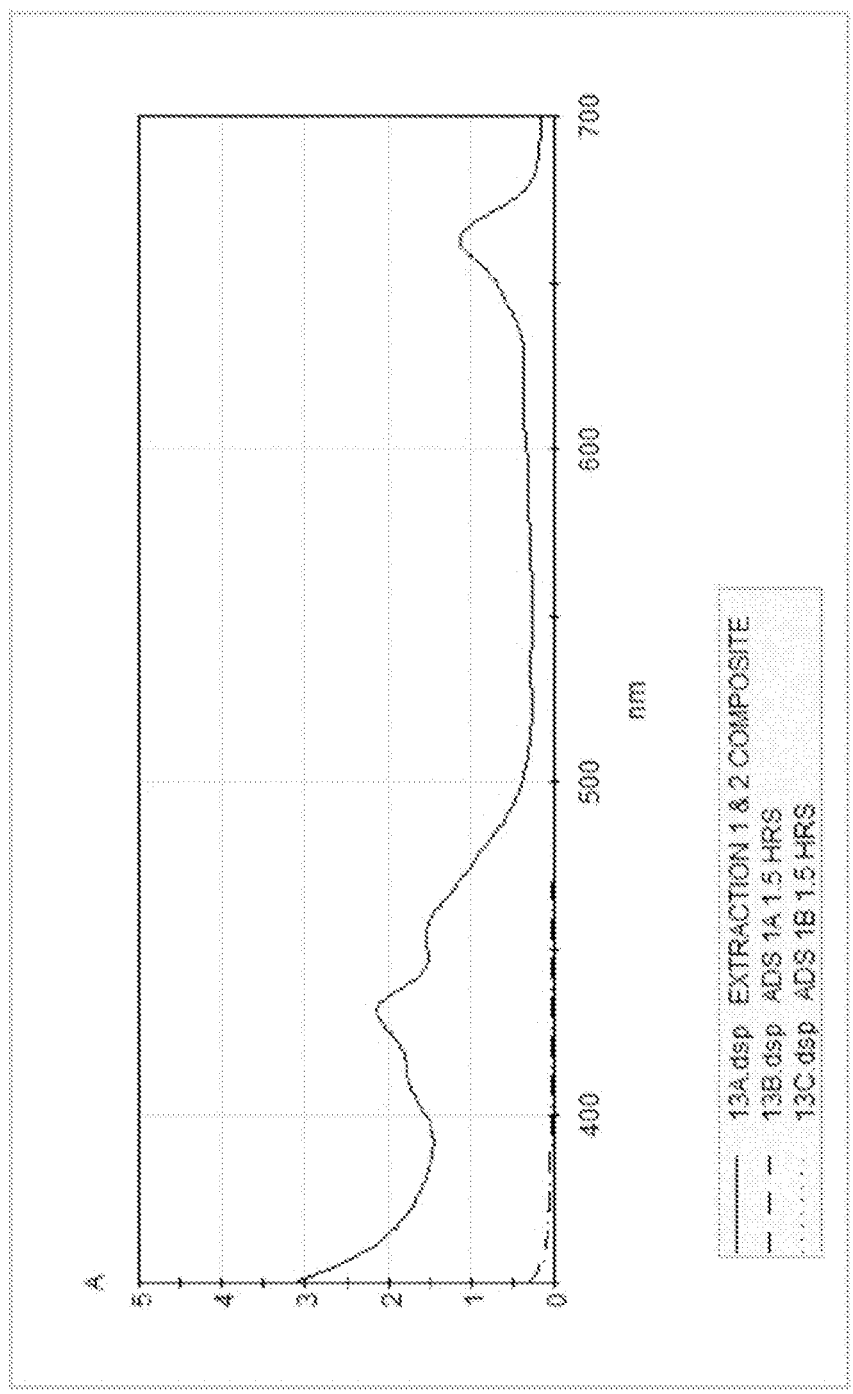
FIG. 12A depicts the UV-VIS spectrum of crude oil (A) and first refined oil (B), extracted from Oregon Hemp

Example 5: Extraction and Refining Dry of Hemp 2.5 kg of 10% moisture hemp mixed for 10 minutes in 20-liter saturated ethyl acetate at ~20° C. and filtered. Solids remixed in 20 liters of ethyl acetate for 10 minutes and filtered. Filtrates were mixed and passed through two columns in series of GAC. The UV-VIS spectra of the solution before contacting with GAC, after columns 1 and after the second column is shown in FIG. 12A. Effective removal of colored matter was observed. Clarified filtrate was concentrated to 1.5 liters. Material was processed to remove fatty acids and sugars; the mix was then deionized, and polish filtered. Final concentration removed the solvent.

Figure 12B:
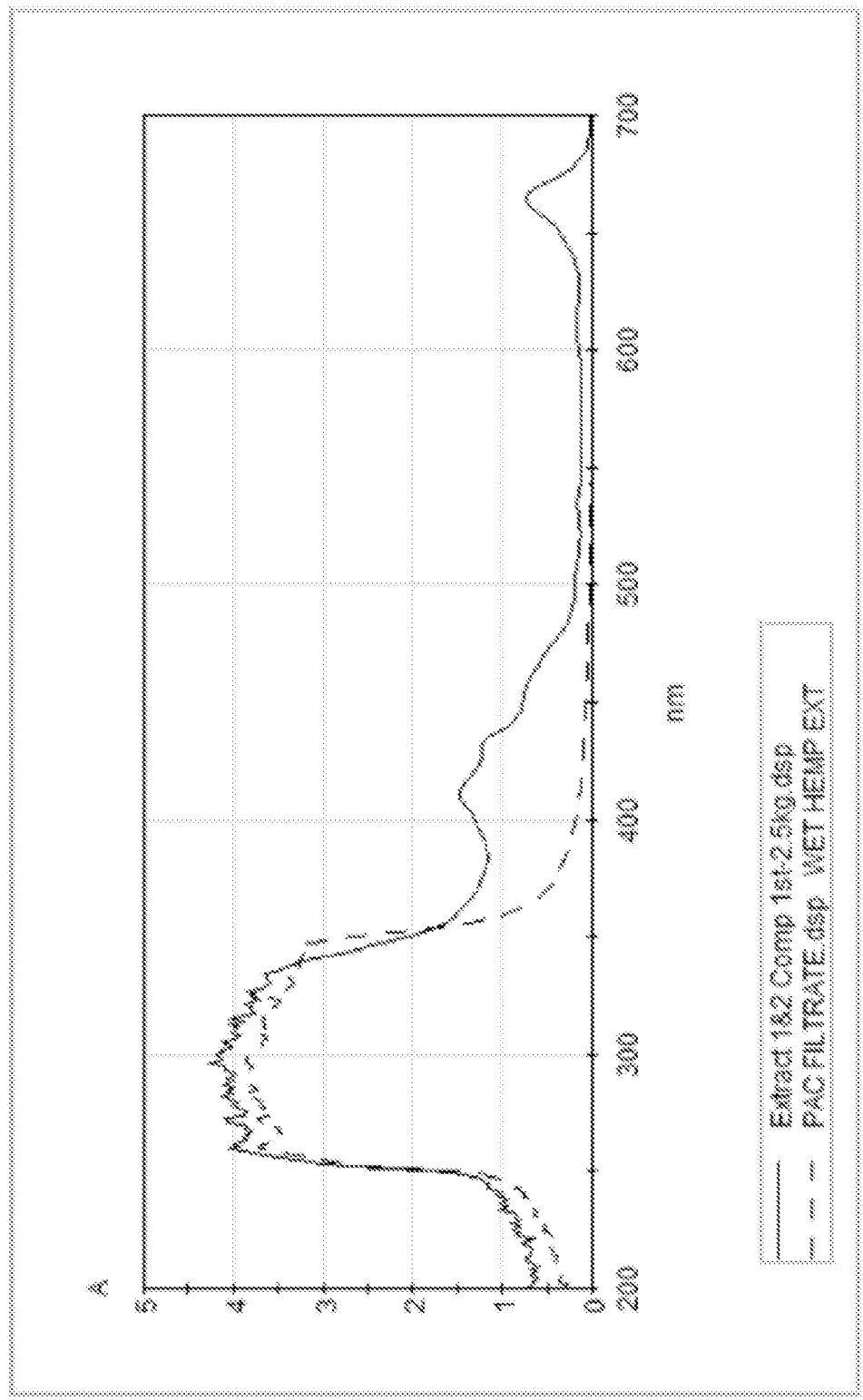
FIG. 12B depicts the UV-VIS spectrum of crude oil (solid line) and first refined oil (dotted line), extracted from Illinois wet hemp.

Example 6: Extraction and Refining Wet of Hemp 5.0 kg of 45% moisture hemp was mixed for 10 minutes in 20-liter saturated ethyl acetate at –20 C and filtered. Solids remixed in 20 liters ethyl acetate for 10 minutes and filtered. Filtrates were combined. Filtrate was concentrated to 10 liters and BG HHM carbon (Calgon) was added and filtered. The UV-VIS spectra of the solution before contacting with PAC is presented in FIG. 12B. Effective removal of colored matter was observed. Clarified filtrate was concentrated to 1.5 liters. Material was processed to remove fatty acids and sugars; the mix was then deionized, and polish filtered. Final concentration removed the solvent.

Example 7: Characterization of the Extracted Crude Oil

The starting biomass, the spent biomass after extraction and the crude oil were evaluated for terpene concentration by a certified service laboratory, Eurofins Food Integrity and Innovation, the results are summarized in Table 2.

TABLE 2 determination of terpenes in the raw biomass, spent biomass at the extract.

| | mg/100g | | |
|---|---|---|---|
| | Raw Biomass | Spent Biomass | Extract 2 Biomass |
| (–)-alpha-Bisabolol | 42 | <1.0 | 150 |
| Camphene | <1.0 | <1.0 | 4.2 |
| (1S)-(+)-3-Carene | <1.0 | <1.0 | <1.0 |
| beta-Caryophyllene | 69 | 7.7 | 950 |
| p-Cymene | <1.0 | <1.0 | <1.0 |
| Eucalypton | <1.0 | <1.0 | <1.0 |
| alpha-Humulene (alpha-Caryophyllene) | 28 | <5.0 | 320 |
| (–)-Isopulegol | <1.0 | <1.0 | <1.0 |
| (R)-(+30)-Limonene | 4.6 | 1.4 | 180 |
| Linallol | 10 | <1.0 | 120 |
| beta-Myrcene | 27 | 13 | 1100 |
| (E)-b-Ocimene | 2.2 | <0.60 | 28 |
| (Z)-b-Ocimene | 0.51 | <0.30 | 8 |
| alpha-Pinene | 6.8 | 1.8 | 66 |
| beta-Pinene | 3.7 | 1 | 58 |

TABLE 2-continued determination of terpenes in the raw biomass, spent biomass at the extract.

| | mg/100g | | |
|---|---|---|---|
| | Raw Biomass | Spent Biomass | Extract 2 Biomass |
| alpha-Terpinene | <1.0 | <1.0 | 1.3 |
| gamma-Terpinene | <1.0 | <1.0 | 1 |
| Terpinolene | <1.0 | <1.0 | 2.3 |

It is observed that ~85% of the terpenes present in the feed biomass are effectively extracted into the extracted oil. Terpenes comprise about 3% wt/wt of the refined oil.

Example 8: Characterization of Refined Oil—Impurity Profile

Figure 14:
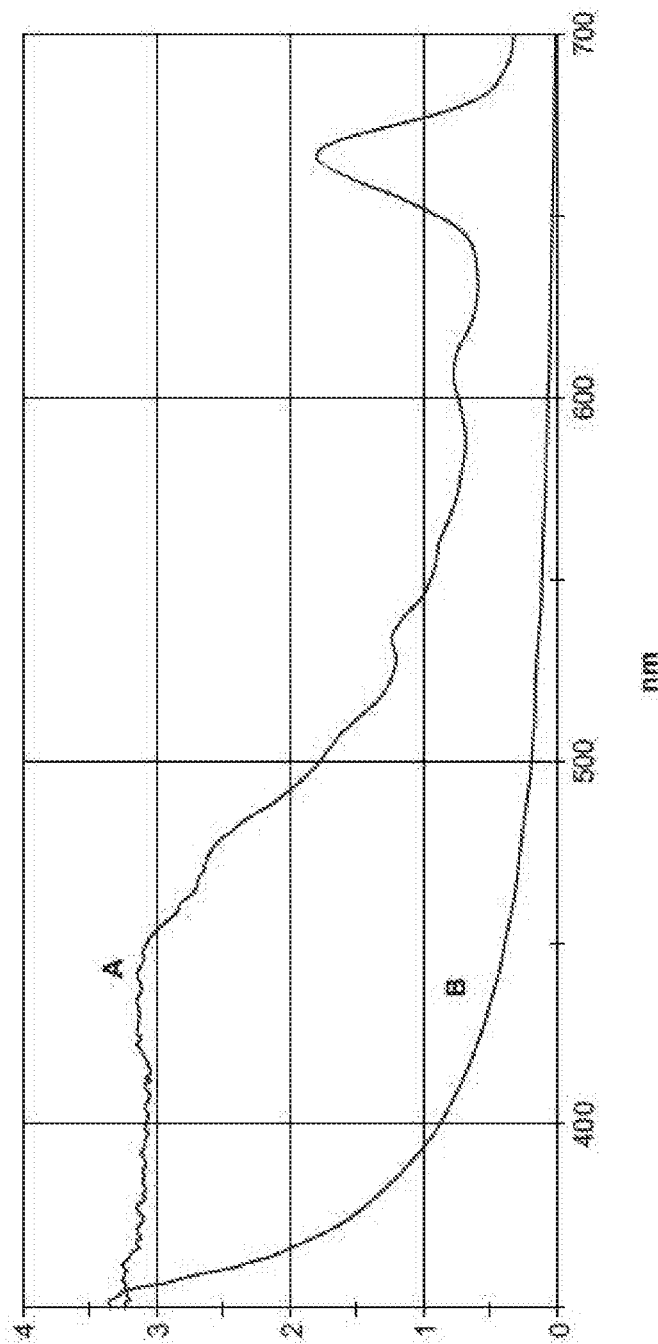
FIG. 14 depicts the UV-VIS spectrum of the crude oil (A) and the refined oil (B).

A qualitative measure to the purity of the refined oil is provided by its appearance—light yellow solution. FIG. 14 depicts the UV-VIS of the crude oil (A) and the refined oil (B). The composition and purity were further characterized by several methods.

Figure 15A:
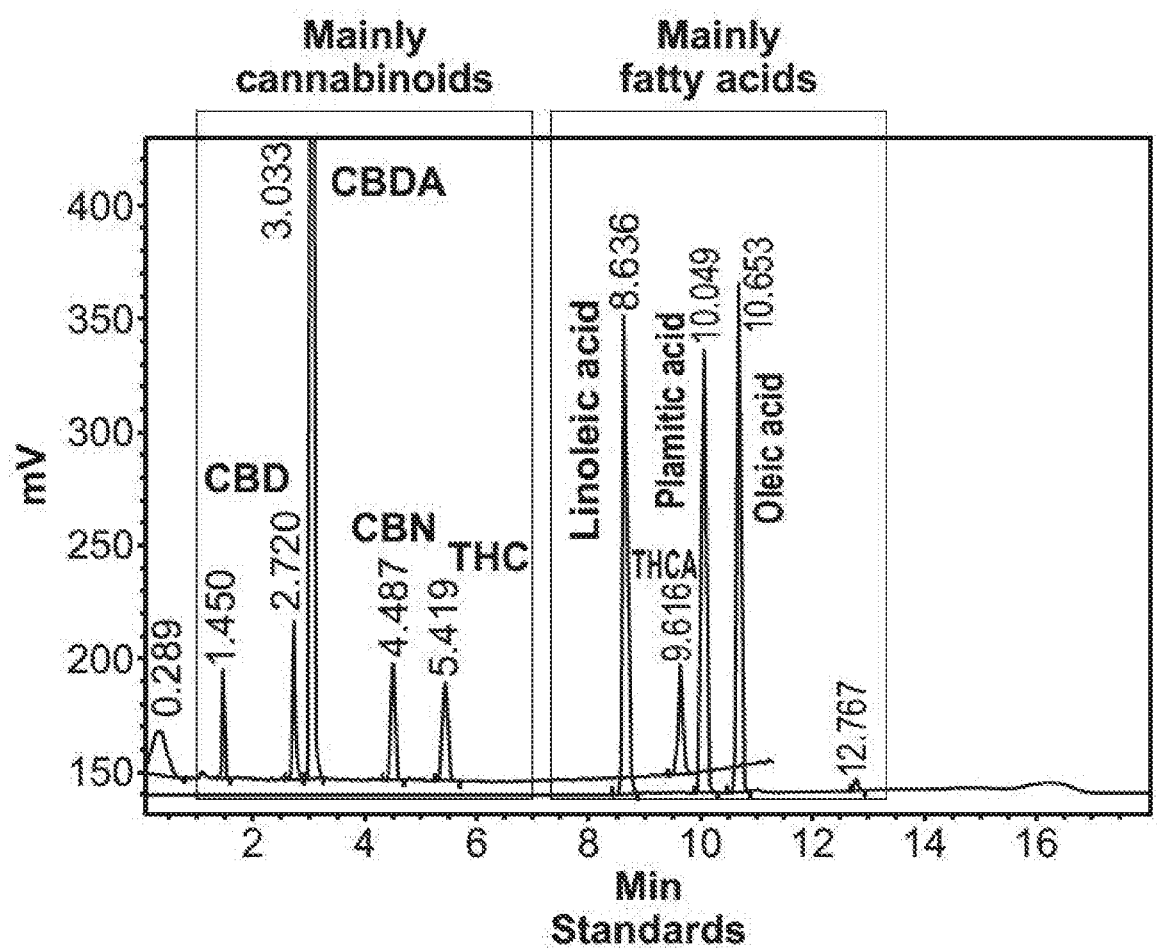
FIG. 15 depicts HPLC chromatograms (FIG. 15A) of standards and refined extract (FIG. 15B), detecting cannabinoids and fatty acids.
Figure 15B:
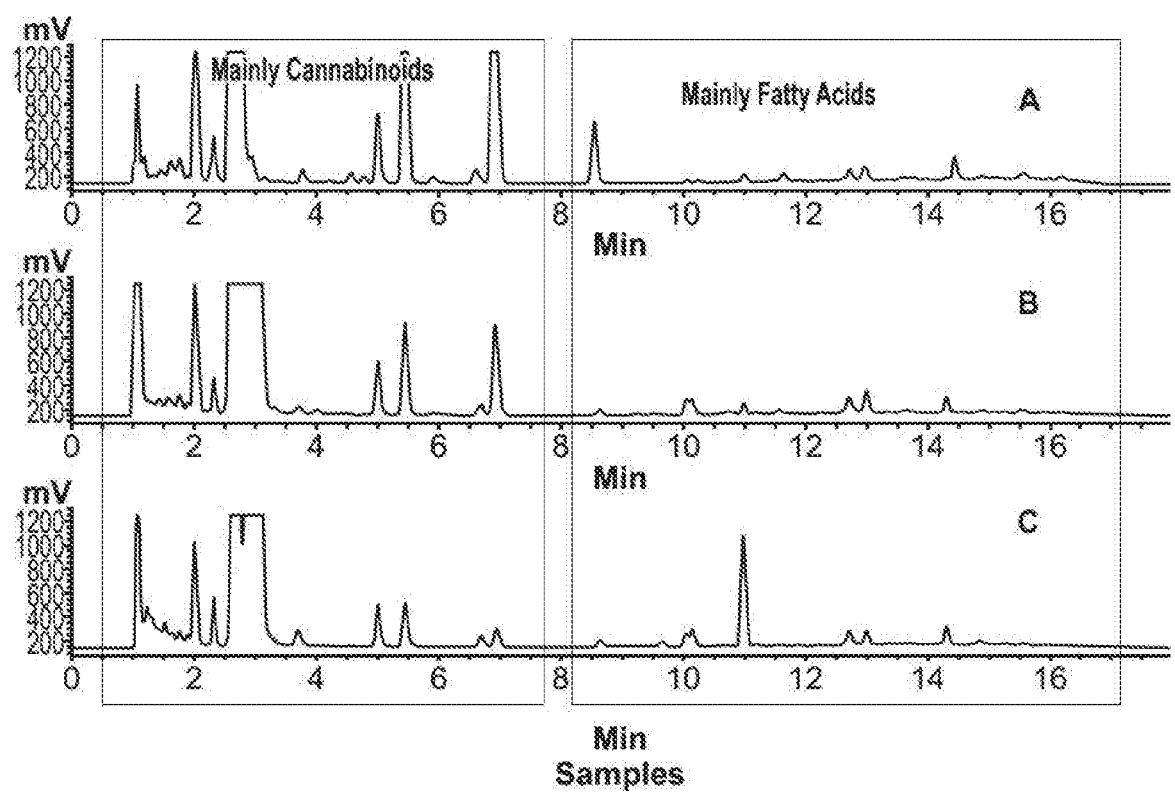

Fatty Acid Content:

FA content was evaluated by HPLC (Varian Prostar, RI detector), using a Thermo Scientific ODS Hypersil column, 150×4.6 mm, 3 µL eluent: 80:20 acetonitrile: 0.1% acetic acid/water, 0.5 ml/min, 25° C. The oil sample was diluted ×1000 with methanol, filtered through a 0.22 µm Nylon filter, 10 µL injected. FIG. 15 depicts comparative chromatograms: FIG. 15A is a typical oil obtained by a comparative ethanol extraction process; FIG. 15B is a sample of refined oil prepared according to example 8; C is a sample prepared according to example 8 but omitting the step of adding lysine in the refining sequence. The chromatograms demonstrate the efficiency of removing FA by adding lysine in the refining process. The amount of residual FA in sample B was determined to be 0.25% wt/wt linoleic acid; 0.23% wt/wt palmitic acid; 0.16% oleic acid, which is about 0.5 to 0.25 of the residue remaining without this refining step.

Figure 16:
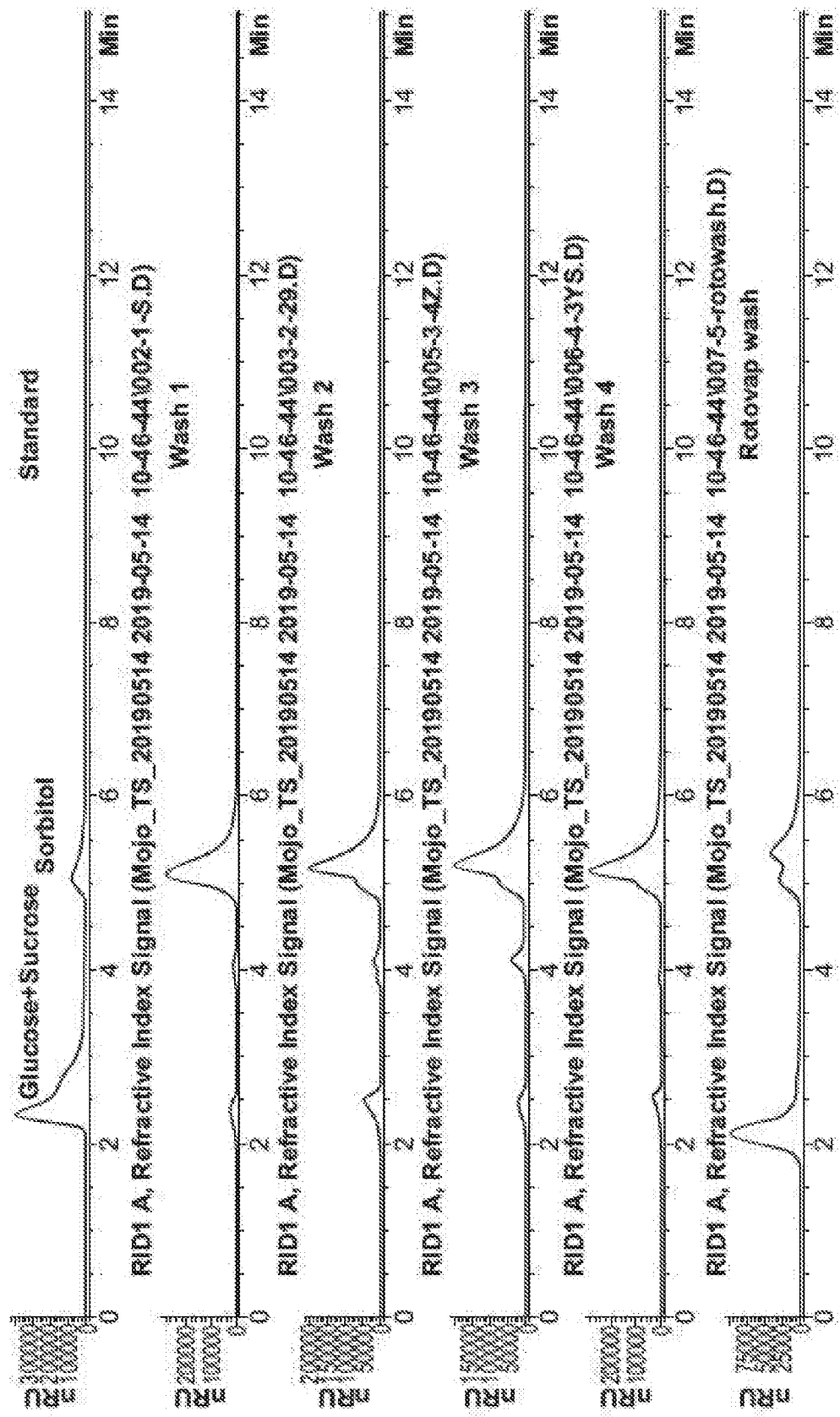
FIG. 16 depicts HPLC chromatograms of refined extract, detecting saccharides.

Sugar removal: the effectiveness of sugars removal from the oil was evaluated by determining the amount of sugars extracted into the separated aqueous phases in the course of the refining process. Sugars were analyzed by HPLC, using a Bio-Rad Fast Carbohydrate Analysis column—HPAP, 100×7.8 mm, using water as eluent, 0.6 ml/min, 80° C., 10 µL injected. FIG. 16 depicts chromatograms of sugar analysis: The top chromatograph is a standards injection (glucose, sucrose, sorbitol, ~1% each); the chromatograms below are runs of aqueous solutions separated at liquid/liquid phase separation steps of example 8, the bottom chromatogram is the aqueous phase separated at the evaporation of the refined oil. It is clear that each contact with an aqueous phase removes some sugars from the oil.

Heavy metals: samples of feed biomass, spent biomass and refined oil were analyzed by Eurofins Food Integrity and Innovation according to Official Methods of Analysis, Method 2011.19 and 993.14, AOAC INTERNATIONAL, (Modified). Pequette, L. H., Szabo, A., Thompson, J. J., "Simultaneous Determination of Chromium, Selenium, and Molybdenum in Nutritional Products by Inductively Coupled Plasma/Mass Spectrometry: Single-Laboratory Validation," Journal of AOAC International, 94(4): 1240-1252 (2011), the results are summarized in Table 3.

TABLE 3 analysis of heavy metals in biomass and refined oil

| | parts per billion (ppb) | | |
|---|---|---|---|
| metal | Raw Biomass | Spent Biomass | Final oil |
| Arsenic | 75.3 | 48.2 | <10 |
| Cadmium | 384 | 280 | <5 |
| Lead | 105 | 72.1 | 26.1 |
| Mercury | 6.2 | <5 | <5 |

The results indicate ~30% extraction of the heavy metals from the biomass, with removal of ~97%. It is expected that this value can be further optimized to bring all heavy metals to bellow the regulatory requirements.

Microbiology:

the refined oil was characterized by the same laboratory for yeast and mold according to UMN2K-Yeast-BAM Chapter 18, Method Reference: FDA BAM Chapter 18 to show Yeast <10 cfu/g; Mold <10 cfu/g.

Pesticides:

raw biomass, spent biomass and the refined oil was characterized by the same laboratory according to Multi-Residue Analysis for hemp products of 60+ compounds: Official Methods of Analysis, AOAC Official Method 2007.01, Pesticide Residues in Foods by Acetonitrile Extraction and Partitioning with Magnesium Sulfate, AOAC INTERNATIONAL (modified). CEN Standard Method EN 15662: Food of plant origin—Determination of pesticide residues using GC-MS and/or LC-MS/MS following acetonitrile extraction/partitioning and clean-up by dispersive SPE—QuEChERS method. No residual pesticides were found in any of the samples (e.g., <0.05 mg/kg).

Example 9: HPLC Analysis of the Crude Extract

A sample of the cannabis plant and samples of crude extract (i.e. without further refining) NS3 and NS4 were analyzed at CannaSoul Ltd. for cannabinoid content. The results are summarized in Table 4. It is observed that THCA is the major cannabinoid detected both in the feed plant material and in the crude extracted product. As expected, the mild conditions applied cause very little decarboxylation, hence the extract composition virtually mirrors the plant composition with respect to cannabinoids.

TABLE 4

HPLC analysis* of the feed cannabis plant and crude extracted samples

| Sample | THCA (wt/wt %) | THC (wt/wt %) | CBDA (wt/wt %) | CBGA (wt/wt %) | CBG (wt/wt %) | Total cannabinoids/ extract |
|---|---|---|---|---|---|---|
| Feed plant | 9.724 | 0.338 | 0.042 | 0.332 | 0.045 | |
| NS3 | 53.047 | 1.776 | 0.228 | 1.638 | 0.236 | 57 |
| NS3 % extracte | 107 | 103 | 106 | 96 | 103 | |
| NS4 | 45.626 | 1.881 | 0.197 | 1.477 | 0.216 | 49 |
| NS4 % extracte | 99 | 117 | 98 | 93 | 101 | |

*CBD, CBDV, THCV, CBN, CBC, CBL, D8-THC were not detected in this plant.

Example 11: 3$^{rd}$ Refining of Extracted Hemp

The product of example 5 was further refined by short path distillation utilizing commercially available setups, for example from Root Sciences VTA and POPE. Two distillation cuts were collected: terpene cut and cannabinoids cut. The composition of the cannabinoid cut was analyzed, the results are summarized in table 5. In some of the experiments triolein was added to the distillation bottom at 10-20% with respect to the distillation feed. GCMS of the collected cannabinoid fractions demonstrates that triolein is not distilled or decomposed and remains with the distillation residue bottom. Harsher distillation conditions (i.e. higher temperature/lower vacuum) results in higher purity of cannabinoids, but lower overall yield.

TABLE 5

| distillation conditions and products | | |
| --- | --- | --- |
| Conditions | 1) 135° C., 2200 mTorr 2) 160-180° C., 80 mTorr (FIG. 11E) | 1) 140-160° C., 167 mTorr 2) 170° C., 64 mTorr (FIG. 11D) |
| Sesquiterpenes | 2.65% | 0.13% |
| Fatty acids | 0.15% | 0.28% |
| CBD | 87.0% | 87.7% |
| Total cannabinoids | 90.7% | >99% |
| Hydrocarbon | 1.0% | 0.00% |
| Steroids & sterols | 1.0% | 0.00% |
| Others | 4.4% | <1% |

Example 12A: Remediation Method of Purified Cannabis Oil to Remove THC

A sequence suitable for remediating purified cannabis oil to produce a product having THC <0.3% using a reverse phase adsorbent Chromalite® PCG600M in a dual desorbent mode is shown in table 6. Both desorbents comprise water-ethanol-hexane at the following polarities: D1—0.660; D2—0.033. Chromalite PCG600M was used as solid phase adsorbent.

TABLE 6A

| SSMB sequence for the remediation of purified oil using a dual desorbent mode | |
| --- | --- |
| Step | DD/SSMB |
| Step 1 (D2 to Extract; Feed to Raffinate) | |
| Step 1 Time | 673.5 seconds |
| Raffinate Flow | 1.71 ml/min |
| Extract Flow | 12.8 ml/min |
| Step 2 (D1 to Extract) | |
| Step 2 Time | 121.7 seconds |
| Extract Flow | 32.5 ml/min |
| Raffinate Flow | — |
| Step 3 (D1 to Raffinate) | |
| Step 3 Time | 112.3 seconds |
| Extract Flow | — |
| Raffinate Flow | 10.2 ml/min |
| Step 4 (Recycle) | |
| Step 4 Time | 1514.2 seconds |
| Recycle Flow | 10.2 ml/min |
| Results | |
| Purity - CBD/THC | >97%/<1000 ppm |
| Recovery - CBD | >85% |
| Desorb to Feed Ratio | 12.4 |
| Total Step Time | 40.36 minutes |

Example 12B: Remediation Method of Purified Cannabis Oil to Remove THC

A sequence suitable for remediating purified cannabis oil to produce a product having THC <0.3% using a reverse phase adsorbent Chromalite® PCG600M in a dual desorbent mode is shown in table 6B. Both desorbents comprise water-ethanol-pentane at the following polarities: D1—0.683; D2—0.045. Chromalite PCG600M was used as solid phase adsorbent.

TABLE 6B

| SSMB sequence for the remediation of purified oil using a dual desorbent mode | |
| --- | --- |
| Step | DD/SSMB |
| Step 1 (D1 to Extract; Feed to Raffinate) | |
| Step 1 Time | 377.5 seconds |
| Raffinate Flow | 3.1 ml/min |
| Extract Flow | 12.0 ml/min |
| Step 2 (D2 to Extract) | |
| Step 2 Time | 778.6 seconds |
| Extract Flow | 16.0 ml/min |
| Raffinate Flow | — |
| Step 3 (D1 to Extract) | |
| Step 3 Time | 424.7 seconds |
| Extract Flow | 16.0 ml/min |
| Raffinate Flow | — |
| Step 4 (D1 to Raffinate) | |
| Step 4 Time | 132.3 seconds |
| Extract Flow | — |
| Raffinate Flow | 10.2 ml/min |
| Step 5 (recycle) | |
| Step 5 Time | 929.4 seconds |
| Recycle flow | 10.2 ml/min |
| Results | |
| Purity - CBD/THC | >97%/<1000 ppm |
| Recovery - CBD | >90% |
| Desorb to Feed Ratio | 21.8 |
| Total Step Time | 44.00 minutes |

Example 13: Remediation Results of Purified Cannabis Oil to Remove THC

Figure 17:
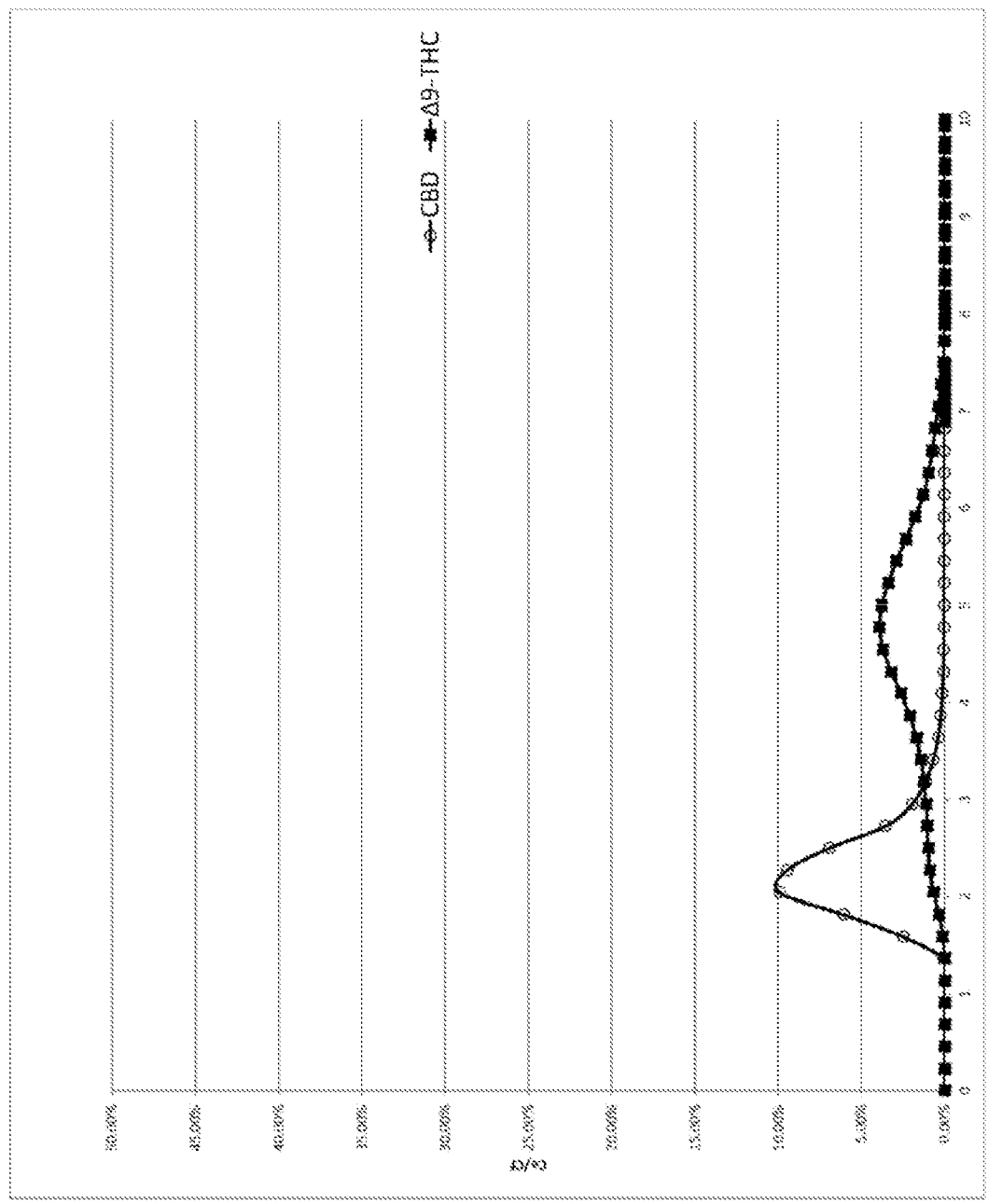
FIG. 17 depicts a pulse test of loading purified hemp oil onto a Chromalite® PCG600M resin and ethanol/water (polarity of 0.696) as the desorbent.

The ability to remove THC from refined oil by reverse phase chromatography was evaluated by pulse test: refined oil was mixed 1:1 by weight with a D1 comprising ethanol/water at polarity of 0.696. 19.8 ml were loaded onto a column packed with Chromalite® PCG600M and eluted with D1 (3.8 ml/min·cm$^2$) at 68° F. Fractions were collected and analyzed by the method of example 1 for cannabinoids. FIG. 17 shows the concentration of CBD and THC relative to their concentration in the feed.

Example 14: Remediation Results of Purified Cannabis Oil to Remove THC

Figure 18:
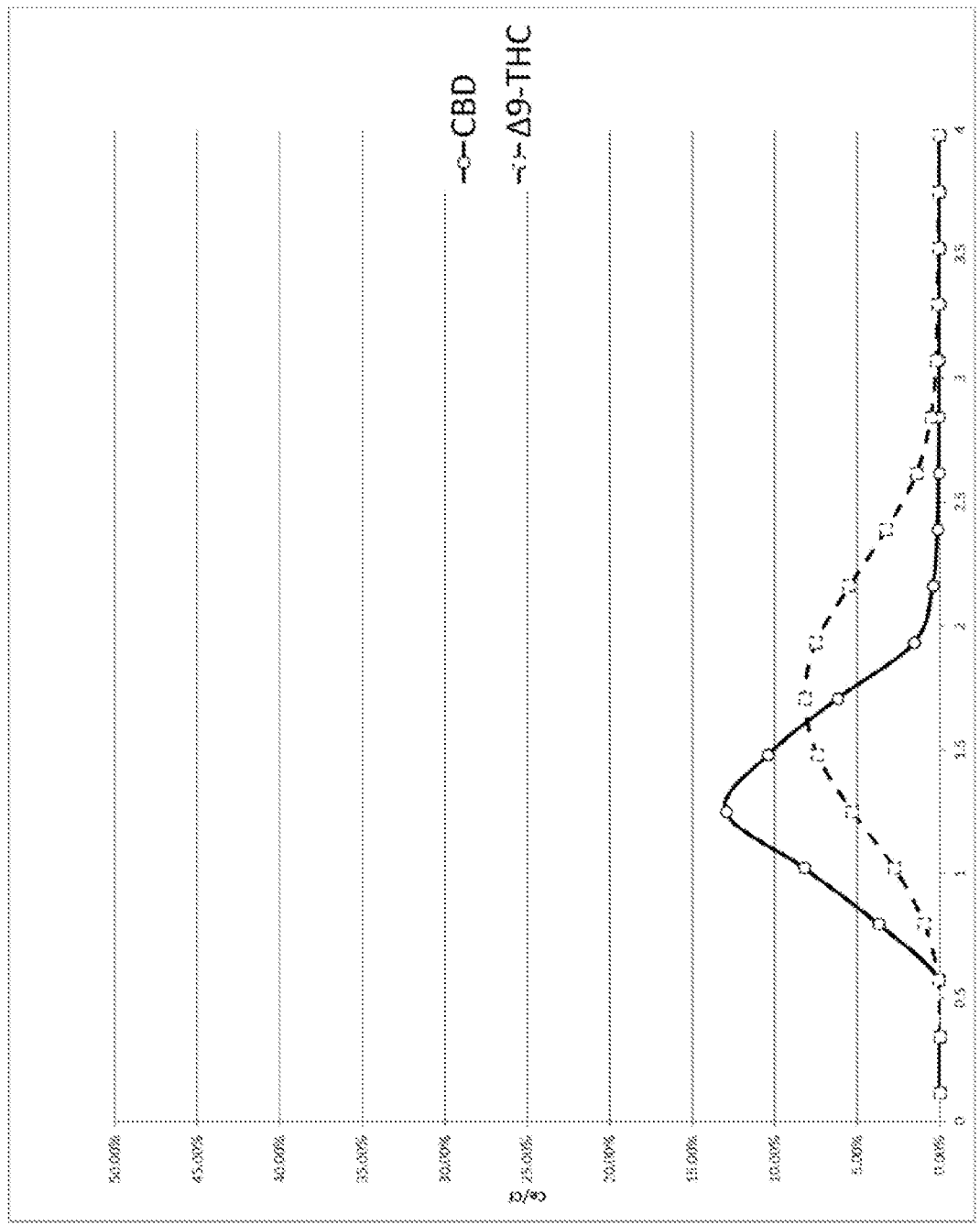
FIG. 18 depicts a pulse test of loading purified hemp oil onto a Chromalite® PCG600M resin and 1-propanol/water (polarity 0.664) as the desorbent.

The ability to remove THC from refined oil by reverse phase chromatography was evaluated by pulse test: refined oil was mixed 1:1 by weight with a D1 comprising 1-propanol and water. 19.8 ml were loaded onto a column packed with Chromalite® PCG600M and eluted with D1 of polarity 0.664 (3.8 ml/min·cm$^2$) at 68° F. Fractions were collected and analyzed by the method of example 1 for cannabinoids. FIG. 18 shows the concentration of CBD and THC relative to their concentration in the feed.

Example 15: Remediation Results of Purified Cannabis Oil to Remove THC

Figure 19:
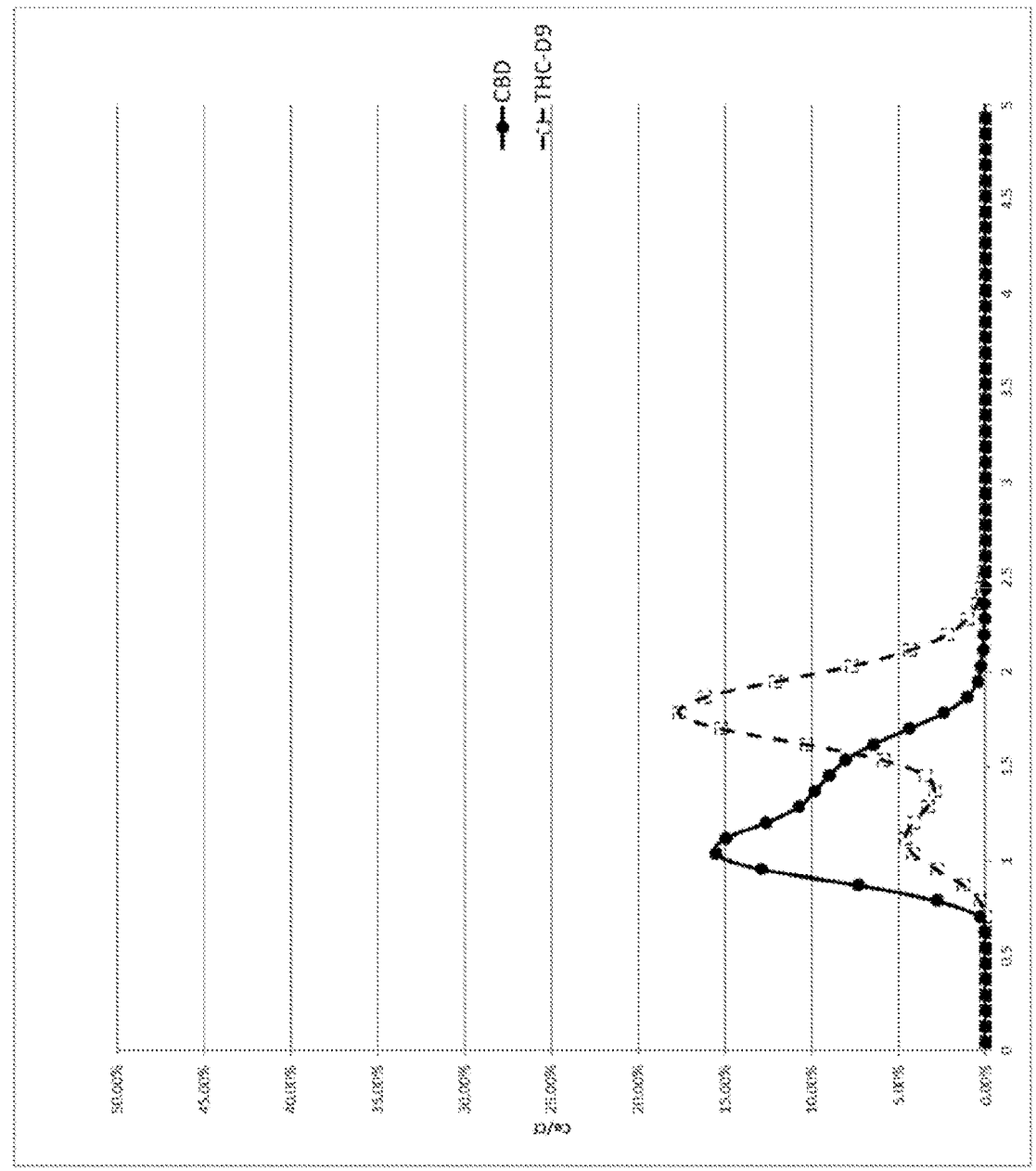
FIG. 19 depicts a pulse test of loading purified hemp oil onto a Chromalite® PCG600C resin, water/ethanol/hexane (polarity 0.660) as D1 desorbent, and water/ethanol/hexane (polarity of 0.033) as D2 desorbent.

The ability to remove THC from refined oil by reverse phase chromatography was evaluated by pulse test: refined oil was mixed 1:1 by weight with a D1 comprising water-ethanol-hexane (polarity 0.660). 19.8 ml were loaded onto a column packed with Chromalite® PCG600C. The column was eluted with D1 for 1 BV, then eluted with D2 (polarity of 0.033). Fractions were collected and analyzed by the method of example 1 for cannabinoids. FIG. 19 shows the concentration of CBD and THC relative to their concentration in the feed.

Example 16: Remediation Results of Purified Cannabis Oil to Remove THC

Figure 20:
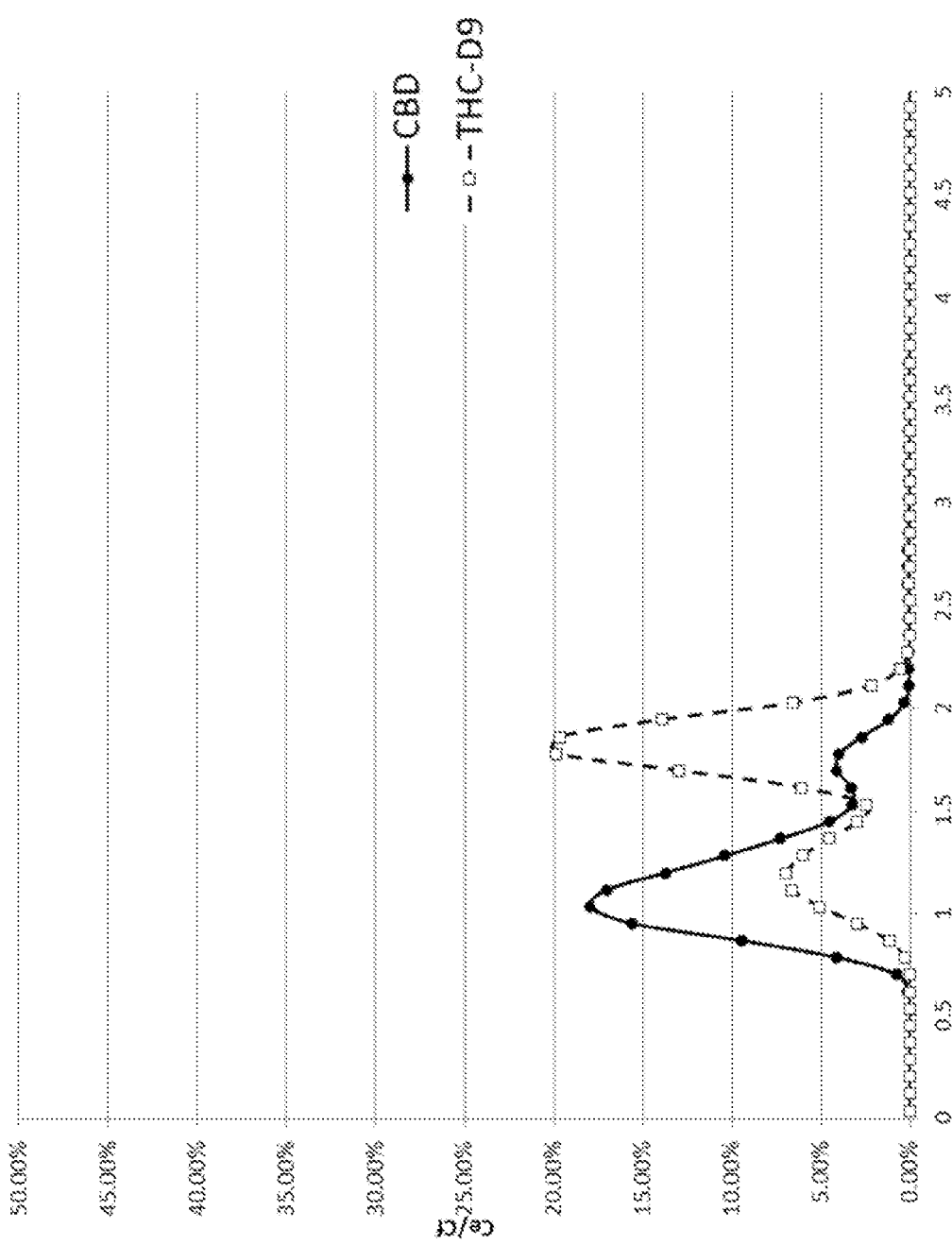
FIG. 20 depicts a pulse test of loading purified hemp oil onto a Chromalite® PCG600M resin, water/ethanol/hexane (polarity 0.660) as D1 desorbent, and water/ethanol/hexane (polarity 0.033) as D2 desorbent.

The ability to remove THC from refined oil by reverse phase chromatography was evaluated by pulse test: refined oil was mixed 1:1 by weight with a D1 comprising water-ethanol-hexane (polarity 0.660). 19.8 ml were loaded onto a column packed with Chromalite® PCG600M. The column was eluted with D1 for 1 BV, then eluted with D2 (polarity 0.033). Fractions were collected and analyzed by the method of example 1 for cannabinoids. FIG. 20 shows the concentration of CBD and THC relative to their concentration in the feed.

Example 17: Remediation Results of Purified Cannabis Oil to Remove THC

Figure 21:
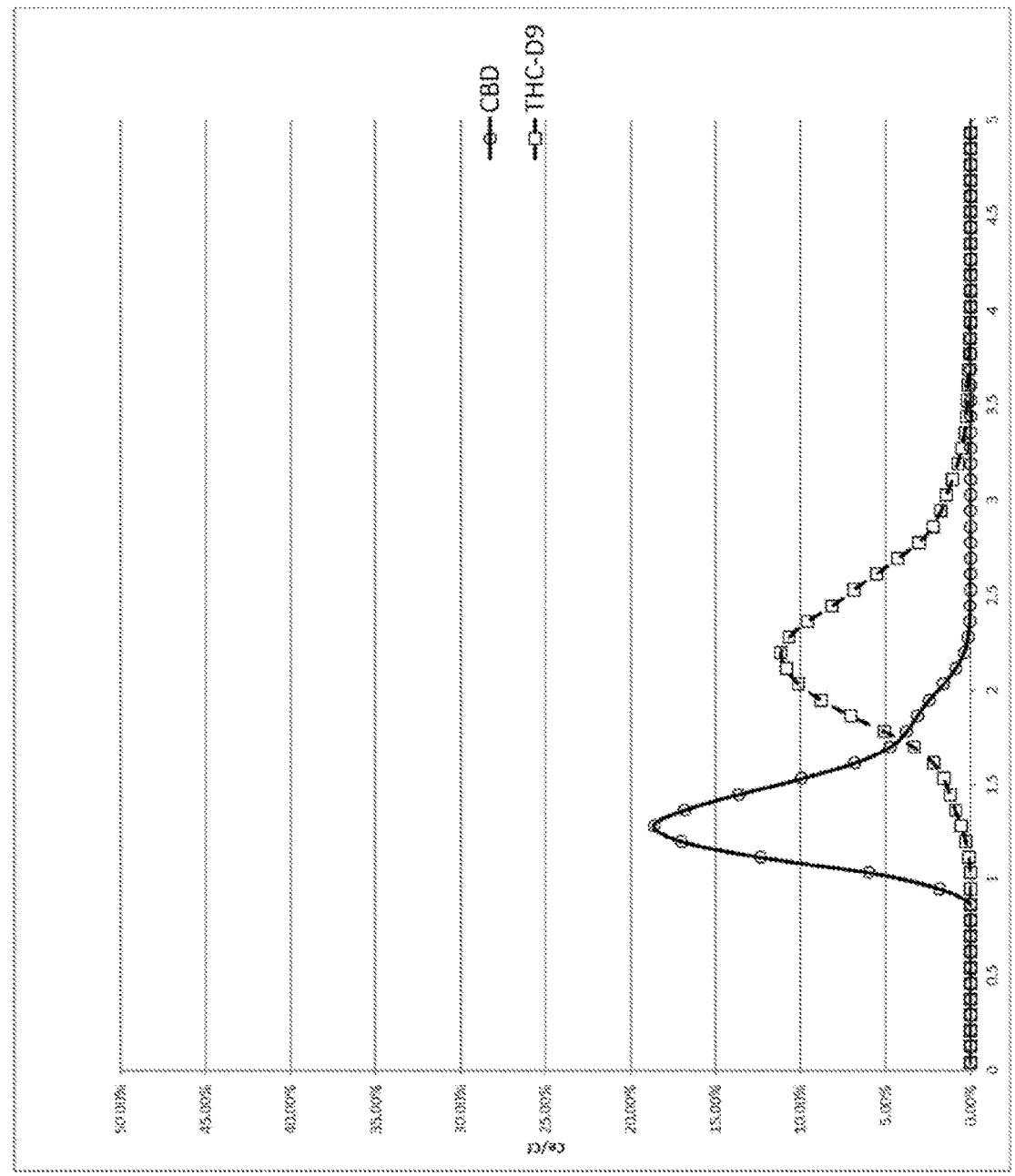
FIG. 21 depicts a pulse test of loading purified hemp oil onto a Chromalite® PCG600M resin, water/ethanol (polarity 0.696) as D1 desorbent, and water/ethanol (polarity 0.671) as D2 desorbent.

The ability to remove THC from refined oil by reverse phase chromatography was evaluated by pulse test: refined oil was mixed 1:1 by weight with a D1 comprising water-ethanol (polarity 0.696). 19.8 ml were loaded onto a column packed with Chromalite® PCG600M. The column was eluted with D1 for 1 BV, then eluted with D2 (polarity 0.671). Fractions were collected and analyzed by the method of example 1 for cannabinoids. FIG. 21 shows the concentration of CBD and THC relative to their concentration in the feed. After each run, the column lost its separation power and the process had to be stopped for regenerating the resin with a solvent of lower polarity, e.g. ethyl acetate, an alkane, such as pentane, hexane, cyclohexane, heptane or mixtures of alkanes, water, alcohol or esters.

Example 18: Remediation Results of Purified Cannabis Oil to Remove THC

Figure 22:
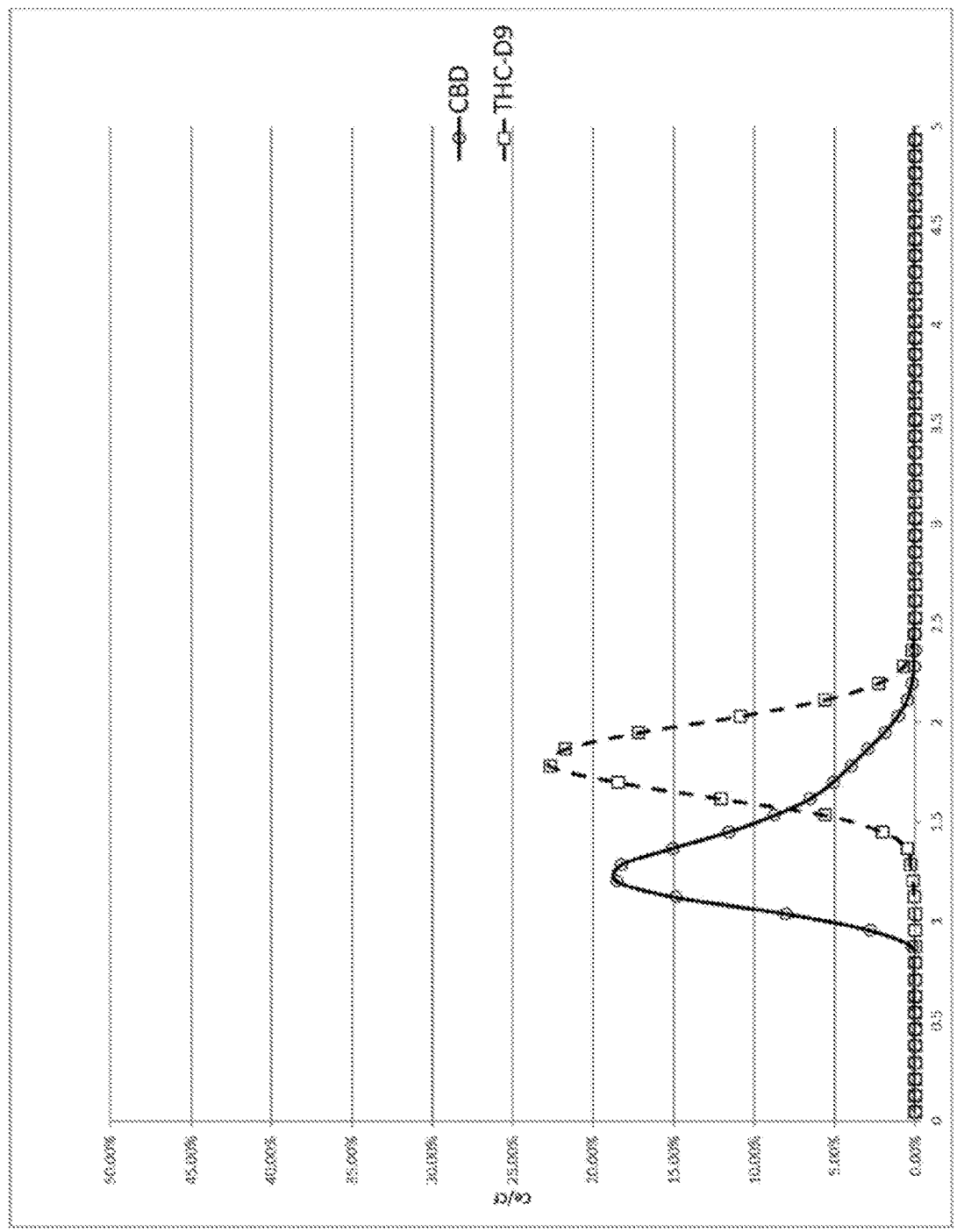
FIG. 22 depicts a pulse test of loading purified hemp oil onto a Chromalite® PCG600M resin, water/ethanol (polarity 0.664) as D1 desorbent, and pentane (polarity 0.009) as D2 desorbent.

The ability to remove THC from refined oil by reverse phase chromatography was evaluated by pulse test: refined oil was mixed 1:1 by weight with a D1 comprising water-ethanol (polarity 0.664). 19.8 ml were loaded onto a column packed with Chromalite® PCG600M. The column was eluted with D1 for 0.75 BV, then eluted with pentane (polarity 0.009). Fractions were collected and analyzed by the method of example 1 for cannabinoids. FIG. 22 shows the concentration of CBD and THC relative to their concentration in the feed.

Example 19: Remediation Method of Purified Cannabis Oil to Remove THC

Purified oil was feed into a SSMB system (1-2-2-1 setup) using Chromalite® PCG600M as solid phase adsorbent and a water-ethanol desorbent as D1 with a polarity of 0.682. Purified oil according to the current disclosure can run for prolonged periods (e.g., weeks, months, or years) without fouling. When a less pure oil was run, for example, a distillate made without applying the process of the second refining of the current disclosure, fouling was observed after less than 2 weeks accompanied with loss of separation. The resin could be regenerated by washing with ethyl acetate, then washing the ethyl acetate with D1 solvent. Such regeneration was accompanied with significant down time to the process and excessive amounts of solvents that need to be treated.

Figure 23:
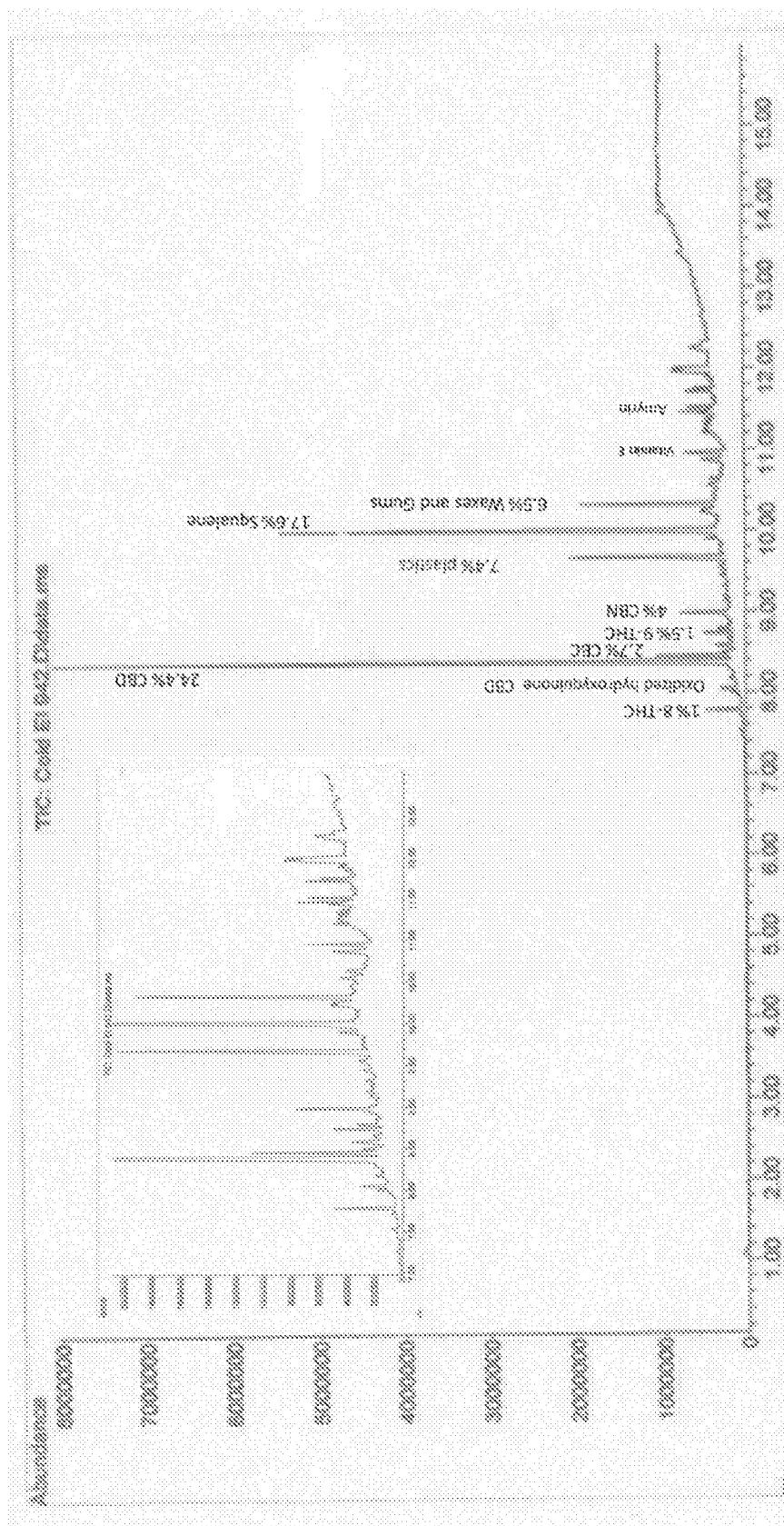
FIG. 23 depicts a pulse test of a regeneration eluent for the remediation system with a desorbing solvent.

Analysis of a regeneration eluent with a desorbing solvent (e.g. ethyl acetate, hexane, pentane) indicates that fouling compounds can include those depicted in FIG. 23. The regeneration eluent was obtained after a SSMB remediation run performed for six-weeks, using water-ethanol desorbant as the D1, on a filtered and decarboxylated distilled oil described herein, was paused. The fouling compounds indicated in FIG. 23 were collected after desorption of the SSMB system using a non-polar solvent (e.g., hexanes). The fouling compounds desorbed from the SSMB column system were, for example, polar and non-polar constituents embedded within the SSMB column. This result indicates that the SSMB column system can be replenished with a non-polar solvent (e.g., a D2 described herein). Also, fewer fouling compounds are present within the SSMB column system when a non-polar solvent is used in the solvent mixture for the SSMB run (e.g., example 20). These result show that the solvent systems for remediation described herein can prevent or eliminate fouling of the remediation system before, during, or after the remediation process by removing compounds that cause fouling (e.g., constituents that get embedded within the remediation system like, for example, cannabinoids, triterpenes, sterols, steroids, waxes and gums, high molecular weight biomass compounds, etc.). While in some cases separation media contamination can be minimized or eliminated with a D2 solvent as an integral element of the step sequence, prudence can dictate the removal of the fouling constituents by upstream refining processes described herein; thus, minimizing the amount of time D2 desorption may be required in the step sequence for maximum operating productivity and efficiency.

Example 20: Remediation Results of Purified Cannabis Oil to Remove THC

Figure 24:
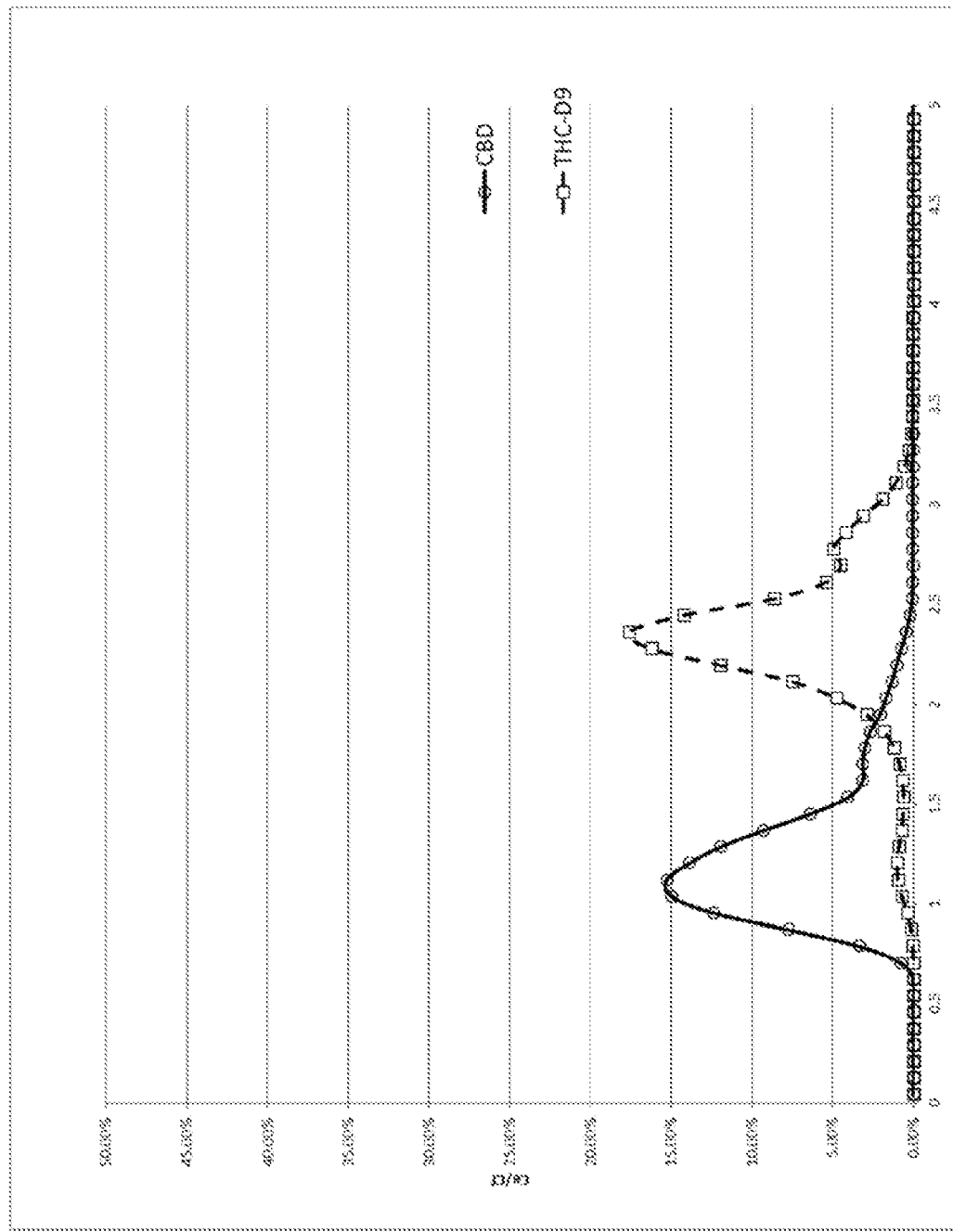
FIG. 24 depicts a pulse test of loading purified hemp oil onto a Chromalite® PCG600M resin, water/ethanol/pentane (polarity 0.680) as D1 desorbent, and water/ethanol/pentane (polarity 0.045) as D2 desorbent.

The ability to remove THC from filtered and de-carboxylated distillate (e.g., oil distillate that had not been degummed or dewaxed) by reverse phase chromatography was evaluated by pulse test: the oil distillate was mixed 35:65 by weight with a D1 comprising water-ethanol-pentane (polarity 0.680). 19.8 ml were loaded onto a column packed with Chromalite® PCG600M. The column was eluted with D1 for 1.5 BV, then eluted with D2 (polarity 0.045) for 1.375 BV, followed by 0.75BV of D1. Fractions were collected and analyzed by the method of example 1 for cannabinoids. FIG. 24 shows the concentration of CBD and THC relative to their concentration in the feed.

Example 21: Remediation Results of Purified Cannabis Oil to Remove THC

Figure 25:
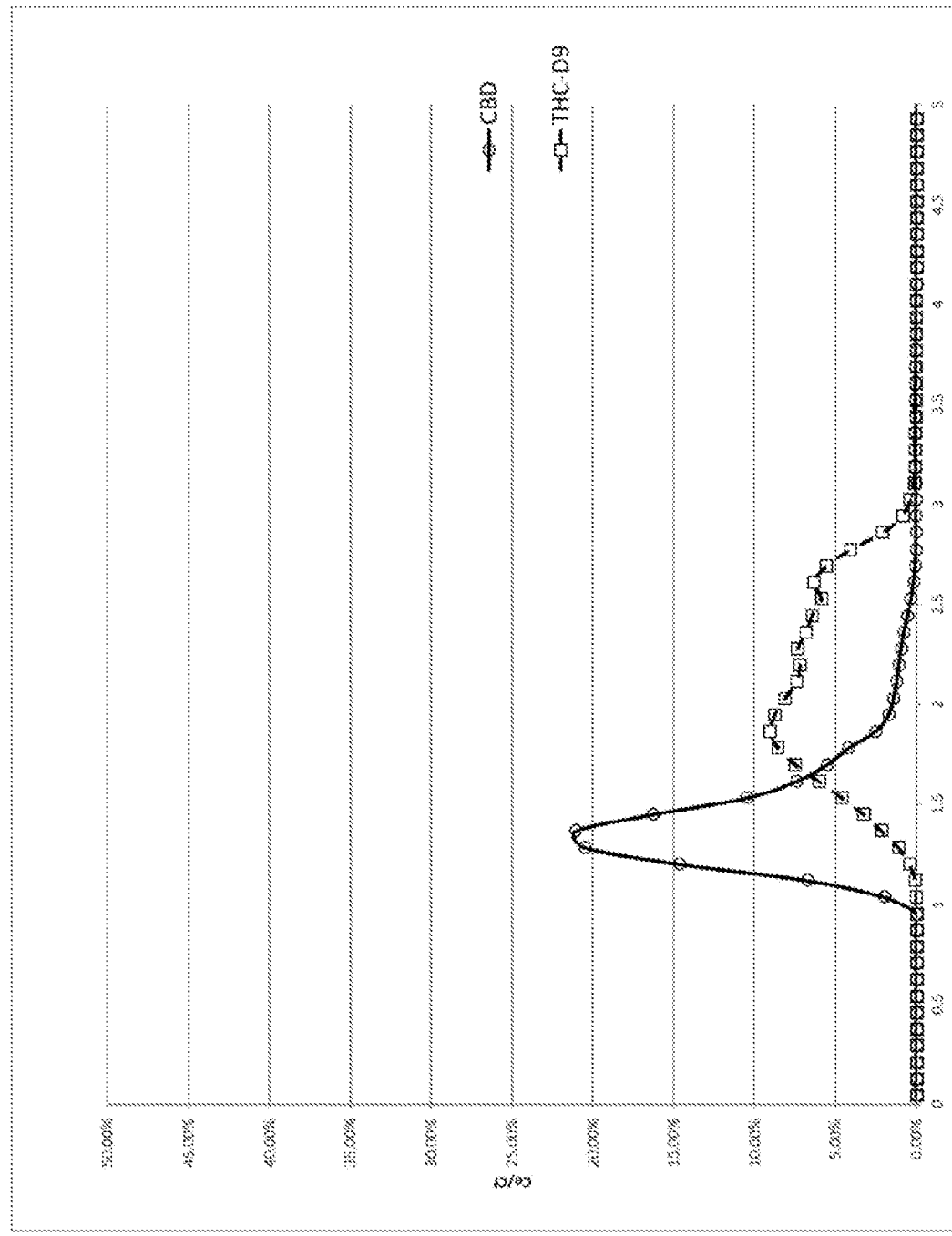
FIG. 25 depicts a pulse test of loading purified hemp oil onto a Chromalite® PCG600M resin, water/ethanol/hexane (polarity 0.659) as D1 desorbent, and water/ethanol/hexane (polarity 0.029) as D2 desorbent.

The ability to remove THC from filtered and de-carboxylated distillate (e.g., oil distillate that had not been degummed or dewaxed) by reverse phase chromatography was evaluated by pulse test: the oil distillate was mixed 35:65 by weight with a D1 comprising water-ethanol-hexane (polarity 0.659). 19.8 ml were loaded onto a column packed with Chromalite® PCG600M. The column was eluted with D1 for 1.75 BV, then eluted with 1.375 BV D2 (polarity 0.029), followed by 0.75 BV D1. Fractions were collected and analyzed by the method of example 1 for cannabinoids. FIG. 25 shows the concentration of CBD and THC relative to their concentration in the feed.

Example 22: Remediation Method of Purified Cannabis Oil to Remove THC

Purified oil was feed into a SSMB system (1-2-2-1 setup) using Chromalite® PCG600M as solid phase adsorbent and a water-ethanol desorbent as D1 with a polarity of 0.682. Purified oil according to the current disclosure can run for prolonged periods (e.g., weeks, months, or years) without fouling. When a less pure oil was run, for example, a distillate made without applying the process of the second refining of the current disclosure, fouling was observed after less than 2 weeks accompanied with loss of separation. The resin could be regenerated by washing with ethyl acetate, then washing the ethyl acetate with D1 solvent. Such regeneration was accompanied with significant down time to the process and excessive amounts of solvents that need to be treated.

TABLE 7

SSMB sequence for the remediation of purified oil using a dual desorbent mode

| Step | SSMB |
| --- | --- |
| Step 1 (D1 to Extract; Feed to Raffinate) | |
| Step 1 Time | 673.5 seconds |
| Raffinate Flow | 1.71 ml/min |
| Extract Flow | 32.5 ml/min |
| Step 2 (D1 to Raffinate) | |
| Step 2 Time | 123.3 seconds |
| Extract Flow | — |
| Raffinate Flow | 10.2 ml/min |
| Step 3 (Recycle) | |
| Step 3 Time | 1514.2 seconds |
| Recycle Flow | 6.26 ml/min |
| Results | |
| Purity - CBD/THC | >91.2%/0.010% |
| Recovery - CBD | 92% |
| Desorb to Feed Ratio | 20.2 |
| Total Step Time | 38.67 Minutes |

Table 8 summarizes the concentrations of various cannabinoids identified in the feed, extract and raffinate streams in this separation.

TABLE 8 cannabinoids identified by HPLC in the feed, extract and raffinate streams.

| Constituent | Feed, % wt/wt | Extract. % wt/wt | Raffinate. % wt/wt |
| --- | --- | --- | --- |
| CBDVA | 0.000 | 0.010 | 0.80 |
| CBDV | 0.460 | 0.000 | 0.530 |
| CBDA | 0.000 | 0.600 | 0.400 |
| CBG | 1.230 | 0.060 | 1.330 |
| CBD | 86.420 | 34.980 | 91.220 |
| THCV | 0.010 | 0.190 | 0.000 |
| THCVA | 0.000 | 0.010 | 0.020 |
| CBN | 0.270 | 4.520 | 0.000 |
| Δ9-THC | 2.390 | 11.950 | 0.010 |
| Δ8-THC | 0.050 | 0.000 | 0.000 |
| CBL | 0.160 | 0.940 | 0.000 |
| CBC | 3.110 | 11.990 | 0.040 |
| THCA | 0.000 | 0.000 | 0.010 |
| CBCA | 1.410 | 0.840 | 0.150 |

Example 23: Remediation Method of Purified Cannabis Oil to Remove THC

Filtered and de-carboxylated distillate oil (e.g., distillate that had not been degummed or dewaxed) was diluted with D1 desorbent (35:65) and feed into a SSMB system (1-2-2-1 setup) using Chromalite® PCG600M as solid phase adsorbent and a water-ethanol-hexane desorbent as D1 with a polarity of 0.659. The system could run for prolonged time to remediate THC from the oil without fouling, using a water-ethanol-hexane desorbent as D2 with a polarity of 0.029.

TABLE 9

SSMB sequence for the remediation of purified oil using a dual desorbent mode

| Step | SSMB |
| --- | --- |
| Step 1 (D2 to Extract; Feed to Raffinate) | |
| Step 1 Time | 399.2 seconds |
| Raffinate Flow | 1.58 ml/min |
| Extract Flow | 30.8 ml/min |
| Step 2 (D1 to Extract; Feed to Raffinate) | |
| Step 2 Time | 294.3 seconds |
| Raffinate Flow | 1.58 ml/min |
| Extract Flow | 30.8 ml/min |
| Step 3 (D1 to Raffinate) | |
| Step 3 Time | 190.1 seconds |
| Raffinate Flow | 8.0 ml/min |
| Extract Flow | — |
| Step 4 (Recycle) | |
| Step 4 Time | 937.3 seconds |
| Recycle Flow | 9.1 ml/min |
| Results | |
| Purity - CBD/THC | >97.%/<1000 ppm |
| Recovery - CBD | 90% |
| Desorb to Feed Ratio | 20.9 |
| Total Step Time | 30.3 Minutes |

TABLE 10

Alternative SSMB sequence for the remediation of purified oil using a dual desorbent mode

| Step | SSMB |
| --- | --- |
| Step 1 (D2 to Extract; Feed to Raffinate) | |
| Step 1 Time | 399.2 seconds |
| Raffinate Flow | 2.74 ml/min |
| Extract Flow | 30.8 ml/min |
| Step 2 (D1 to Extract; D1 to Raffinate) | |
| Step 2 Time | 294.3 seconds |
| Raffinate Flow | 5.17 ml/min |
| Extract Flow | 30.8 ml/min |
| Step 3 (Recycle) | |
| Step 3 Time | 937.3 seconds |
| Recycle Flow | 9.1 ml/min |
| Results | |
| Purity - CBD/THC | >97%/<1000 ppm |
| Recovery - CBD | >90% |
| Desorb to Feed Ratio | 20.9 |
| Total Step Time | 27.2 minutes |

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for purifying an oil, the method comprising:
a) contacting said oil comprising at least one cannabinoid constituent and at least one non-cannabinoid constituent with a compound having a boiling point greater than or equal to about 200° C. to produce a mixture comprising said oil and said compound; and
b) directing at least a portion of said mixture into a distillation unit and separating, in said distillation unit, said at least one cannabinoid constituent from said at least one non-cannabinoid constituent by distillation, thereby generating a purified oil having a higher concentration of said at least one cannabinoid constituent than said oil, wherein said separating is facilitated by said compound.

2. The method of claim 1, wherein said compound has one or more of:
(i) a density of greater than or equal to about 0.80 g/cm$^3$;
(ii) a boiling point greater than or equal to about 250° C. at 5 torr;
(iii) a viscosity of less than or equal to about 30 centiStokes at 90° C.;
(iv) at least 8 carbon atoms; and
(v) a miscibility with said oil.

3. The method of claim 2, wherein said compound has (i)-(v).

4. The method of claim 1, wherein said compound comprises a homogeneous glyceride, a heterogeneous glyceride, a fatty acid, a fatty acid ester, or any combination or derivative thereof.

5. The method of claim 1, further comprising, prior to a), refining said oil by contacting said oil with at least one of a basic amino acid, a protamine, clay, water, activated carbon, filter aid, ion exchange resin, or a combination thereof.

6. The method of claim 1, wherein said purified oil comprises said at least one cannabinoid constituent at a concentration of greater than or equal to about 70% weight by weight percentage (wt/wt %).

7. The method of claim 1, wherein said purified oil has a higher concentration of said at least one cannabinoid constituent than a purified oil generated in said distillation unit in the absence of said compound.

8. The method of claim 1, further comprising, (c) directing at least a portion of said purified oil to a remediation unit in fluid communication with said distillation unit to generate one or more streams, wherein at least one of said one or more streams comprises said at least one cannabinoid constituent.

9. The method of claim 8, wherein said at least one of said one or more streams comprises at least about 85 wt/wt % of said at least one cannabinoid constituent.

10. The method of claim 8, wherein said remediating unit comprises a sequential simulated moving bed (SSMB) chromatography unit operated in a dual desorbent mode.

11. The method of claim 10, wherein said dual desorbent mode comprises:
(a) passing a feed stream, which comprises said purified oil and a first desorbent (D1), into an adsorbent of said SSMB chromatography unit to generate two or more oil wave fronts, comprising a raffinate stream wave front and an extract stream wave front, wherein said raffinate stream wave front comprises said at least one cannabinoid constituent and said extract stream wave front comprises at least one constituent different from said at least one cannabinoid constituent;
(b) advancing said two or more oil wave fronts with said D1 through said SSMB chromatography unit;
(c) passing a second desorbent (D2) into said adsorbent to flush at least a portion of said extract stream wave front or said raffinate stream wave front; and
(d) generating from said SSMB chromatography unit said one or more streams, wherein said one or more streams are derived at least in part form said at least said portion of said extract stream wave front or said raffinate stream wave front.

12. The method of claim 11, wherein (a)-(d) are performed sequentially or substantially simultaneously.

13. The method of claim 11, further comprising, (1) stripping said D1 from said one or more streams, thereby producing one or more purified streams, and (2) removing water, solvent, or a combination thereof from said one or more purified streams to obtain said at least cannabinoid constituent.

14. The method of claim 11, further comprising, stripping said D1 and said D2 from said at least said portion of said extract stream wave front flushed in (c), thereby producing a residual oil, and, optionally, removing water from said residual oil to obtain a purified residual oil enriched with said at least one constituent different from said at least one cannabinoid constituent.

15. The method of claim 14, wherein said D1 and said D2 each form an azeotrope with different physical properties, wherein said stripping of said D1 is conducted under a condition different from a condition under which said stripping of said D2 is conducted.

16. The method of claim 11, further comprising, stripping, condensing, and mixing said D1 and said D2 passed through said SSMB chromatography unit in a liquid/liquid separation unit to provide a phase of recycled D1 and a phase of recycled D2, wherein said phase of recycled D1 and said phase of recycled D2 are redirected to said SSMB chromatography unit, and wherein said D1 and said D2 each comprise one or more solvents that form an azeotrope with water in a binary or ternary mixture.

17. The method of claim 16, wherein said binary mixture is ethanol-water or propanol-water, and wherein said ternary mixture is selected from the group consisting of pentane-ethanol-water, hexane-ethanol-water, acetone-propanol-water, ethyl acetate-ethanol-water, heptane-ethanol-water, and cyclohexane-ethanol-water.

18. The method of claim 16, wherein said azeotrope has a boiling point (i) of at most about 90° C. and (ii) that is lower than a boiling point of each of the one or more solvents of said binary or ternary mixture.

19. The method of claim 16, wherein said D1 and D2 separate into a first liquid phase and a second liquid phase from said ternary mixture at temperature from about 10° C. to about 50° C., and wherein said first liquid phase comprises said D1 and said second liquid phase comprises said D2.

* * * * *